US008329699B2

(12) United States Patent
Hendricks et al.

(10) Patent No.: US 8,329,699 B2
(45) Date of Patent: Dec. 11, 2012

(54) PYRROLOPYRAZINE KINASE INHIBITORS

(75) Inventors: Robert Than Hendricks, San Carlos, CA (US); Johannes Hermann, Jersey City, NJ (US); Rama Kondru, Morris Plains, NJ (US); Yan Lou, Clifton, NJ (US); Stephen Lynch, Westfield, NJ (US); Timothy D. Owens, Jersey City, NJ (US); Michael Soth, Glen Rock, NJ (US); Calvin Yee, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/110,053

(22) Filed: May 18, 2011

(65) Prior Publication Data
US 2011/0288097 A1    Nov. 24, 2011

Related U.S. Application Data

(60) Provisional application No. 61/346,502, filed on May 20, 2010, provisional application No. 61/475,286, filed on Apr. 14, 2011.

(51) Int. Cl.
*A61K 31/495* (2006.01)
(52) U.S. Cl. ........ 514/249; 544/350; 546/200; 548/518; 549/356; 549/429
(58) Field of Classification Search .................. 514/249; 544/350; 546/200; 548/518; 549/356, 429
See application file for complete search history.

(56) References Cited

U.S. PATENT DOCUMENTS

| 7,902,197 | B2 | 3/2011 | Elworthy et al. |
| 7,932,254 | B2 | 4/2011 | DuBois et al. |
| 7,939,531 | B2 | 5/2011 | Bamberg et al. |
| 2006/0148801 | A1 | 7/2006 | Hsieh et al. |
| 2007/0049615 | A1 | 3/2007 | Ibrahim et al. |
| 2009/0215750 | A1 | 8/2009 | Bamberg et al. |
| 2009/0215785 | A1 | 8/2009 | Dubois et al. |
| 2010/0267666 | A1 | 10/2010 | Bamberg et al. |
| 2011/0230414 | A1* | 9/2011 | Hendricks et al. ........... 514/17.7 |

FOREIGN PATENT DOCUMENTS

| WO | 01/47922 | 7/2001 |
| WO | 03/000688 | 1/2003 |
| WO | 03/082868 | 10/2003 |
| WO | 2007/077949 | 7/2007 |
| WO | 2007/084557 | 7/2007 |
| WO | 2008/033798 | 3/2008 |
| WO | 2008/063888 | 5/2008 |
| WO | 2008/079903 | 7/2008 |
| WO | 2008/084861 | 7/2008 |
| WO | 2008/147800 | 12/2008 |
| WO | 2009/106441 | 9/2009 |
| WO | 2009/106442 | 9/2009 |
| WO | 2009/106443 | 9/2009 |
| WO | 2009/106444 | 9/2009 |
| WO | 2009/106445 | 9/2009 |

OTHER PUBLICATIONS

Rice, L.M. et al., "Spiranes III.Ia.b Azaspiranes and Intermediates" J. Med. Chem. 6:388-402 (1963).

Sablayrolles et al., "Methyl-6 TH-pyrrolo[2,3-b]pyrazinecarboxylate-7 d'ethyle: structure et mecanishme d'obtention a partir de l'amino-2 pyrazine," Bulletin de la Societe Chimique de France:467-471 (Jul. 1989).
(International Search Report for PCT/EP2011/054171 Jun. 17, 2011).
(International Search Report for Corres PCT/EP2011/054091 Jun. 9, 2011).
(International Search Report PCT/EP2009/051761 May 8, 2009).
(International Search Report for PCT/EP2008/051761 May 8, 2009).
Catlett-Falcone, et al., Constitutive Activation of Stat3 Signaling Confers Resistance to Apoptosis in Human U266 Myeloma Cells; Immunity, 10:105-115 (1999).
Changelian, et al., Prevention of Organ Allograft Rejection by a Specific Janus Kinase 3 Inhibitor; Science (2003) 302:875-878.
Cheng, et al., Syk tyrosine kinase required for mouse viability and B-cell development; Nature (1995) 378:303-306.
Costello, et al., Critical role for the tyrosine kinase Syk in signalling through the high affinity IgE receptor of mast cells; Oncogene (1996) 13:2595-2605.
Demoulin, et al., A single tyrosine of the interleukin-9 (IL-9) receptor is required for STAT activation, antiapoptotic activity, and growth regulation by IL-9; Molecular and Cellular Biology (1996) 16:4710-4716. Horvath, et al., The state of the STATs: recent developments in the study of signal transduction to the nucleus; Current Opinion in Cell Biology (1997) 9:233-239.
Jurlander, et al., Characterization of Interleukin-10 Receptor Expression on B-Cell Chronic Lymphocytic Leukemia Cells; Blood (1997) 89:4146-4152.
Kaneko, et al., Rescue by cytokines of apoptotic cell death induced by IL-2 deprivation of human antigen-specific T cell clones; Clin. Exp. Immunol (1997) 109:185-193.
Kirken, R.A., Targeting JAK3 for Immune Suppression and Allograft Acceptance; Transplantation Proceedings (2001) 33:3268-3270.
Kudlacz, et al., The Novel JAK-3 Inhibitor CP-690550 Is a Potent Immunosuppressive Agent in Various Murine Models; American Journal of Transplantation (2004) 4:51-57.
Lach-Trifilieff, et al., Syk-deficient eosinophils show normal interleukin-5-mediated differentiation, maturation, and survival but no longer respond to FcγR activation; Blood (2000) 96:2506-2510.
Leonard et al., JAKS and STATS: biological Implications; Annu. Rev. Immunol (1998) 16:293-322.
Leonard, et al., Cytokine receptor signaling pathways; J. Allergy Clin. Immunol (2000) 105:877-88.
Leonard, W.J., Dysfunctional Cytokine Receptor Signaling in Severe Combined Immunodeficiency; Journal of Investigative Medicine (1996) 44:304-311.

(Continued)

*Primary Examiner* — Douglas M Willis
(74) *Attorney, Agent, or Firm* — George W. Johnston; Dennis P. Tramaloni; Jennifer L. Kisko

(57) ABSTRACT

The present invention relates to the use of novel pyrrolopyrazine derivatives of Formula I,

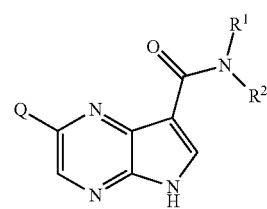

wherein the variables Q and $R^1$ and $R^2$ are defined as described herein, which inhibit JAK and SYK and are useful for the treatment of auto-immune and inflammatory diseases.

16 Claims, No Drawings

OTHER PUBLICATIONS

Malaviya, et al., Genetic and Biochemical Evidence for a Critical Role of Janus Kinase (JAK)-3 in Mast Cell-Mediated Type 1 Hypersensitivity Reactions; Biochemical and Biophysical Res. Communications (1999) 257:807-813.

Malaviya, et al., Targeting Janus Kinase 3 in Mast Cells Prevents Immediate Hypersensitivity Reactions and Anaphylaxis; The Journal of Biological Chemistry (1999) 274:27028-27038.

Mueller-Ladner, et al., Activation of the IL-4 STAT Pathway in Rheumatoid Synovium; Journal of Immunology (2000) 164:3894-3901.

Nakamura, et al., An Epidermal Growth Factor Receptor/Jak2 Tyrosine Kinase Domain Chimera Induces Tyrosine Phosphorylation of Stat5 and Transduces a Growth Signal in Hematopoietic Cells; Journal of Biological Chemistry (1996) 271:19483-19488.

Nielsen, et al., Constitutive activation of a slowly migrating isoform of Stat3 in mycosis fungoides: Tyrphostin AG490 inhibits Stat3 activation and growth of mycosis fungoides tumor cell lines; Proc. Natl. Acad. Sci. USA (1997) 94:6764-6769.

Rane, et al., Janus Kinases: Components of Multiple Signaling Pathways; Oncogene (2000) 19:5662-5679.

Roberts, et al., Janus kinase 3 (JAK3) deficiency: clinical, immunologic, and molecular analyses of 10 patients and outcomes of stem cell transplantation; Blood (2004) 103:2009-2018.

Stenton, et al., Inhibition of Allergic Inflammation in the Airways Using Aerosolized Antisense to Syk Kinase; J. Immunol. (2002) 169:1028-1036.

Sudbeck, et al., Structure-based Design of Specific Inhibitors of Janus Kinase 3 as Apoptosis-inducing Antileukemic Agents; Clinical Cancer Research (1999) 5:1569-1582.

Suzuki, et al., Role of common cytokine receptor γ chain (γc)- and Jak3-dependent signaling in the proliferation and survival of murine mast cells; Blood (2000) 96:2172-2180.

Taylor, et al., Activation of the High-Affinity Immunoglobulin E Receptor FceRI in RBL-2H3 Cells is Inhibited by Syk SH2 Domains; Molecular and Cellular Biology (1995) 15:4149-4157.

Trieu, et al., A Specific Inhibitor of Janus Kinase-3 Increases Survival in a Transgenic Mouse Model of Amyotrophic Lateral Sclerosis; Biochemical and Biophysical Research Comm. (2000) 267:22-25.

Turner, et al., Perinatal lethality and blocked B-cell development in mice lacking the tyrosine kinase Syk; Nature (1995) 378:298-302.

Verbsky, et al., Nonhematopoietic Expression of Janus Kinase 3 is Required for Efficient Recruitment of Th2 Lymphocytes and Eosinophils in OVA-Induced Airway Inflammation; Journal of Immunology (2002) 168:2475-2482.

Wong, et al., Targeting Syk as a treatment for allergic and autoimmune disorders; Expert Opinion Investig. Drugs (2004) 13:743-762.

Yamamoto, et al., The Orally Available Spleen Tyrosine Kinase Inhibitor 2-[7-(3,4-Dimethoxyphenyl)-imidazol[1,2-c] pyrimidin-5-ylamino]-nicotinamide Dihydrochloride (BAY 61-3606) Blocks Antigen-Induced Airway Inflammation in Rodents; J. of Pharmacology and Exper. Therapeutics (2003) 306:1174-1181.

Yu, et al., Constitutive Activation of the Janus Kinase-STAT Pathway in T Lymphoma Overexpressing the Lck Protein Tyrosine Kinase; J. Immunol. (1997) 159:5206-5210.

International Search Report for PCT/EP2011/057910 dated Jul. 4, 2011.

\* cited by examiner

PYRROLOPYRAZINE KINASE INHIBITORS

PRIORITY TO RELATED APPLICATIONS

This application is entitled to the benefit of U.S. provisional patent application Ser. No. 61/475,286 filed on Apr. 14, 2011, and U.S. provisional patent application Ser. No. 61/346,502 filed on May 20, 2010.

CROSS-REFERENCE TO RELATED APPLICATIONS

This application is related to U.S. application Ser. No. 12/378,837, filed on Feb. 20, 2009, Ser. No. 12/378,869, filed on Feb. 20, 2009, Ser. No. 12/378,971, filed on Feb. 20, 2009, Ser. No. 12/378,977, filed on Feb. 20, 2009, and Ser. No. 12/378,978, filed on Feb. 20, 2009, each of which is expressly incorporated herein by reference.

FIELD OF THE INVENTION

The present invention relates to the use of novel pyrrolopyrazine derivatives which are JAK and SYK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immun. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (J. Immunol. 168 (2002), pp. 2475-2482). Because bone marrow transplants for SCID are curative (Blood 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (J. Investig. Med. 44 (1996), pp. 304-311; Curr. Opin. Cell Biol. 9 (1997), pp. 233-239), the ubiquitous distribution of STATs and the fact that those molecules lack enzymatic activity that could be targeted with small-molecule inhibitors has contributed to their non-selection as key targets for immunosuppression.

SYK (Spleen Tyrosine Kinase) is a non-receptor tyrosine kinase that is essential for B-cell activation through BCR signaling. SYK become activated upon binding to phosphoryated BCR and thus initiates the early signaling events following BCR activation. Mice deficient in SYK exhibit an early block in B-cell development (Cheng et al. Nature 378: 303, 1995; Turner et al. Nature 378:298, 1995). Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma (reviewed in Wong et al. Expert Opin Investig Drugs 13:743, 2004). SYK binds to the phosphorylated gamma chain of FcεRI via its SH2 domains and is essential for downstream signaling (Taylor et al. Mol. Cell. Biol. 15:4149, 1995). SYK deficient mast cells demonstrate defective degranulation, arachidonic acid and cytokine secretion (Costello et al. Oncogene 13:2595, 1996). This also has been shown for pharmacologic agents that inhibit SYK activity in mast cells (Yamamoto et al. J Pharmacol Exp Ther 306:1174, 2003). Treatment with SYK antisense oligonucleotides inhibits antigen-induced infiltration of eosinophils and neutrophils in an animal model of asthma (Stenton et al. J Immunol 169:1028, 2002). SYK deficient eosinophils also show impaired activation in response to Fc R stimulation (Lach-Trifilieffe et al. Blood 96:2506, 2000). Therefore, small molecule inhibitors of SYK will be useful for treatment of allergy-induced inflammatory diseases including asthma.

In view of the numerous conditions that are contemplated to benefit by treatment involving modulation of the JAK and/or SYK pathways it is immediately apparent that new compounds that modulate JAK and/or SYK pathways and methods of using these compounds should provide substantial therapeutic benefits to a wide variety of patients. Provided herein are novel pyrrolopyrazine derivatives for use in the treatment of conditions in which targeting of the JAK and/or SYK pathways or inhibition of JAK or SYK kinases, particularly JAK3, and are therapeutically useful for the treatment of auto-immune and inflammatory diseases.

SUMMARY OF THE INVENTION

The novel pyrrolopyrazine derivatives provided herein selectively inhibit JAK3 and are useful for the treatment of auto-immune and inflammatory diseases. The compounds of the invention modulate the JAK and/or SYK pathways and are useful novel pyrrolopyrazine derivatives for the treatment of auto-immune and inflammatory diseases, wherein preferred compounds selectively inhibit JAK3. For example, the compounds of the invention may inhibit JAK3 and SYK, wherein preferred compounds are selective for JAK3 of the JAK kinases and are useful novel pyrrolopyrazine derivatives for the treatment of auto-immune and inflammatory diseases. The amide linker at the 7-position of the 5H-pyrrolo[2,3-b] pyrazines affords the compounds of formula I and I' unexpected increased potency in inhibition of JAK and Syk kinases compared to 5H-pyrrolo[2,3-b]pyrazines with other moieties at that position. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases.

The application provides a compound of Formula I

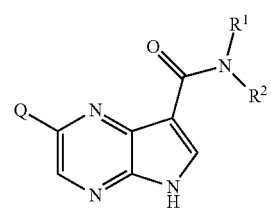

wherein:

$R^1$ is H or OH;

$R^2$ is phenyl, heterocycloalkyl, heteroaryl or cycloalkyl, each optionally substituted with one or more $R^{2'}$;

each $R^{2'}$ is independently hydroxy, halo, oxo, lower alkyl, lower alkenyl, lower alkynyl, lower haloalkyl, lower alkoxy, lower haloalkoxy, lower hydroxyalkyl, amino, lower alkylamino, lower dialkylamino, cyano, lower cyanoalkyl, cycloalkyl, heterocycloalkyl, C(=O)R$^3$, or S(=O)$_2$R$^3$;
each R$^3$ is independently OH, cycloalkyl or lower alkyl;
Q is Q$^2$, Q$^3$, or Q$^4$;
Q$^2$ is heterocycloalkyl, cycloalkyl, cycloalkenyl, heterocloalkyl phenyl, heteroaryl, biaryl, or heterobiaryl, optionally substituted with one or more Q$^{2a}$;
Q$^{2a}$ is Q$^{2b}$ or Q$^{2c}$;
Q$^{2b}$ is halogen, oxo, hydroxy, —CN, —SCH$_3$, —S(O)$_2$CH$_3$, or —S(=O)CH$_3$;
Q$^{2c}$ is Q$^{2d}$ or Q$^{2e}$;
or two Q$^{2a}$ come together to form a bicyclic ring system, optionally substituted with one or more Q$^{2b}$ or Q$^{2c}$;
Q$^{2d}$ is —O(Q$^{2e}$), —S(=O)$_2$(Q$^{2e}$), —C(=O)N(Q$^{2e}$)$_2$, —S(O)$_2$(Q$^{2e}$), —C(=O)(Q$^{2e}$), —C(=O)O(Q$^{2e}$), —N(Q$^{2e}$)C(=O)(Q$^{2e}$), —N(Q$^{2e}$)C(=O))(Q$^{2e}$), or —N(Q$^{2e}$)C(=O)N(Q$^{2e}$)$_2$;
each Q$^{2e}$ is independently H or Q$^{2e'}$;
each Q$^{2e'}$ is independently lower alkyl, phenyl, benzyl, lower haloalkyl, cycloalkyl, cycloalkenyl, heterocycloalkyl, or heteroaryl, optionally substituted with one or more Q$^{2f}$;
Q$^{2f}$ is Q$^{2g}$ or Q$^{2h}$;
Q$^{2g}$ is halogen, hydroxy, cyano, oxo, or —C(=O)(Q$^{2h}$);
Q$^{2h}$ is lower alkyl, lower haloalkyl, lower alkoxy, amino, phenyl, benzyl, cycloalkyl, heterocycloalkyl, or heteroaryl, optionally substituted with one or more Q$^{2i}$;
Q$^{2i}$ is halogen, hydroxy, cyano, lower alkyl, lower haloalkyl, or lower alkoxy;
Q$^3$ is —O-Q$^{3a}$, —S-Q$^{3a}$, —C(=O)(Q$^{3a}$), —O(CH$_2$)$_m$C(=O)(Q$^{3a}$), —S(=O)(Q$^{3a}$), —S(=O)$_2$(Q$^{3a}$), —N(Q$^{3a}$)$_2$, —N(Q$^{3a}$)S(=O)$_2$(Q$^{3a}$), —N(Q$^{3a}$)C(=O)(Q$^{3a}$), —C(=O)N(Q$^{3a}$)$_2$, N(Q$^{3a}$)C(=O)N(Q$^{3a}$)$_2$ or —N(Q$^{3a}$)(CH$_2$)$_m$C(=O)N(Q$^{3a}$)$_2$;
each Q$^{3a}$ is independently Q$^{3b}$ or Q$^{3c}$;
m is 0, 1, or 2;
Q$^{3b}$ is H;
Q$^{3c}$ is lower alkyl, lower haloalkyl, phenyl, cycloalkyl, heterocycloalkyl, or heteroaryl, optionally substituted with one or more Q$^{3d}$;
each Q$^{3d}$ is independently Q$^{3e}$ or Q$^{3f}$;
Q$^{3e}$ is halogen or hydroxy;
Q$^{3f}$ is lower alkyl, lower alkoxy, lower haloalkyl, phenyl, cycloalkyl, heterocycloalkyl, or heteroaryl, optionally substituted with one or more Q$^{3g}$;
or two Q$^{3f}$ together form a cycloalkyl, heterocycloalkyl, or heteroaryl, optionally substituted with one or more Q$^{3g}$;
each Q$^{3g}$ is independently halogen, hydroxy, lower alkyl, lower hydroxyalkyl, lower haloalkyl, amido, or lower alkoxy;
Q$^4$ is Q$^{4a}$ or Q$^{4b}$;
Q$^{4a}$ is 1 hydroxy, halogen, or cyano;
Q$^{4b}$ is lower alkyl, lower alkoxy, lower alkynyl, lower alkenyl, lower hydroxyalkyl, amino, or lower haloalkyl, optionally substituted with one or more Q$^{4c}$;
Q$^{4c}$ is Q$^{4d}$ or Q$^{4e}$;
each Q$^{4d}$ is independently halogen, hydroxy, or cyano;
each Q$^{4e}$ is independently lower alkyl, lower haloalkyl, lower alkoxy, amino, cycloalkyl, phenyl, heterocycloalkyl, or heteroaryl, optionally substituted with one or more Q$^{4f}$; and
each Q$^{4f}$ is independently hydroxy, halogen, lower alkyl, lower alkenyl, oxo, lower haloalkyl, lower alkoxy, lower hydroxyalkyl or amino;
or a pharmaceutically acceptable salt thereof.

The application provides a method for treating an inflammatory or autoimmune condition comprising administering to a patient in need thereof a therapeutically effective amount of the compound of formula I.

The application provides a pharmaceutical composition comprising the compound of formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R$^1$, R$^2$, or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "----" drawn through a bond each refer to the point of attachment of a functional group or other chemical moiety to the rest of the molecule of which it is a part. Thus, for example:

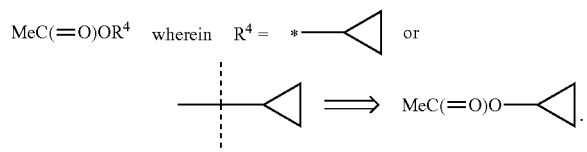

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\rightleftharpoons$ —C(—OH)=CH—), amide/imidic acid (—C(=O)—NH— $\rightleftharpoons$ —C(—OH)=N—) and amidine (—C(=NR)—NH— $\rightleftharpoons$ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl. The term "carbonyl" as used herein means a group of formula C(=O). The term "oxo" as used herein means a group of formula (=O), which may be attached to a carbon atom or heteroatom.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkenyl" refers to a partially unsaturated carbocyclic containing 5 to 7 carbon atoms unless otherwise specified and having a carbon-carbon double bond within the ring. For example, $C_{5-6}$ cycloalkenyl refers to a cycloalkenyl group having from 5 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups may be optionally substituted with one or more substituent. Examples of cycloalkenyl include, but are not limited to, cyclopentenyl and cyclohexenyl.

The term "halogen" or "halo" as used herein means fluorine, chlorine, bromine, or iodine.

The term "amino" as used herein encompasses —NR$_2$, wherein each R group is independently H or lower alky, wherein lower alkyl is as defined herein. Examples of amino groups include dimethyl amino, methyl amino and NH$_2$.

As used herein, the term "aryl" means a monocyclic or bicyclic (also referred to as "biaryl"), substituted or unsubstituted carbocyclic aromatic group. Examples of aryl groups are phenyl, naphthyl and the like.

The term "heteroaryl" as used herein means a monocyclic, or bicyclic ("heterobiaryl"), or tricyclic radical of 5 to 18 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, indolyl oxazolyl, isoxazolyl, thiazolyl, isothiazolyl, triazolinyl, triazolyl, thiophenyl, furanyl, thiadiazolyl, and oxadiaxolinyl which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties, also referred to as "hetero biaryl", include, but are not limited to, quinolinyl, indazolyl, isoquinolinyl, benzofuryl, benzothiophenyl, benzoxazole, benzisoxazole, benzothiazole, pyrrolopyridinyl, pyrrolopyrazinyl, 1H-Pyrrolo[2,3-b]pyridine, and benzisothiazole.

The term "heterocycloalkyl", "heterocyclyl" or "heterocycle" as used herein denotes a monovalent saturated cyclic radical, consisting of one or more rings, preferably one to two rings or three rings, of three to eight atoms per ring, incorporating one or more ring carbon atoms and one or more ring heteroatoms (chosen from N, O or S($=$O)$_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, pyrrolidinyl, morpholinyl, piperazinyl, piperidinyl, isoindolinyl, dihydroisoquinolinyle, tetrahydropyranyl, tetrahydrocarbolinyl, imidazolinyl, thiomorpholinyl, and quinuclidinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Inhibitors of JAK and Syk

The application provides a compound of Formula I

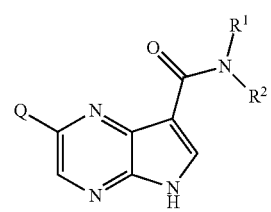

wherein:

$R^1$ is H or OH;

$R^2$ is phenyl, heterocycloalkyl, heteroaryl or cycloalkyl, each optionally substituted with one or more $R^{2'}$;

each $R^{2'}$ is independently hydroxy, halo, oxo, lower alkyl, lower alkenyl, lower alkynyl, lower haloalkyl, lower alkoxy, lower haloalkoxy, lower hydroxyalkyl, amino, lower alkylamino, lower dialkylamino, cyano, lower cyanoalkyl, cycloalkyl, heterocycloalkyl, C($=$O)R$^3$, or S($=$O)$_2$R$^3$;

each $R^3$ is independently OH, cycloalkyl or lower alkyl;

Q is Q$^2$, Q$^3$, or Q$^4$;

Q$^2$ is heterocycloalkyl, cycloalkyl, cycloalkenyl, heterocloalkyl phenyl, heteroaryl, biaryl, or heterobiaryl, optionally substituted with one or more Q$^{2a}$;

Q$^{2a}$ is Q$^{2b}$ or Q$^{2c}$;

Q$^{2b}$ is halogen, oxo, hydroxy, —CN, —SCH$_3$, —S(O)$_2$CH$_3$, or —S($=$O)CH$_3$;

$Q^{2c}$ is $Q^{2d}$ or $Q^{2e}$;
or two $Q^{2a}$ come together to form a bicyclic ring system, optionally substituted with one or more $Q^{2b}$ or $Q^{2c}$;
  $Q^{2d}$ is —O($Q^{2e}$), —S(=O)$_2$($Q^{2e}$), —C(=O)N($Q^{2e}$)$_2$, —S(O)$_2$($Q^{2e}$), —C(=O)($Q^{2e}$), —C(=O)O($Q^{2e}$), —N($Q^{2e}$)C(=O)($Q^{2e}$), —N($Q^{2e}$)C(=O)O($Q^{2e}$), or —N($Q^{2e}$)C(=O)N($Q^{2e}$)$_2$;
    each $Q^{2e}$ is independently H or $Q^{2e'}$;
      each $Q^{2e'}$ is independently lower alkyl, phenyl, benzyl, lower haloalkyl, cycloalkyl, cycloalkenyl, heterocycloalkyl, or heteroaryl, optionally substituted with one or more $Q^{2f}$;
        $Q^{2f}$ is $Q^{2g}$ or $Q^{2h}$,
        $Q^{2g}$ is halogen, hydroxy, cyano, oxo, or —C(=O)($Q^{2h}$);
        $Q^{2h}$ is lower alkyl, lower haloalkyl, lower alkoxy, amino, phenyl, benzyl, cycloalkyl, heterocycloalkyl, or heteroaryl, optionally substituted with one or more $Q^{2i}$;
          $Q^{2i}$ is halogen, hydroxy, cyano, lower alkyl, lower haloalkyl, or lower alkoxy;
$Q^3$ is —O-$Q^{3a}$, —S-$Q^{3a}$, —C(=O)($Q^{3a}$), —O(CH$_2$)$_m$C(=O)($Q^{3a}$), —S(=O)($Q^{3a}$), —S(=O)$_2$($Q^{3a}$), —N($Q^{3a}$)$_2$, —N($Q^{3a}$)S(=O)$_2$($Q^{3a}$), —N($Q^{3a}$)C(=O)($Q^{3a}$), —C(=O)N($Q^{3a}$)$_2$, N($Q^{3a}$)C(=O)N($Q^{3a}$)$_2$ or —N($Q^{3a}$)(CH$_2$)$_m$C(=O)N($Q^{3a}$)$_2$;
  each $Q^{3a}$ is independently $Q^{3b}$ or $Q^{3c}$;
  m is 0, 1, or 2;
    $Q^{3b}$ is H;
    $Q^{3c}$ is lower alkyl, lower haloalkyl, phenyl, cycloalkyl, heterocycloalkyl, or heteroaryl, optionally substituted with one or more $Q^{3d}$;
      each $Q^{3d}$ is independently $Q^{3e}$ or $Q^{3f}$;
        $Q^{3e}$ is halogen or hydroxy;
        $Q^{3f}$ is lower alkyl, lower alkoxy, lower haloalkyl, phenyl, cycloalkyl, heterocycloalkyl, or heteroaryl, optionally substituted with one or more $Q^{3g}$;
        or two $Q^{3f}$ together form a cycloalkyl, heterocycloalkyl, or heteroaryl, optionally substituted with one or more $Q^{3g}$;
          each $Q^{3g}$ is independently halogen, hydroxy, lower alkyl, lower hydroxyalkyl, lower haloalkyl, amido, or lower alkoxy;
$Q^4$ is $Q^{4a}$ or $Q^{4b}$;
  $Q^{4a}$ is hydroxy, halogen, or cyano;
  $Q^{4b}$ is lower alkyl, lower alkoxy, lower alkynyl, lower alkenyl, lower hydroxyalkyl, amino, or lower haloalkyl, optionally substituted with one or more $Q^{4c}$;
    $Q^{4c}$ is $Q^{4d}$ or $Q^{4e}$;
      each $Q^{4d}$ is independently halogen, hydroxy, or cyano;
      each $Q^{4e}$ is independently lower alkyl, lower haloalkyl, lower alkoxy, amino, cycloalkyl, phenyl, heterocycloalkyl, or heteroaryl, optionally substituted with one or more $Q^{4f}$; and
        each $Q^{4f}$ is independently hydroxy, halogen, lower alkyl, lower alkenyl, oxo, lower haloalkyl, lower alkoxy, lower hydroxyalkyl or amino;
or a pharmaceutically acceptable salt thereof.

In one variation of formula I, $R^1$ is H, $R^2$ is phenyl or heterocycloalkyl, each optionally substituted with one or more $R^{2'}$, and Q is cycloalkyl or heteroaryl.

In one variation of formula I, $R^2$ is heterocycloalkyl, $R^{2'}$ is C(=O)$R^3$ or S(=O)$_2R^3$, and $R^3$ is lower alkyl.

In one variation of formula I, $R^1$ is H.

In one variation of formula I, Q is cycloalkyl or heteroaryl, each optionally substituted with one or more $Q^{2a}$.

In one variation of formula I, Q is cycloalkyl or heteroaryl, each optionally substituted with one or more $Q^{2a}$ and $R^1$ is H.

In one variation of formula I, Q is cycloalkyl optionally substituted with one or more $Q^{2a}$.

In one variation of formula I, Q is cycloalkyl optionally substituted with one or more $Q^{2a}$ and $R^1$ is H.

In one variation of formula I, Q is heteroaryl optionally substituted with one or more $Q^{2a}$.

In one variation of formula I, Q is heteroaryl optionally substituted with one or more $Q^{2a}$ and $R^1$ is H.

In one variation of formula I, $R^2$ is phenyl or heterocycloalkyl, each optionally substituted with one or more $R^{2'}$.

In one variation of formula I, $R^2$ is phenyl optionally substituted with one or more $R^{2'}$.

In one variation of formula I, $R^2$ is heterocycloalkyl optionally substituted with one or more $R^{2'}$.

In one variation of formula I, $R^2$ is phenyl optionally substituted with one or more $R^{2'}$ and $R^1$ is H.

In one variation of formula I, $R^2$ is heterocycloalkyl optionally substituted with one or more $R^{2'}$ and $R^1$ is H.

In one variation of formula I, Q is cycloalkyl or heteroaryl, each optionally substituted with one or more $Q^{2a}$, $R^2$ is heterocycloalkyl optionally substituted with one or more $R^{2'}$, and $R^1$ is H.

In one variation of formula I, $R^2$ is heteroaryl or cycloalkyl, each optionally substituted with one or more $R^{2'}$.

In one variation of formula I, $R^2$ is heteroaryl optionally substituted with one or more $R^{2'}$.

In one variation of formula I, $R^2$ is cycloalkyl optionally substituted with one or more $R^{2'}$.

In one variation of formula I, $R^2$ is heteroaryl optionally substituted with one or more $R^{2'}$ and $R^1$ is H.

In one variation of formula I, $R^2$ is cycloalkyl optionally substituted with one or more $R^{2'}$ and $R^1$ is H.

In one variation of formula I, Q is cycloalkyl or heteroaryl, each optionally substituted with one or more $Q^{2a}$, $R^2$ is heteroaryl or cycloalkyl, each optionally substituted with one or more $R^{2'}$, and $R^1$ is H.

In one variation of formula I, $R^{2'}$ is C(=O)$R^3$ or S(=O)$_2R^3$, and $R^3$ is lower alkyl.

In one variation of formula I, $R^{2'}$ is C(=O)$R^3$ and $R^3$ is lower alkyl.

In one variation of formula I, $R^{2'}$ is S(=O)$_2R^3$ and $R^3$ is lower alkyl.

In one variation of formula I, $R^{2'}$ is C(=O)$R^3$ or S(=O)$_2R^3$, $R^3$ is lower alkyl, and $R^1$ is H.

In one variation of formula I, $R^{2'}$ is C(=O)$R^3$, $R^3$ is lower alkyl, and $R^1$ is H.

In one variation of formula I, $R^{2'}$ is S(=O)$_2R^3$, $R^3$ is lower alkyl, and $R^1$ is H.

In one variation of formula I, Q is cycloalkyl or heteroaryl, each optionally substituted with one or more $Q^{2a}$, $R^{2'}$ is C(=O)$R^3$ or S(=O)$_2R^3$, $R^3$ is lower alkyl, and $R^1$ is H.

In one variation of formula I, Q is cycloalkyl or heteroaryl, each optionally substituted with one or more $Q^{2a}$, $R^{2'}$ is C(=O)$R^3$, $R^3$ is lower alkyl, and $R^1$ is H.

In one variation of formula I, Q is cycloalkyl or heteroaryl, each optionally substituted with one or more $Q^{2a}$, $R^{2'}$ is S(=O)$_2R^3$, $R^3$ is lower alkyl, and $R^1$ is H.

The application provides a compound of Formula I'

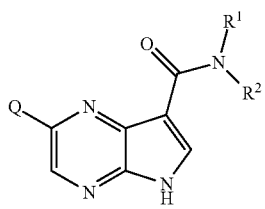

wherein:
R$^1$ is H or OH;
R$^2$ is phenyl, heterocycloalkyl, heteroaryl or cycloalkyl, each optionally substituted with one or more R$^{2'}$;
  each R$^{2'}$ is independently hydroxy, halo, oxo, lower alkyl, lower alkenyl, lower alkynyl, lower haloalkyl, lower alkoxy, lower haloalkoxy, lower hydroxyalkyl, amino, lower alkylamino, lower dialkylamino, cyano, cycloalkyl, heterocycloalkyl, C(=O)R$^3$, or S(=O)$_2$R$^3$;
  each R$^3$ is independently OH or lower alkyl;
Q is Q$^2$, Q$^3$, or Q$^4$;
Q$^2$ is heterocycloalkyl, cycloalkyl, cycloalkenyl, heterocycloalkyl phenyl, heteroaryl, biaryl, or heterobiaryl, optionally substituted with one or more Q$^{2a}$;
  Q$^{2a}$ is Q$^{2b}$ or Q$^{2c}$;
    Q$^{2b}$ is halogen, oxo, hydroxy, —CN, —SCH$_3$, —S(O)$_2$CH$_3$, or —S(=O)CH$_3$;
    Q$^{2c}$ is Q$^{2d}$ or Q$^{2e}$;
    or two Q$^{2a}$ come together to form a bicyclic ring system, optionally substituted with one or more Q$^{2b}$ or Q$^{2c}$;
    Q$^{2d}$ is —O(Q$^{2e}$), —S(=O)$_2$(Q$^{2e}$), —C(=O)N(Q$^{2e}$)$_2$, —S(O)$_2$(Q$^{2e}$), —C(=O)(Q$^{2e}$), —C(=O)O(Q$^{2e}$), —N(Q$^{2e}$)C(=O)(Q$^{2e}$), —N(Q$^{2e}$)C(=O)O(Q$^{2e}$), or —N(Q$^{2e}$)C(=O)N(Q$^{2e}$)$_2$;
      each Q$^{2e}$ is independently H or Q$^{2e'}$;
      each Q$^{2e'}$ is independently lower alkyl, phenyl, benzyl, lower haloalkyl, cycloalkyl, cycloalkenyl, heterocycloalkyl, or heteroaryl, optionally substituted with one or more Q$^{2f}$;
      Q$^{2f}$ is Q$^{2g}$ or Q$^{2h}$;
      Q$^{2g}$ is halogen, hydroxy, cyano, oxo, or —C(=O)(Q$^{2h}$);
      Q$^{2h}$ is lower alkyl, lower haloalkyl, lower alkoxy, amino, phenyl, benzyl, cycloalkyl, heterocycloalkyl, or heteroaryl, optionally substituted with one or more Q$^{2i}$; and
      Q$^{2i}$ is halogen, hydroxy, cyano, lower alkyl, lower haloalkyl, or lower alkoxy;
Q$^3$ is —O-Q$^{3a}$, —S-Q$^{3a}$, —C(=O)(Q$^{3a}$), —O(CH$_2$)$_m$C(=O)(Q$^{3a}$), —S(=O)(Q$^{3a}$), —S(=O)$_2$(Q$^{3a}$), —N(Q$^{3a}$)$_2$, —N(Q$^{3a}$)S(=O)$_2$(Q$^{3a}$), —N(Q$^{3a}$)C(=O)(Q$^{3a}$), —C(=O)N(Q$^{3a}$)$_2$, N(Q$^{3a}$)C(=O)N(Q$^{3a}$)$_2$ or —N(Q$^{3a}$)(CH$_2$)$_m$C(=O)N(Q$^{3a}$)$_2$;
  each Q$^{3a}$ is independently Q$^{3b}$ or Q$^{3c}$;
  m is 0, 1, or 2;
  Q$^{3b}$ is H;
  Q$^{3c}$ is lower alkyl, lower haloalkyl, phenyl, cycloalkyl, heterocycloalkyl, or heteroaryl, optionally substituted with one or more Q$^{3d}$; and
    each Q$^{3d}$ is independently Q$^{3d}$ is Q$^{3e}$ or Q$^{3f}$;
    Q$^{3e}$ is halogen or hydroxy;
    Q$^{3f}$ is lower alkyl, lower alkoxy, lower haloalkyl, phenyl, cycloalkyl, heterocycloalkyl, or heteroaryl, optionally substituted with one or more Q$^{3g}$; and
      each Q$^{3g}$ is independently halogen, hydroxy, lower alkyl, lower hydroxyalkyl, lower haloalkyl, or lower alkoxy;
Q$^4$ is Q$^{4a}$ Q$^{4b}$;
  Q$^{4a}$ is hydroxy, halogen, or cyano;
  Q$^{4b}$ is lower alkyl, lower alkoxy, lower alkynyl, lower alkenyl, lower hydroxyalkyl, amino, or lower haloalkyl, optionally substituted with one or more Q$^{4e}$;
  Q$^{4c}$ is Q$^{4d}$ or Q$^{4e}$
    each Q$^{4d}$ is independently halogen, hydroxy, or cyano;
    each Q$^{4e}$ is independently lower alkyl, lower haloalkyl, lower alkoxy, amino, cycloalkyl, phenyl, heterocycloalkyl, or heteroaryl, optionally substituted with one or more Q$^{4f}$;
    each Q$^{4f}$ is independently hydroxy, halogen, lower alkyl, lower alkenyl, oxo, lower haloalkyl, lower alkoxy, lower hydroxyalkyl or amino;
or a pharmaceutically acceptable salt thereof.

The application provides a compound selected from the group consisting of:

2-Cyclopropyl-5H-pyrrolo[2,3-b]pyrazine-7-carboxylic acid (tetrahydro-pyran-4-yl)-amide;
2-Cyclopropyl-5H-pyrrolo[2,3-b]pyrazine-7-carboxylic acid (4-hydroxymethyl-tetrahydro-pyran-4-yl)-amide;
2-Cyclopropyl-5H-pyrrolo[2,3-b]pyrazine-7-carboxylic acid (1-hydroxymethyl-cyclopentyl)-amide;
2-Cyclopropyl-5H-pyrrolo[2,3-b]pyrazine-7-carboxylic acid (2,2-dimethyl-tetrahydro-furan-3-yl)-amide;
2-Cyclopropyl-5H-pyrrolo[2,3-b]pyrazine-7-carboxylic acid (3-cyano-phenyl)-amide;
2-Cyclopropyl-5H-pyrrolo[2,3-b]pyrazine-7-carboxylic acid (tetrahydro-pyran-3-yl)-amide;
2-Cyclopropyl-5H-pyrrolo[2,3-b]pyrazine-7-carboxylic acid (2,2-dimethyl-cyclopentyl)-amide;
2-Cyclopropyl-5H-pyrrolo[2,3-b]pyrazine-7-carboxylic acid (3-trifluoromethyl-phenyl)-amide;
2-Cyclopropyl-5H-pyrrolo[2,3-b]pyrazine-7-carboxylic acid (5-cyano-2-methyl-phenyl)-amide;
2-Cyclopropyl-5H-pyrrolo[2,3-b]pyrazine-7-carboxylic acid (1-cyano-cyclopropyl)-amide;
2-Cyclopropyl-5H-pyrrolo[2,3-b]pyrazine-7-carboxylic acid ((trans)-2-hydroxy-2-methyl-cyclopentyl)-amide;

2-Cyclopropyl-5H-pyrrolo[2,3-b]pyrazine-7-carboxylic acid [1-(1-hydroxy-1-methyl-ethyl)-cyclopentyl]-amide;
2-Cyclopropyl-5H-pyrrolo[2,3-b]pyrazine-7-carboxylic acid [1-(1-hydroxy-1-methyl-ethyl)-cyclobutyl]-amide;
2-Cyclopropyl-5H-pyrrolo[2,3-b]pyrazine-7-carboxylic acid [1-(1-hydroxy-1-methyl-ethyl)-cyclohexyl]-amide;
2-Cyclopropyl-5H-pyrrolo[2,3-b]pyrazine-7-carboxylic acid ((3R,4S)-3-hydroxy-tetrahydro-pyran-4-yl)-amide;
2-Cyclopropyl-5H-pyrrolo[2,3-b]pyrazine-7-carboxylic acid (4,4-dimethyl-tetrahydro-furan-3-yl)-amide;
2-Cyclopropyl-5H-pyrrolo[2,3-b]pyrazine-7-carboxylic acid [3-(1-hydroxy-1-methyl-ethyl)-pyrrolidin-3-yl]-amide;
2-Cyclopropyl-5H-pyrrolo[2,3-b]pyrazine-7-carboxylic acid [3-(1-hydroxy-1-methyl-ethyl)-tetrahydro-furan-3-yl]-amide;
2-Cyclopropyl-5H-pyrrolo[2,3-b]pyrazine-7-carboxylic acid (1-cyclopropanecarbonyl-cyclopentyl)-amide;
2-Cyclopropyl-5H-pyrrolo[2,3-b]pyrazine-7-carboxylic acid (1-methanesulfonyl-pyrrolidin-3-yl)-amide;
2-Cyclopropyl-5H-pyrrolo[2,3-b]pyrazine-7-carboxylic acid (1-methanesulfonyl-piperidin-4-yl)-amide;
2-Cyclopropyl-5H-pyrrolo[2,3-b]pyrazine-7-carboxylic acid cyclohexylamide;
2-Cyclopropyl-5H-pyrrolo[2,3-b]pyrazine-7-carboxylic acid cyclopentylamide;
2-Cyclopropyl-5H-pyrrolo[2,3-b]pyrazine-7-carboxylic acid (1-methanesulfonyl-piperidin-3-yl)-amide;
2-Cyclopropyl-5H-pyrrolo[2,3-b]pyrazine-7-carboxylic acid ((cis)-2-cyano-cyclopentyl)-amide;
2-Cyclopropyl-5H-pyrrolo[2,3-b]pyrazine-7-carboxylic acid (1-cyanomethyl-cyclopentyl)-amide;
2-Cyclopropyl-5H-pyrrolo[2,3-b]pyrazine-7-carboxylic acid (1-ethanesulfonyl-piperidin-3-yl)-amide;
2-Cyclopropyl-5H-pyrrolo[2,3-b]pyrazine-7-carboxylic acid [1-(propane-1-sulfonyl)-piperidin-3-yl]-amide;
2-Cyclopropyl-5H-pyrrolo[2,3-b]pyrazine-7-carboxylic acid [1-(propane-2-sulfonyl)-piperidin-3-yl]-amide;
2-Cyclopropyl-5H-pyrrolo[2,3-b]pyrazine-7-carboxylic acid ((S)-1-methanesulfonyl-piperidin-3-yl)-amide;
2-Cyclopropyl-5H-pyrrolo[2,3-b]pyrazine-7-carboxylic acid ((R)-1-methanesulfonyl-piperidin-3-yl)-amide;
2-Cyclopropyl-5H-pyrrolo[2,3-b]pyrazine-7-carboxylic acid (2,2-dimethyl-cyclohexyl)-amide;
2-Phenoxy-5H-pyrrolo[2,3-b]pyrazine-7-carboxylic acid cyclohexylamide;
2-(2,4-Difluoro-phenoxy)-5H-pyrrolo[2,3-b]pyrazine-7-carboxylic acid cyclohexylamide;
2-Cyclopropyl-5H-pyrrolo[2,3-b]pyrazine-7-carboxylic acid (1-methanesulfonyl-4,4-dimethyl-piperidin-3-yl)-amide;
2-Cyclopropyl-5H-pyrrolo[2,3-b]pyrazine-7-carboxylic acid (1-acetyl-piperidin-4-yl)-amide;
2-Cyclopropyl-5H-pyrrolo[2,3-b]pyrazine-7-carboxylic acid (1-acetyl-pyrrolidin-3-yl)-amide;
2-Cyclopropyl-5H-pyrrolo[2,3-b]pyrazine-7-carboxylic acid (1-acetyl-piperidin-3-yl)-amide;
2-(1-Ethyl-1H-pyrazol-4-yl)-5H-pyrrolo[2,3-b]pyrazine-7-carboxylic acid (2,2-dimethyl-cyclohexyl)-amide;
2-((R)-3-Acetylamino-indan-5-yloxy)-5H-pyrrolo[2,3-b]pyrazine-7-carboxylic acid cyclohexylamide; and
2-((R)-3-Acetylamino-indan-5-yloxy)-5H-pyrrolo[2,3-b]pyrazine-7-carboxylic acid (1,1-dioxo-hexahydro-1λ6-thiopyran-4-yl)-amide.

The application provides a method for treating an inflammatory or autoimmune condition comprising administering to a patient in need thereof a therapeutically effective amount of the compound of formula I or I'.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of formula I or I'.

The application provides a method for treating rheumatoid arthritis comprising administering to a patient in need thereof a therapeutically effective amount of the compound of Formula I or I'.

The application provides a method for treating asthma comprising administering to a patient in need thereof a therapeutically effective amount of the compound of Formula I or I'.

The application provides a method for inhibiting T-cell proliferative disorder comprising administering to a patient in need thereof a therapeutically effective amount of the compound of formula I or I'.

The application provides a method for inhibiting T-cell proliferative disorder comprising administering to a patient in need thereof a therapeutically effective amount of the compound of formula I or I'.

The application provides the above method, wherein the proliferative disorder is cancer.

The application provides a method for treating a B-cell proliferative disorder comprising administering to a patient in need thereof a therapeutically effective amount of the compound of formula I or I'.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of formula I or I'.

The application provides a method for preventing or treating all forms of organ rejection, including acute allograft or xenograft rejection and chronic allograft or xenograft rejection, of vascularized or non-vascularized transplants, comprising administering to a patient in need thereof the compound of formula I or I'.

The application provides a method for inhibiting JAK3 activity comprising administering the compound of formula I or I', wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

The application provides a method for inhibiting SYK activity comprising administering the compound of formula I or I', wherein the compound exhibits an $IC_{50}$ of 50 micromolar or less in an in vitro biochemical assay of SYK activity.

The application provides the above method, wherein the compound exhibits an $IC_{50}$ of 100 nanomolar or less in an in vitro biochemical assay of SYK activity.

The application provides the above method, wherein the compound exhibits an $IC_{50}$ of 10 nanomolar or less in an in vitro biochemical assay of SYK activity.

The application provides a method for treating an inflammatory condition comprising co-administering to a patient in need thereof a therapeutically effective amount of an anti-inflammatory compound in combination with the compound of formula I or I'.

The application provides a method for treating an immune disorder comprising co-administering to a patient in need thereof a therapeutically effective amount of an immunosuppressant compound in combination with the compound of formula I or I'.

The application provides a pharmaceutical composition comprising the compound of formula I or I', admixed with at least one pharmaceutically acceptable carrier, excipient or diluent.

The application provides the above pharmaceutical compound of formula I or I', further comprising an additional therapeutic agent selected from a chemotherapeutic or antiproliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a use of the compound of formula I or I' in the manufacture of a medicament for the treatment of an inflammatory disorder.

The application provides a use of the compound of formula I or I' in the manufacture of a medicament for the treatment of an autoimmune disorder.

The application provides a compound or method as described herein.

COMPOUNDS AND PREPARATION

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| # | STRUCTURE | SYSTEMATIC NAME | MP |
|---|---|---|---|
| I-1 | 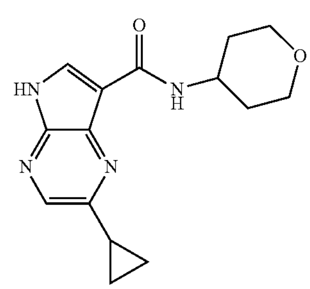 | 2-Cyclopropyl-5H-pyrrolo[2,3-b]pyrazine-7-carboxylic acid (tetrahydro-pyran-4-yl)-amide | >300- |

TABLE I-continued

| # | STRUCTURE | SYSTEMATIC NAME | MP |
|---|---|---|---|
| I-2 | 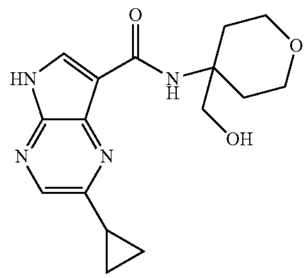 | 2-Cyclopropyl-5H-pyrrolo[2,3-b]pyrazine-7-carboxylic acid (4-hydroxymethyl-tetrahydro-pyran-4-yl)-amide | 294.0-296.0 |
| I-3 | 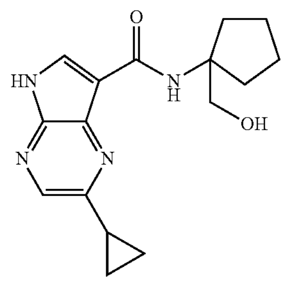 | 2-Cyclopropyl-5H-pyrrolo[2,3-b]pyrazine-7-carboxylic acid (1-hydroxymethyl-cyclopentyl)-amide | 272.0-274.0 |
| I-4 | 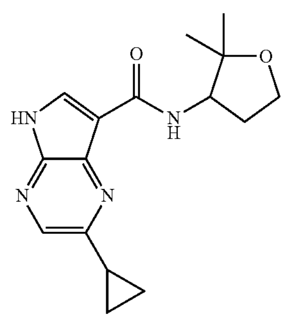 | 2-Cyclopropyl-5H-pyrrolo[2,3-b]pyrazine-7-carboxylic acid (2,2-dimethyl-tetrahydro-furan-3-yl)-amide | >300- |
| I-5 | 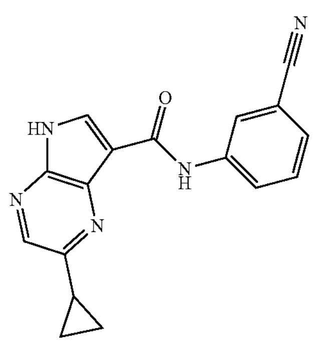 | 2-Cyclopropyl-5H-pyrrolo[2,3-b]pyrazine-7-carboxylic acid (3-cyano-phenyl)-amide | 272.0-274.0 |
| I-6 | 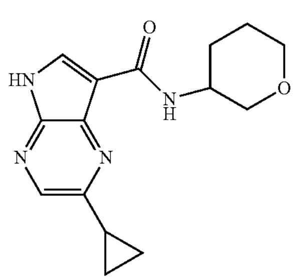 | 2-Cyclopropyl-5H-pyrrolo[2,3-b]pyrazine-7-carboxylic acid (tetrahydro-pyran-3-yl)-amide | >300- |

TABLE I-continued

| # | STRUCTURE | SYSTEMATIC NAME | MP |
|---|-----------|-----------------|-----|
| I-7 | 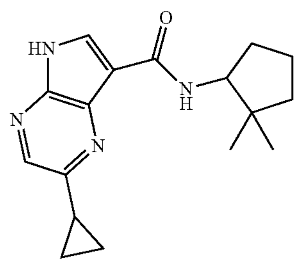 | 2-Cyclopropyl-5H-pyrrolo[2,3-b]pyrazine-7-carboxylic acid (2,2-dimethyl-cyclopentyl)-amide | >300- |
| I-8 | 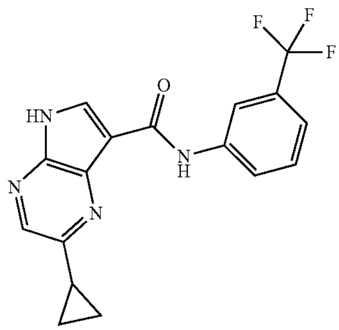 | 2-Cyclopropyl-5H-pyrrolo[2,3-b]pyrazine-7-carboxylic acid (3-trifluoromethyl-phenyl)-amide | 271.1-272.9 |
| I-9 | 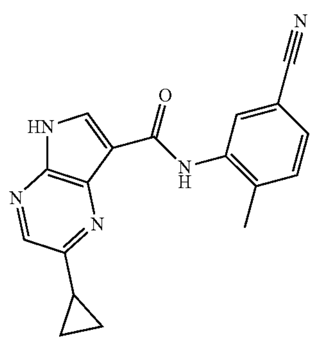 | 2-Cyclopropyl-5H-pyrrolo[2,3-b]pyrazine-7-carboxylic acid (5-cyano-2-methyl-phenyl)-amide | 280-284 |
| I-10 | 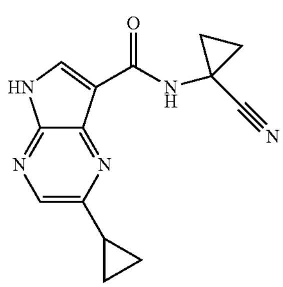 | 2-Cyclopropyl-5H-pyrrolo[2,3-b]pyrazine-7-carboxylic acid (1-cyano-cyclopropyl)-amide | >300- |
| I-11 | 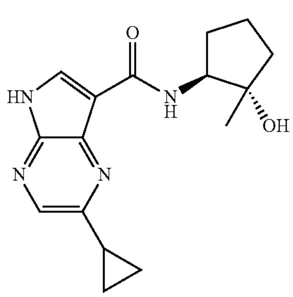 | 2-Cyclopropyl-5H-pyrrolo[2,3-b]pyrazine-7-carboxylic acid ((trans)-2-hydroxy-2-methyl-cyclopentyl)-amide | 260.0-262.0 |

TABLE I-continued

| # | STRUCTURE | SYSTEMATIC NAME | MP |
|---|---|---|---|
| I-12 | 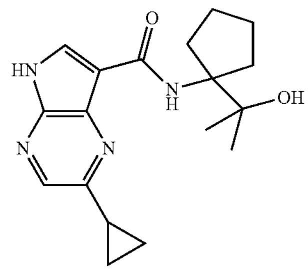 | 2-Cyclopropyl-5H-pyrrolo[2,3-b]pyrazine-7-carboxylic acid [1-(1-hydroxy-1-methyl-ethyl)-cyclopentyl]-amide | 232.0-234.0 |
| I-13 | 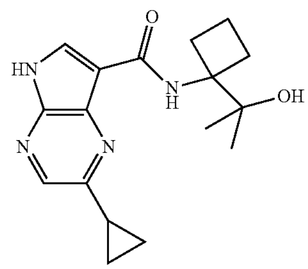 | 2-Cyclopropyl-5H-pyrrolo[2,3-b]pyrazine-7-carboxylic acid [1-(1-hydroxy-1-methyl-ethyl)-cyclobutyl]-amide | 264.0-266.0 |
| I-14 | 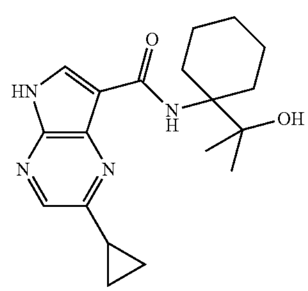 | 2-Cyclopropyl-5H-pyrrolo[2,3-b]pyrazine-7-carboxylic acid [1-(1-hydroxy-1-methyl-ethyl)-cyclohexyl]-amide | 228.0-230.0 |
| I-15 | 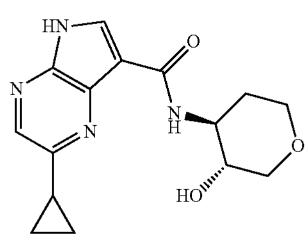 | 2-Cyclopropyl-5H-pyrrolo[2,3-b]pyrazine-7-carboxylic acid ((3R,4S)-3-hydroxy-tetrahydro-pyran-4-yl)-amide | |
| I-16 | 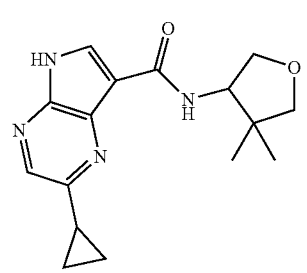 | 2-Cyclopropyl-5H-pyrrolo[2,3-b]pyrazine-7-carboxylic acid (4,4-dimethyl-tetrahydro-furan-3-yl)-amide | >300- |

TABLE I-continued

| # | STRUCTURE | SYSTEMATIC NAME | MP |
|---|---|---|---|
| I-17 | 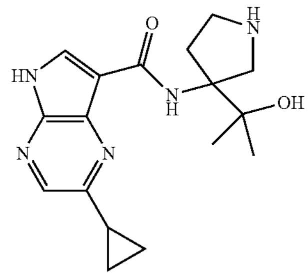 | 2-Cyclopropyl-5H-pyrrolo[2,3-b]pyrazine-7-carboxylic acid [3-(1-hydroxy-1-methyl-ethyl)-pyrrolidin-3-yl]-amide | 200.0-203.0 |
| I-18 | 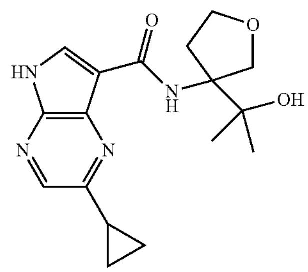 | 2-Cyclopropyl-5H-pyrrolo[2,3-b]pyrazine-7-carboxylic acid [3-(1-hydroxy-1-methyl-ethyl)-tetrahydro-furan-3-yl]-amide | 213.0-215.0 |
| I-19 | 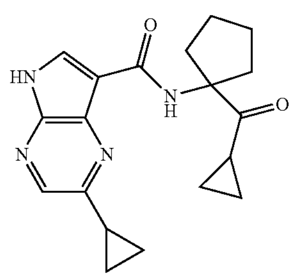 | 2-Cyclopropyl-5H-pyrrolo[2,3-b]pyrazine-7-carboxylic acid (1-cyclopropanecarbonyl-cyclopentyl)-amide | 296.0-299.0 |
| I-20 | 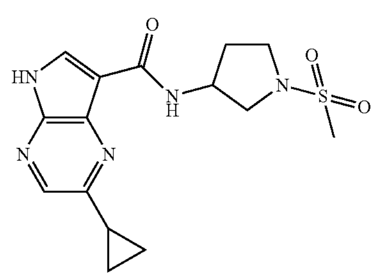 | 2-Cyclopropyl-5H-pyrrolo[2,3-b]pyrazine-7-carboxylic acid (1-methanesulfonyl-pyrrolidin-3-yl)-amide | >300- |
| I-21 | 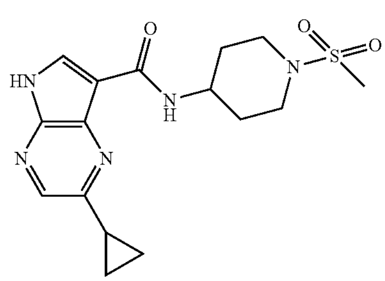 | 2-Cyclopropyl-5H-pyrrolo[2,3-b]pyrazine-7-carboxylic acid (1-methanesulfonyl-piperidin-4-yl)-amide | 278.0-280.0 |

TABLE I-continued

| # | STRUCTURE | SYSTEMATIC NAME | MP |
|---|---|---|---|
| I-22 | 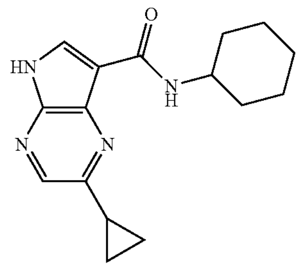 | 2-Cyclopropyl-5H-pyrrolo[2,3-b]pyrazine-7-carboxylic acid cyclohexylamide | >300 |
| I-23 | 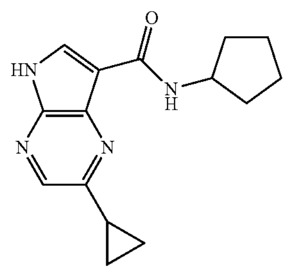 | 2-Cyclopropyl-5H-pyrrolo[2,3-b]pyrazine-7-carboxylic acid cyclopentylamide | >300° C. |
| I-24 | 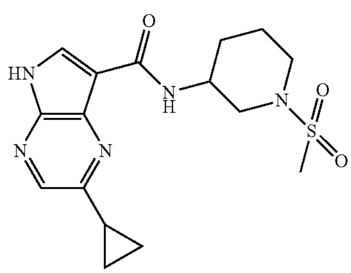 | 2-Cyclopropyl-5H-pyrrolo[2,3-b]pyrazine-7-carboxylic acid (1-methanesulfonyl-piperidin-3-yl)-amide | 284.0-287.0 |
| I-25 | 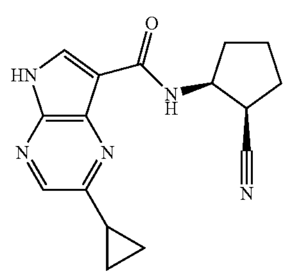 | 2-Cyclopropyl-5H-pyrrolo[2,3-b]pyrazine-7-carboxylic acid ((cis)-2-cyano-cyclopentyl)-amide | >300 |
| I-26 | 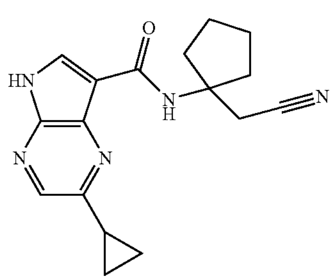 | 2-Cyclopropyl-5H-pyrrolo[2,3-b]pyrazine-7-carboxylic acid (1-cyanomethyl-cyclopentyl)-amide | 280.0-281.1 |

TABLE I-continued

| # | STRUCTURE | SYSTEMATIC NAME | MP |
|---|---|---|---|
| I-27 | 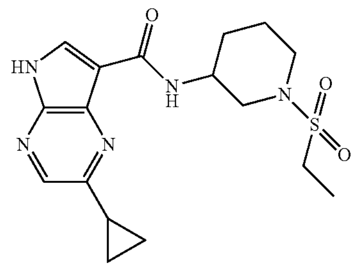 | 2-Cyclopropyl-5H-pyrrolo[2,3-b]pyrazine-7-carboxylic acid (1-ethanesulfonyl-piperidin-3-yl)-amide | 266.0-269.0 |
| I-28 | 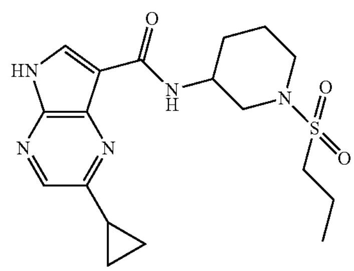 | 2-Cyclopropyl-5H-pyrrolo[2,3-b]pyrazine-7-carboxylic acid [1-(propane-1-sulfonyl)-piperidin-3-yl]-amide | 228.0-230.0 |
| I-29 | 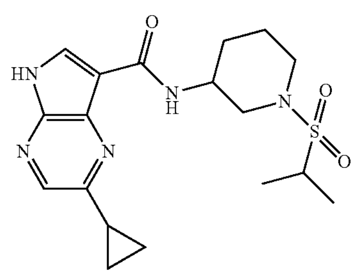 | 2-Cyclopropyl-5H-pyrrolo[2,3-b]pyrazine-7-carboxylic acid [1-(propane-2-sulfonyl)-piperidin-3-yl]-amide | 255.0-258.0 |
| I-30 | 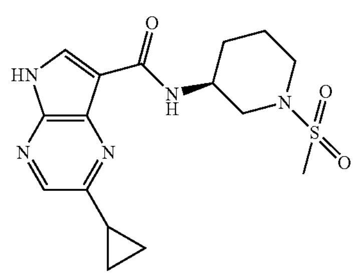 | 2-Cyclopropyl-5H-pyrrolo[2,3-b]pyrazine-7-carboxylic acid ((S)-1-methanesulfonyl-piperidin-3-yl)-amide | 278.0-281.0 |
| I-31 | 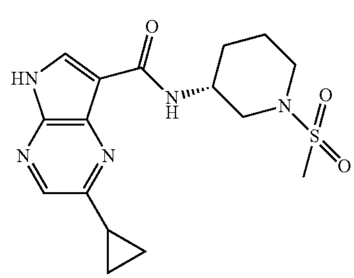 | 2-Cyclopropyl-5H-pyrrolo[2,3-b]pyrazine-7-carboxylic acid ((R)-1-methanesulfonyl-piperidin-3-yl)-amide | 277.0-280.0 |

TABLE I-continued

| # | STRUCTURE | SYSTEMATIC NAME | MP |
|---|---|---|---|
| I-32 | 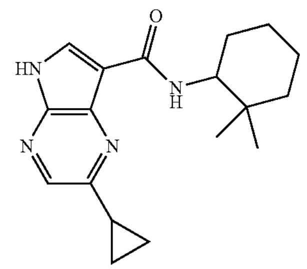 | 2-Cyclopropyl-5H-pyrrolo[2,3-b]pyrazine-7-carboxylic acid (2,2-dimethyl-cyclohexyl)-amide | 295.0-297.0 |
| I-33 | 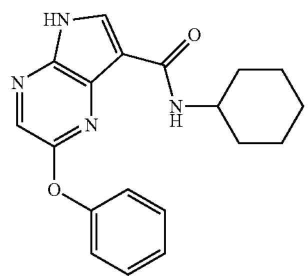 | 2-Phenoxy-5H-pyrrolo[2,3-b]pyrazine-7-carboxylic acid cyclohexylamide | 255-257 |
| I-34 | 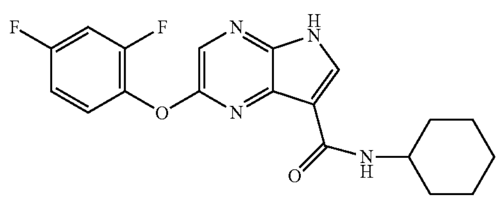 | 2-(2,4-Difluoro-phenoxy)-5H-pyrrolo[2,3-b]pyrazine-7-carboxylic acid cyclohexylamide | 245.0-247.0 |
| I-35 | 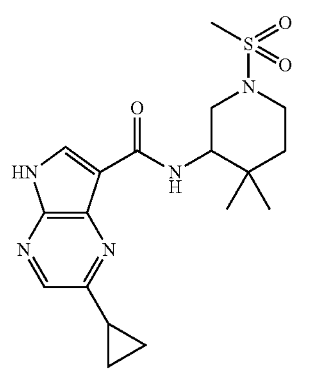 | 2-Cyclopropyl-5H-pyrrolo[2,3-b]pyrazine-7-carboxylic acid (1-methanesulfonyl-4,4-dimethyl-piperidin-3-yl)-amide | |
| I-36 | 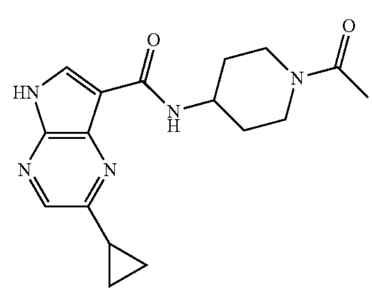 | 2-Cyclopropyl-5H-pyrrolo[2,3-b]pyrazine-7-carboxylic acid (1-acetyl-piperidin-4-yl)-amide | 273.0-275.0 |

TABLE I-continued

| # | STRUCTURE | SYSTEMATIC NAME | MP |
|---|---|---|---|
| I-37 | 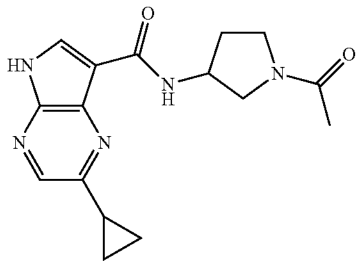 | 2-Cyclopropyl-5H-pyrrolo[2,3-b]pyrazine-7-carboxylic acid (1-acetyl-pyrrolidin-3-yl)-amide | 242.0-245.0 |
| I-38 | 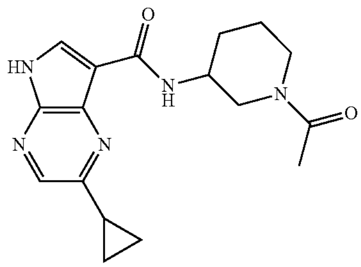 | 2-Cyclopropyl-5H-pyrrolo[2,3-b]pyrazine-7-carboxylic acid (1-acetyl-piperidin-3-yl)-amide | 215.0-218.0 |
| I-39 | 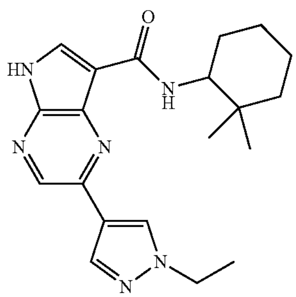 | 2-(1-Ethyl-1H-pyrazol-4-yl)-5H-pyrrolo[2,3-b]pyrazine-7-carboxylic acid (2,2-dimethyl-cyclohexyl)-amide | |
| I-40 | 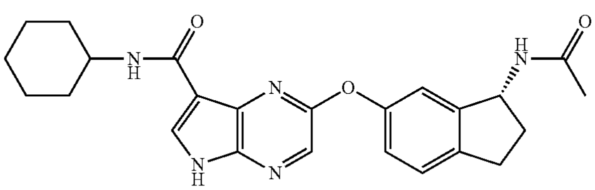 | 2-((R)-3-Acetylamino-indan-5-yloxy)-5H-pyrrolo[2,3-b]pyrazine-7-carboxylic acid cyclohexylamide | |
| I-41 | 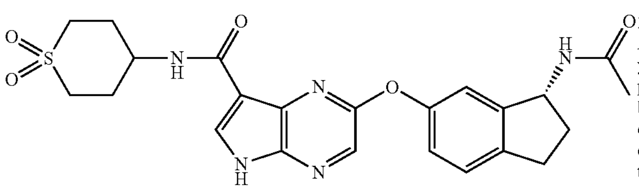 | 2-((R)-3-Acetylamino-indan-5-yloxy)-5H-pyrrolo[2,3-b]pyrazine-7-carboxylic acid (1,1-dioxo-hexahydro-1λ6-thiopyran-4-yl)-amide | |

The following Scheme, Preparations, and Examples illustrate the preparation and biological evaluation of compounds within the scope of the invention. These preparations and examples which follow are provided to enable those skilled in the art to more clearly understand and to practice the present invention. They should not be considered as limiting the scope of the invention, but merely as being illustrative and representative thereof.

Synthesis

Incorporation of a variety of moieties on pyrrolopyrazines is disclosed in U.S. application Ser. No. 12/378,837, filed on Feb. 20, 2009, Ser. No. 12/378,869, filed on Feb. 20, 2009, Ser. No. 12/378,971, filed on Feb. 20, 2009, Ser. No. 12/378,977, filed on Feb. 20, 2009, and Ser. No. 12/378,978, filed on Feb. 20, 2009, each of which is expressly incorporated herein by reference.

In particular, the synthetic disclosures in the aforementioned applications, as well as that presented in Scheme 1, and those of the Procedures and the Examples presented below, describe synthetic details to enable the incorporation of the variety of moieties included in the below generic structure Formula I at position Q:

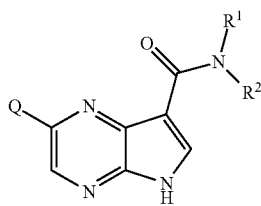

For example, U.S. application Ser. No. 12/378,837 discloses pyrrolopyrazine compounds wherein Q can be H, hydroxy, cyano, or halogen; or lower alkyl, lower alkenyl, lower alkynyl, lower hydroxyalkyl, amino, or lower haloalkyl, each optionally substituted.

For example, U.S. application Ser. No. 12/378,869 discloses pyrrolopyrazine compounds wherein Q can be phenyl substituted with two substitutents which come together to form a heterocyclic or heteroaryl ring system, each optionally substituted.

For example, U.S. application Ser. No. 12/378,971 discloses pyrrolopyrazine compounds wherein Q can be —O-$Q^{3a}$, —S-$Q^{3a}$, —C(=O)($Q^{3a}$), —O(CH$_2$)$_m$C(=O)($Q^{3a}$), —S(=O)($Q^{3a}$), —S(=O)$_2$($Q^{3a}$), —N($Q^{3a}$)$_2$, —N($Q^{3a}$)S(=O)$_2$($Q^{3a}$), —N($Q^{3a}$)C(=O)($Q^{3a}$), —C(=O)N($Q^{3a}$)$_2$, or —N($Q^{3a}$)C(=O)N($Q^{3a}$)$_2$, wherein m is 0, 1, or 2 and each $Q^{3a}$ independently can be lower alkyl, lower haloalkyl, phenyl, cycloalkyl, heterocycloalkyl, or heteroaryl, each optionally substituted, or H.

For example, U.S. application Ser. No. 12/378,977 discloses pyrrolopyrazine compounds wherein Q can be phenyl or indolyl, each optionally substituted.

For example, U.S. application Ser. No. 12/378,978 pyrrolopyrazine compounds wherein Q can be cycloalkyl, cycloalkenyl, heterocycloalkyl, or heteroaryl, each optionally substituted.

The synthetic details in Scheme 1, as well as those of the Procedures and the Examples presented below, describe the synthetic preparations enabling the incorporation of moieties included in the above generic structure at positions $R^1$ and $R^2$.

A representative method for the preparation of the compounds of the present invention is outlined in Scheme 1 below:

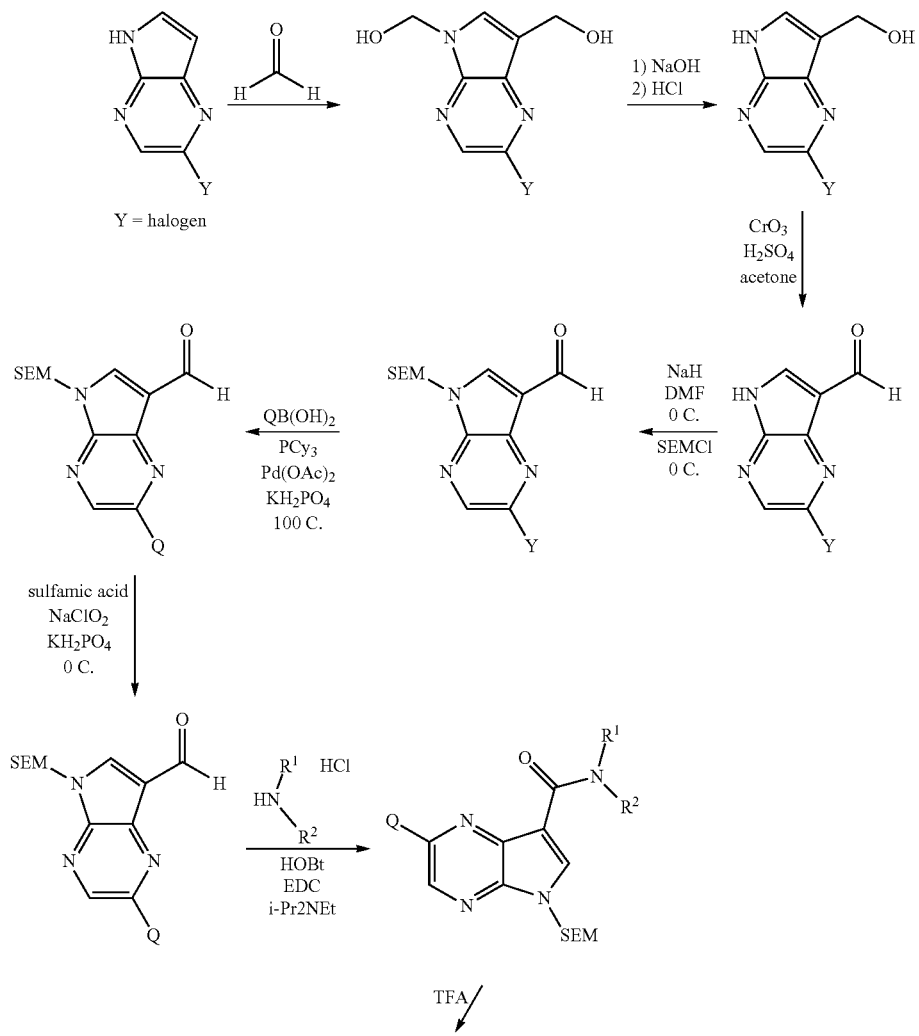

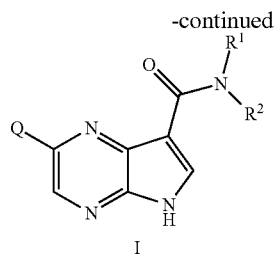

I

In Scheme 1 above, $R^1$ can be H or OH; $R^2$ can be phenyl, heterocycloalkyl, heteroaryl or cycloalkyl, each optionally substituted with one or more $R^{2'}$; each $R^{2'}$ can be independently hydroxy, halo, oxo, lower alkyl, lower alkenyl, lower alkynyl, lower haloalkyl, lower alkoxy, lower haloalkoxy, lower hydroxyalkyl, amino, lower alkylamino, lower dialkylamino, cyano, cycloalkyl, heterocycloalkyl, C(=O)$R^3$, or S(=O)$_2R^3$; each $R^3$ can be independently OH or lower alkyl; Q can be $Q^2$, $Q^3$, or $Q^4$; $Q^2$ can be heterocycloalkyl, cycloalkyl, cycloalkenyl, heterocycloalkyl phenyl, heteroaryl, biaryl, or heterobiaryl, optionally substituted with one or more $Q^{2a}$, $Q^{2a}$ can be $Q^{2b}$ or $Q^{2c}$; $Q^{2b}$ can be halogen, oxo, hydroxy, —CN, —SCH$_3$, —S(O)$_2$CH$_3$, or —S(=O)CH$_3$; $Q^{2c}$ can be $Q^{2d}$ or $Q^{2e}$; or two $Q^{2a}$ come together to form a bicyclic ring system, optionally substituted with one or more $Q^{2b}$ or $Q^{2c}$; $Q^{2d}$ can be —O($Q^{2e}$), —S(=O)$_2$($Q^{2e}$), —C(=O)N($Q^{2e}$)$_2$, —S(O)$_2$($Q^{2e}$), —C(=O)O($Q^{2e}$), —N($Q^{2e}$)C(=O)($Q^{2e}$), —N($Q^{2e}$)C(=O)O($Q^{2e}$), or —N($Q^{2e}$)C(=O)N($Q^{2e}$)$_2$; each $Q^{2e}$ can be independently H or $Q^{2e'}$; each $Q^{2e'}$ can be independently lower alkyl, phenyl, benzyl, lower haloalkyl, cycloalkyl, cycloalkenyl, heterocycloalkyl, or heteroaryl, optionally substituted with one or more $Q^{2f}$; $Q^{2f}$ can be $Q^{2g}$ or $Q^{2h}$; $Q^{2g}$ can be halogen, hydroxy, cyano, oxo, or —C(=O)($Q^{2h}$); $Q^{2h}$ can be lower alkyl, lower haloalkyl, lower alkoxy, amino, phenyl, benzyl, cycloalkyl, heterocycloalkyl, or heteroaryl, optionally substituted with one or more $Q^{2i}$; and $Q^{2i}$ can be halogen, hydroxy, cyano, lower alkyl, lower haloalkyl, or lower alkoxy; $Q^3$ can be —O-$Q^{3a}$, —S-$Q^{3a}$, —C(=O)($Q^{3a}$), —O(CH$_2$)$_m$C(=O)($Q^{3a}$), —S(=O)($Q^{3a}$), —S(=O)$_2$($Q^{3a}$), —N($Q^{3a}$)$_2$, —N($Q^{3a}$)S(=O)$_2$($Q^{3a}$), N($Q^{3a}$)C(=O)($Q^{3a}$), —C(=O)N($Q^{3a}$)$_2$, N($Q^{3a}$)C(=O)N($Q^{3a}$)$_2$ or —N($Q^{3a}$)(CH$_2$)$_m$C(=O)N($Q^{3a}$)$_2$; each $Q^{3a}$ can be independently $Q^{3b}$ or $Q^{3c}$; m can be 0, 1, or 2; $Q^{3b}$ can be H; $Q^{3c}$ can be lower alkyl, lower haloalkyl, phenyl, cycloalkyl, heterocycloalkyl, or heteroaryl, optionally substituted with one or more $Q^{3d}$; and each $Q^{3d}$ can be independently $Q^{3d}$ can be $Q^{3e}$ or $Q^{3f}$; $Q^{3e}$ can be halogen or hydroxy; $Q^{3f}$ can be lower alkyl, lower alkoxy, lower haloalkyl, phenyl, cycloalkyl, heterocycloalkyl, or heteroaryl, optionally substituted with one or more $Q^{3g}$; and each $Q^{3g}$ can be independently halogen, hydroxy, lower alkyl, lower hydroxyalkyl, lower haloalkyl, or lower alkoxy; $Q^4$ can be $Q^{4a}$ or $Q^{4b}$; can be hydroxy, halogen, or cyano; $Q^{4b}$ can be lower alkyl, lower alkoxy, lower alkynyl, lower alkenyl, lower hydroxyalkyl, amino, or lower haloalkyl, optionally substituted with one or more $Q^{4c}$; $Q^{4c}$ can be $Q^{4d}$ pr $Q^{4e}$; each $Q^{4d}$ can be independently halogen, hydroxy, or cyano; each $Q^{4e}$ can be independently lower alkyl, lower haloalkyl, lower alkoxy, amino, cycloalkyl, phenyl, heterocycloalkyl, or heteroaryl, optionally substituted with one or more $Q^{4f}$, and each $Q^{4f}$ can be independently hydroxy, halogen, lower alkyl, lower alkenyl, oxo, lower haloalkyl, lower alkoxy, lower hydroxyalkyl or amino.

The following Preparations disclose and enable the method of preparation of the intermediate compounds of the present invention. These Preparations which follow are provided to enable those skilled in the art to more clearly understand and to practice the present invention.

Preparation 1.

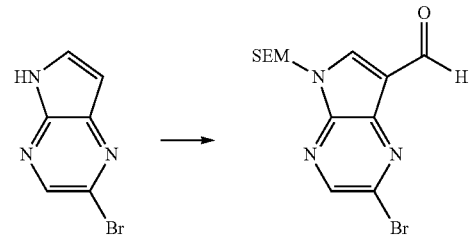

Method A
Step 1

To a partial suspension of 2-bromo-5H-pyrrolo[2,3-b]pyrazine (5.0 g, 25.2 mmol) in 1,4-dioxane (100 mL) was added 2.0 M aqueous NaOH (25 mL, 50.0 mmol) and 37% aqueous formaldehyde (19 mL, 252 mmol). The dark homogenous reaction mixture was stirred at room temperature overnight. The organics were evaporated under reduced pressure. The aqueous layer was neutralized with 1.0 M HCl and extracted with EtOAc (2×). The combined organics were concentrated to afford 2.6 g of an orange solid. Upon standing, a thick brown precipitate formed in the aqueous layer. The precipitate was collected by filtration and dried. The brown solid was extracted with hot 10% MeOH/EtOAc (3×200 mL). The extracts were combined and evaporated to provide an additional 3.05 g of orange solid. Overall yield was 5.65 g (87%) of (2-bromo-7-hydroxymethyl-pyrrolo[2,3-b]pyrazin-5-yl)-methanol.

Step 2

To a suspension of (2-bromo-7-hydroxymethyl-pyrrolo[2,3-b]pyrazin-5-yl)-methanol (5.65 g, 21.9 mmol) in THF (150 mL) was added a solution of 2.0 M aqueous NaOH (33 mL, 66 mmol). The homogeneous reaction mixture was stirred overnight then the organics were removed under reduced pressure. The aqueous residue was brought to pH 4 with 1.0 M aqueous HCl. The resulting precipitate was collected via filtration and rinsed with H$_2$O to afford 3.68 g of a yellow solid. The filtrate was extracted with EtOAc (2×) and the organics were concentrated under reduced pressure to provide an additional 0.92 g of yellow solid. Overall yield was 4.60 g (92%) of (2-bromo-5H-pyrrolo[2,3-b]pyrazin-7-yl)-methanol.

Step 3

A stock solution of Jones reagent (2.67 M) was prepared by carefully adding concentrated H$_2$SO$_4$ (2.3 mL) to CrO$_3$ (2.67 g) then diluting to 10 mL with H$_2$O. To a partial suspension of (2-bromo-5H-pyrrolo[2,3-b]pyrazin-7-yl)-methanol (4.6 g, 20.1 mmol) in acetone (300 mL) was slowly added Jones reagent (9 mL, 24.0 mmol). During the addition the starting material gradually dissolved and a thick green precipitate was formed. The reaction mixture was stirred for 15 min then quenched with i-PrOH (2 mL) and filtered over Celite, rinsing with acetone. The filtrate was concentrated to provide 4.76 g of 2-bromo-5H-pyrrolo[2,3-b]pyrazine-7-carbaldehyde as a yellow-orange solid that was used without further purification. To a solution of this solid in DMF (50 mL) at 0° C. was added NaH (60% in mineral oil, 1.2 g, 30.1 mmol). The reaction mixture was stirred at room temperature for 30 min then cooled back to 0° C. and 2-(trimethylsilyl)ethoxymethyl chloride (4.3 mL, 24.1 mmol) was slowly added. The reaction mixture was warmed to room temperature and stirred for 1 h then quenched with H₂O and extracted with EtOAc (3×). The combined organics were washed with H₂O (3×) and brine then dried over MgSO₄ and concentrated. The residue was purified by SiO₂ chromatography (20% to 30% EtOAc/hexanes) to isolate 3.82 g (53%) of 2-bromo-5-(2-trimethylsilanyl-ethoxymethyl)-5H-pyrrolo[2,3-b]pyrazine-7-carbaldehyde as a yellow solid.

Method B

Step 1

In a dry round-bottomed flask, 2-bromo-5H-pyrrolo[2,3-b]pyrazine (5.0 g, 25.2 mmol) was dissolved in DMF (50 mL). The reaction mixture was cooled to 0° C. and sodium hydride (60% dispersion in mineral oil, 1.22 g, 30.6 mmol). The reaction mixture was warmed to room temperature and stirred for 15 min then cooled back to 0° C. and SEM-Cl (5.4 mL, 30.4 mmol) was slowly added. After the addition was complete, the ice bath was removed and the reaction mixture was stirred at room temperature for 1.5 h. The reaction mixture was quenched with 50 mL water and extracted with 150 mL diethyl ether (2×). The combined organic layers were washed twice with 30 mL water and once with 30 mL brine then dried over sodium sulfate, filtered and concentrated. The residue was absorbed on ~20 g SiO₂ and chromatographed over 200 g SiO₂ with EtOAc/Hexanes (gradient: 0-15% EtOAc). All fractions containing product were combined and concentrated to afford 6.61 g (80%) of 2-bromo-5-(2-trimethylsilanyl-ethoxymethyl)-5H-pyrrolo[2,3-b]pyrazine as a pale yellow oil which gradually solidified.

Step 2

In a round-bottomed flask, 2-bromo-5-(2-trimethylsilanyl-ethoxymethyl)-5H-pyrrolo[2,3-b]pyrazine (6.58 g, 20.0 mmol) was dissolved in chloroform (pentene stabilized, 120 mL) and chloromethylenedimethyliminium chloride (10.3 g, 80.2 mmol) was added. The reaction mixture was stirred at reflux for 8 h as a steady stream of nitrogen gas was bubbled through the reaction mixture. The dark brown solution was cooled to room temperature and stirred overnight. The reaction mixture was carefully quenched with ~100 mL saturated NaHCO₃-solution (caution: exothermic) and then extracted twice with 200 mL diethyl ether. The organic layers were combined, dried over sodium sulfate, filtered and concentrated. The residue was absorbed on ~20 g SiO₂ and chromatographed over 200 g SiO₂ with EtOAc/Hexanes (gradient: 0-25% EtOAc). All fractions containing product were combined and concentrated to afford 5.92 g (83%) of an approx 3:1 mixture of 2-bromo-5-(2-trimethylsilanyl-ethoxymethyl)-5H-pyrrolo[2,3-b]pyrazine-7-carbaldehyde and 2-chloro-5-(2-trimethylsilanyl-ethoxymethyl)-5H-pyrrolo[2,3-b]pyrazine-7-carbaldehyde as a yellow solid.

Preparation 2.

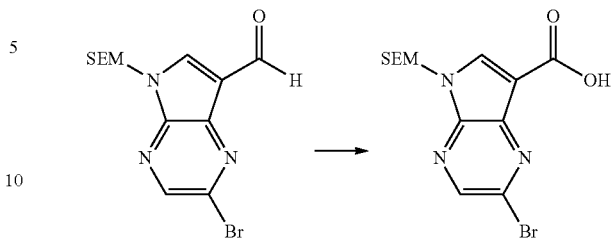

In a flask 2-bromo-5-(2-trimethylsilanylethoxymethyl)-5H-pyrrolo[2,3-b]pyrazine-7-carbaldehyde (3.11 g, 8.74 mmol) was dissolved in dioxane (120 mL) and H₂O (30 mL) and the mixture cooled at 0° C. Sufamic acid (5.09 g, 52.4 mmol) was added, followed by a solution of sodium chlorite (1.28 g, 11.4 mmol) and potassium dihydrogen phosphate (14.3 g, 104.9 mmol) in H₂O (75 mL) via an addition funnel over 15 min. The mixture was allowed to warm to room temperature over 2 h. The resulting yellow solid was filtered off, washed with H₂O and hexane and dried. The filtrate was then extracted with EtOAc, and the combined organics washed with brine, dried over MgSO₄ and concentrated to give additional product. In total 3.71 g of 2-bromo-5-(2-trimethylsilanylethoxymethyl)-5H-pyrrolo[2,3-b]pyrazine-7-carboxylic acid was obtained as a yellow solid.

Preparation 3.

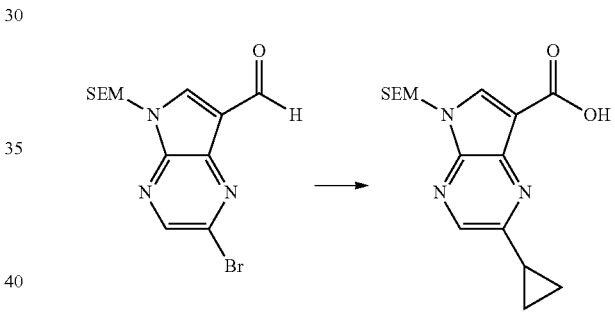

Step 1

A mixture of 2-bromo-5-(2-trimethylsilanyl-ethoxymethyl)-5H-pyrrolo[2,3-b]pyrazine-7-carbaldehyde (0.33 g, 0.93 mmol), cyclopropyl boronic acid (0.12 g, 1.39 mmol), tricyclohexyl phosphine (0.026 g, 0.09 mmol), palladium(II) acetate (0.01 g, 0.046 mmol) and potassium phosphate tribasic (0.63 g, 2.97 mmol) in 4 mL of toluene and 0.5 mL of water was flushed with Argon for 5 min then heated at 100° C. for 18 h. The cooled mixture was filtered through a pad of Celite, washed with EtOAc, and concentrated under reduced pressure. The residue was purified by silica gel chromatography eluting with 10% EtOAc/hexanes to afford 0.24 g (81%) of 2-cyclopropyl-5-(2-trimethylsilanyl-ethoxymethyl)-5H-pyrrolo[2,3-b]pyrazine-7-carbaldehyde as a yellow powder.

Step 2

To a solution of 2-cyclopropyl-5-(2-trimethylsilanyl-ethoxymethyl)-5H-pyrrolo[2,3-b]pyrazine-7-carbaldehyde (0.24 g, 0.75 mmol) in 1,4-dioxane (10 mL) and water (2 mL) at 0° C. was added sulfamic acid (0.44 g, 4.54 mmol). Then added dropwise a solution of sodium chlorite (0.09 g, 0.98 mmol) and potassium dihydrogen phosphate (1.22 g, 9.0 mmol) in 6 mL of water. After the addition, the reaction mixture was warmed to room temperature and stirred for 2 h then partitioned between water and ethyl acetate. The organic layer was washed with brine, dried over sodium sulfate and concentrated under reduced pressure. The residue was triturated with hexanes to obtain 0.22 g (87%) of 2-cyclopropyl-5-(2-trimethylsilanyl-ethoxymethyl)-5H-pyrrolo[2,3-b]pyrazine-7-carboxylic acid as a light yellow powder.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Methods of Treatment

The novel pyrrolopyrazine derivatives provided herein selectively inhibit JAK3 and are useful for the treatment of auto-immune and inflammatory diseases. The compounds of the invention modulate the JAK and/or SYK pathways and are useful novel pyrrolopyrazine derivatives for the treatment of auto-immune and inflammatory diseases, wherein preferred compounds selectively inhibit JAK3. For example, the compounds of the invention may inhibit JAK3 and SYK, wherein preferred compounds are selective for JAK3 of the JAK kinases and are useful novel pyrrolopyrazine derivatives for the treatment of auto-immune and inflammatory diseases. The amide linker at the 7-position of the 5H-pyrrolo[2,3-b]pyrazines affords the compounds of formula I and I' unexpected increased potency in inhibition of JAK and Syk kinases compared to 5H-pyrrolo[2,3-b]pyrazines with other moieties at that position. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases.

The application provides a method for treating an inflammatory or autoimmune condition comprising administering to a patient in need thereof a therapeutically effective amount of the compound of formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of formula I.

The application provides a method for inhibiting T-cell proliferative disorder comprising administering to a patient in need thereof a therapeutically effective amount of the compound of formula I.

The application provides a method for inhibiting T-cell proliferative disorder comprising administering to a patient in need thereof a therapeutically effective amount of the compound of formula I.

The application provides the above method, wherein the proliferative disorder is cancer.

The application provides a method for treating a B-cell proliferative disorder comprising administering to a patient in need thereof a therapeutically effective amount of the compound of formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of formula I.

The application provides a method for preventing or treating all forms of organ rejection, including acute allograft or xenograft rejection and chronic allograft or xenograft rejection, of vascularized or non-vascularized transplants, comprising administering to a patient in need thereof the compound of formula I.

The application provides a method for inhibiting JAK3 activity comprising administering the compound of formula I, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

The application provides a method for inhibiting SYK activity comprising administering the compound of formula I, wherein the compound exhibits an $IC_{50}$ of 50 micromolar or less in an in vitro biochemical assay of SYK activity.

The application provides the above method, wherein the compound exhibits an $IC_{50}$ of 100 nanomolar or less in an in vitro biochemical assay of SYK activity.

The application provides the above method, wherein the compound exhibits an $IC_{50}$ of 10 nanomolar or less in an in vitro biochemical assay of SYK activity.

The application provides a method for treating an inflammatory condition comprising co-administering to a patient in need thereof a therapeutically effective amount of an anti-inflammatory compound in combination with the compound of formula I.

The application provides a method for treating an immune disorder comprising co-administering to a patient in need thereof a therapeutically effective amount of an immunosuppressant compound in combination with the compound of formula I.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp or MP), MeSO$_2$-(mesyl or Ms), methyl (Me), acetonitrile (MeCN), m-chloroperbenzoic acid (MCPBA), mass spectrum (ms or MS), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), 2-(trimethylsilyl) ethoxymethyl chloride (SEMC1), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$- (TO, trifluoroacetic acid (TFA), 1,1'-bis-2,2,6,6-tetramethyl-heptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Example 1

2-Cyclopropyl-5H-pyrrolo[2,3-b]pyrazine-7-carboxylic acid [1-(1-hydroxy-1-methyl-ethyl)-cyclopentyl]-amide

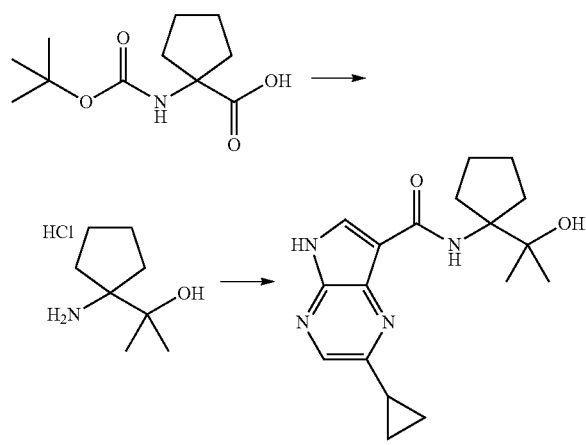

Step 1

In a 150 mL round-bottomed flask 1-tert-butoxycarbonylamino-cyclopentanecarboxylic acid (1.00 g, 4.36 mmol) was dissolved in acetone (30 mL). Potassium carbonate (1.51 g, 10.9 mmol) was added followed by iodomethane (0.41 mL, 6.54 mmol). The reaction mixture was heated at reflux overnight then cooled to room temperature and filtered. The filtrate was concentrated under reduced pressure and the residue was partitioned between diethyl ether and H$_2$O. The aqueous layer was extracted with diethyl ether. The combined organics were washed with H$_2$O and brine then dried over Na$_2$SO$_4$, filtered and concentrated to afford 1.1 g (99%) of 1-tert-butoxycarbonylamino-cyclopentanecarboxylic acid methyl ester as a white solid.

Step 2

In a 50 mL 3-neck round-bottomed flask 1-tert-butoxycarbonylamino-cyclopentanecarboxylic acid methyl ester (0.60 g, 2.47 mmol) was dissolved in THF (16 mL). The solution was cooled to 0° C. and methylmagnesium bromide (3.0 M in solution in Et$_2$O, 3.0 mL, 9.0 mmol) was added dropwise over 10 min. The reaction mixture was allowed to warm slowly to room temperature overnight. The reaction mixture was cooled to 0° C. and quenched with saturated aqueous NH$_4$Cl. Diluted with 1.0 M aqueous HCl and extracted with EtOAc (2×). The combined organics were washed with H$_2$O and brine then dried over Na$_2$SO$_4$ and concentrated. The residue was purified by chromatography over 24 g of SiO$_2$ using EtOAc/hexanes (gradient: 0-20% EtOAc) to provide 0.31 g (51%) of [1-(1-hydroxy-1-methyl-ethyl)-cyclopentyl]-carbamic acid tert-butyl ester as a white solid.

Step 3

In a 25 mL round-bottomed flask [1-(1-hydroxy-1-methyl-ethyl)-cyclopentyl]-carbamic acid tert-butyl ester (0.31 g, 1.27 mmol) was dissolved in 1.0 M HCl solution in MeOH (8.2 mL, 8.2 mmol). The reaction mixture was stirred at 50° C. for 4 h then cooled to room temperature and concentrated under reduced pressure to afford 0.23 g (96%) of 2-(1-amino-cyclopentyl)-propan-2-ol hydrochloride as an off-white foam which was used without further purification.

Step 4

In a round-bottomed flask were combined 2-cyclopropyl-5-(2-trimethylsilanyl-ethoxymethyl)-5H-pyrrolo[2,3-b]pyrazine-7-carboxylic acid (150 mg, 0.45 mmol), 2-(1-amino-cyclopentyl)-propan-2-ol hydrochloride (115 mg, 0.64 mmol), EDC (95 mg, 0.50 mmol), and HOBt (67 mg, 0.50 mmol). Then added DMF (2 mL) followed by i-Pr$_2$NEt (0.20 mL, 1.12 mmol). The reaction mixture was stirred at room temperature overnight then quenched with H$_2$O and extracted with EtOAc (3×). The combined organics were washed with H$_2$O (3×) and brine then dried over Na$_2$SO$_4$ and concentrated. The residue was purified by chromatography over 12 g of SiO$_2$ using EtOAc/hexanes (gradient: 0-30% EtOAc) to afford 209 mg (96%) of 2-cyclopropyl-5-(2-trimethylsilanyl-ethoxymethyl)-5H-pyrrolo[2,3-b]pyrazine-7-carboxylic acid [1-(1-hydroxy-1-methyl-ethyl)-cyclopentyl]-amide as a pale yellow oil.

Step 5

In a 10 mL round-bottomed flask, 2-cyclopropyl-5-(2-trimethylsilanyl-ethoxymethyl)-5H-pyrrolo[2,3-b]pyrazine-7-carboxylic acid [1-(1-hydroxy-1-methyl-ethyl)-cyclopentyl]-amide (207 mg, 0.45 mmol) was dissolved in CH$_2$Cl$_2$ (5 mL). Trifluoroacetic acid (1.7 mL) was added and the light yellow reaction mixture was stirred at room temperature for 2 h then concentrated. The residue was taken up in toluene (5 mL), concentrated and then dried under high vacuum. The residue was dissolved in CH$_2$Cl$_2$ (2.5 mL) and ethylenediamine (2.5 mL) was added. The reaction mixture was stirred at room temperature for 1 h then H$_2$O and EtOAc were added. The aqueous layer was extracted with EtOAc. The combined organics were washed with H$_2$O and brine, dried over Na$_2$SO$_4$ and concentrated. The residue was purified by chromatography over 12 g of SiO$_2$ using EtOAc/hexanes (gradient: 0-90% EtOAc) to afford 79 mg (53%) of 2-cyclopropyl-5H-pyrrolo[2,3-b]pyrazine-7-carboxylic acid [1-(1-hydroxy-1-methyl-ethyl)-cyclopentyl]-amide as a white solid. MS: (M+H)$^+$=329; mp=232.0-234.0.

Example 2

2-Cyclopropyl-5H-pyrrolo[2,3-b]pyrazine-7-carboxylic acid [1-(1-hydroxy-1-methyl-ethyl)-cyclobutyl]-amide

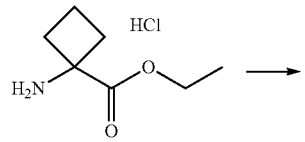

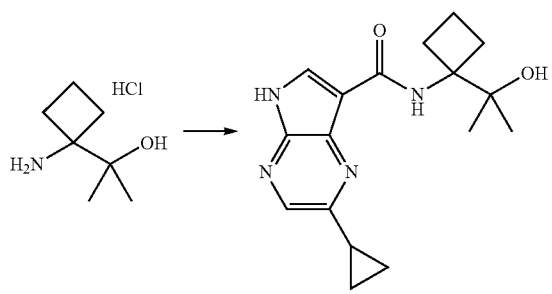

Step 1

To a solution of ethyl 1-amino-1-cyclobutane-carboxylate hydrochloride (1.20 g, 6.67 mmol) in DMF (13 mL) was added di-tert-butyldicarbonate (1.61 g, 7.35 mmol). Triethylamine (1.12 mL, 8.04 mmol) was added dropwise and the reaction mixture was stirred at room temperature for 3.5 h then water and diethyl ether were added. The aqueous layer was extracted with diethyl ether. The combined organic layers were washed with 1.0 M HCl, water and brine then dried over Na$_2$SO$_4$ and concentrated to afford 1.58 g (97%) of 1-tert-butoxycarbonylamino-cyclobutanecarboxylic acid ethyl ester as an off-white solid.

Step 2

2-Cyclopropyl-5H-pyrrolo[2,3-b]pyrazine-7-carboxylic acid [1-(1-hydroxy-1-methyl-ethyl)-cyclobutyl]-amide was prepared according to the procedure outlined in Example 1, steps 2-5 substituting 1-tert-butoxycarbonylamino-cyclobutanecarboxylic acid ethyl ester for 1-tert-butoxycarbonylamino-cyclopentanecarboxylic acid methyl ester. MS: (M+H)$^+$=315; mp=264.0-266.0.

Example 3

2-Cyclopropyl-5H-pyrrolo[2,3-b]pyrazine-7-carboxylic acid [1-(1-hydroxy-1-methyl-ethyl)-cyclohexyl]-amide

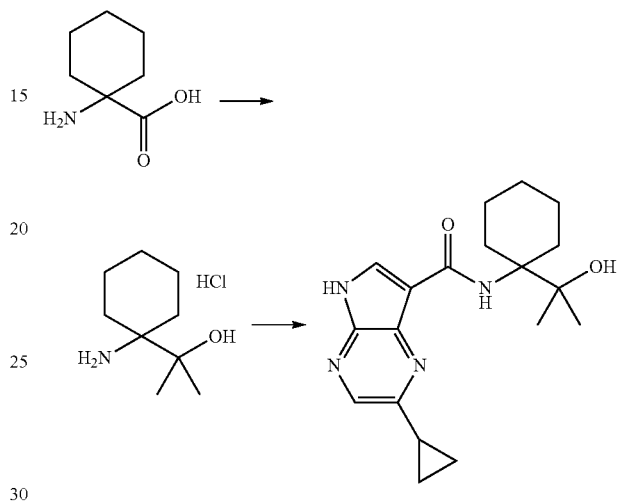

Step 1

In a round-bottomed flask 1-amino-1-cyclohexanecarboxylic acid (1.00 g, 7.0 mmol) was suspended in dichloromethane (26 mL) and MeOH (13 mL). (Trimethylsilyl)diazomethane (2.0 M in hexanes, 6.0 mL, 12.0 mmol) was added dropwise and the reaction mixture gradually became homogeneous as it was stirred at room temperature overnight. The reaction mixture was quenched with a small portion of acetic acid and concentrated under reduced pressure. The residue was dissolved in dichloromethane and washed with saturated aqueous Na$_2$CO$_3$. The aqueous layer was extracted with dichloromethane and the combined organics were dried over Na$_2$SO$_4$ and concentrated to afford 1.15 g of 1-amino-1-cyclohexanecarboxylic acid methyl ester as a light yellow oil.

Step 2

To a solution of 1-amino-1-cyclohexanecarboxylic acid methyl ester (1.15 g, 7.0 mmol, crude from step 1) in CH$_2$Cl$_2$ (20 mL) was added di-tert-butyldicarbonate (1.77 g, 8.1 mmol). The reaction mixture was stirred at room temperature overnight then diluted with CH$_2$Cl$_2$ and washed with 1.0 M HCl and water. The aqueous layer was extracted with CH$_2$Cl$_2$ and the combined organics were dried over Na$_2$SO$_4$ and concentrated to afford 2.07 g 1-tert-butoxycarbonylamino-cyclohexanecarboxylic acid methyl ester of as a light yellow oil which was used without further purification.

Step 3

2-Cyclopropyl-5H-pyrrolo[2,3-b]pyrazine-7-carboxylic acid [1-(1-hydroxy-1-methyl-ethyl)-cyclohexyl]-amide was prepared according to the procedure outlined in Example 1, steps 2-5 substituting 1-tert-butoxycarbonylamino-cyclohexanecarboxylic acid methyl ester for 1-tert-butoxycarbonylamino-cyclopentanecarboxylic acid methyl ester. MS: (M+H)⁺=343; mp=228.0-230.0.

Example 4

2-Cyclopropyl-5H-pyrrolo[2,3-b]pyrazine-7-carboxylic acid [3-(1-hydroxy-1-methyl-ethyl)-pyrrolidin-3-yl]-amide hydrochloride

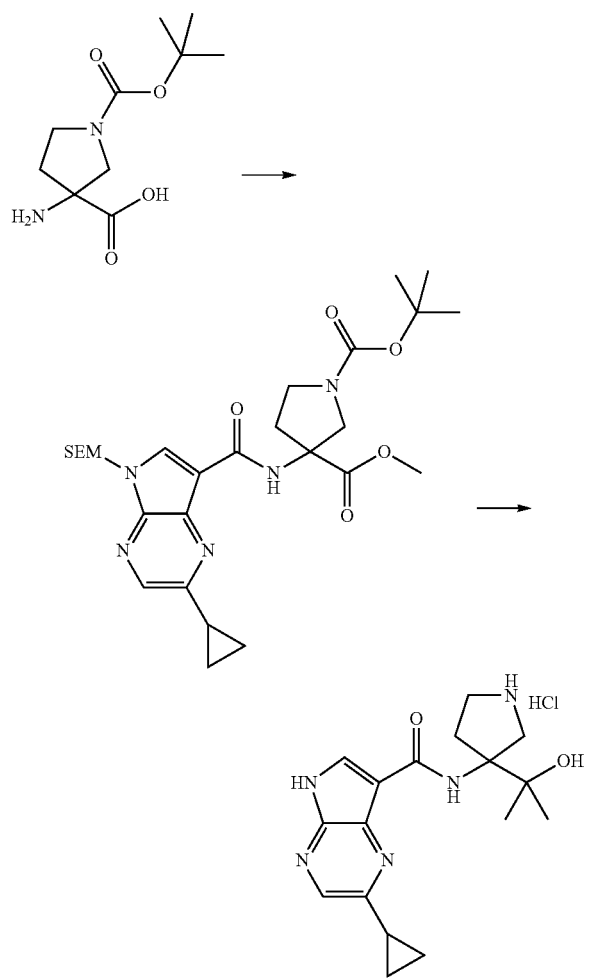

Step 1

In a round-bottomed flask 3-aminopyrrolidine-1,3-dicarboxylic acid 1-tert-butyl ester (0.20 g, 0.87 mmol) was dissolved in dichloromethane (3.2 mL) and MeOH (1.6 mL). (Trimethylsilyl)diazomethane (2.0 M in hexanes, 0.75 mL, 1.5 mmol) was added dropwise and the reaction mixture was stirred at room temperature for 5 h. The reaction mixture was quenched with a small portion of acetic acid and concentrated under reduced pressure. The residue was dissolved in dichloromethane and washed with saturated aqueous Na₂CO₃. The aqueous layer was extracted with dichloromethane and the combined organics were dried over Na₂SO₄ and concentrated to afford 0.218 g of 3-amino-pyrrolidine-1,3-dicarboxylic acid 1-tert-butyl ester 3-methyl ester as a light yellow oil.

Step 2

In a round-bottomed flask were combined 2-cyclopropyl-5-(2-trimethylsilanyl-ethoxymethyl)-5H-pyrrolo[2,3-b]pyrazine-7-carboxylic acid (180 mg, 0.54 mmol), 3-amino-pyrrolidine-1,3-dicarboxylic acid 1-tert-butyl ester 3-methyl ester (214 mg, 0.87 mmol), EDC (114 mg, 0.59 mmol), and HOBt (80 mg, 0.59 mmol). Then added DMF (2.4 mL) followed by i-Pr₂NEt (0.14 mL, 0.80 mmol). The reaction mixture was stirred at room temperature overnight then quenched with H₂O and extracted with Et₂O (2×). The combined organics were washed with H₂O (2×) and brine then dried over Na₂SO₄ and concentrated. The residue was purified by chromatography over 24 g of SiO₂ using EtOAc/hexanes (gradient: 0-40% EtOAc) to afford 276 mg (91%) of 3-{[2-Cyclopropyl-5-(2-trimethylsilanyl-ethoxymethyl)-5H-pyrrolo[2,3-b]pyrazine-7-carbonyl]-amino}-pyrrolidine-1,3-dicarboxylic acid 1-tert-butyl ester 3-methyl ester as an off-white foam.

Step 3

In a round-bottomed flask 3-{[2-Cyclopropyl-5-(2-trimethylsilanyl-ethoxymethyl)-5H-pyrrolo[2,3-b]pyrazine-7-carbonyl]-amino}-pyrrolidine-1,3-dicarboxylic acid 1-tert-butyl ester 3-methyl ester (0.27 g, 0.48 mmol) was dissolved in THF (4 mL). The solution was cooled to 0° C. and methylmagnesium bromide (3.0 M in solution in Et₂O, 0.6 mL, 1.8 mmol) was added dropwise over 10 min. The reaction mixture was allowed to warm slowly to room temperature overnight. The reaction mixture was cooled to 0° C., quenched with saturated aqueous NH₄Cl and extracted with EtOAc (2×). The combined organics were washed with H₂O and brine then dried over Na₂SO₄ and concentrated. The residue was purified by chromatography over 24 g of SiO₂ using EtOAc/hexanes (gradient: 0-50% EtOAc) to provide 0.122 g (45%) of 3-{[2-cyclopropyl-5-(2-trimethylsilanyl-ethoxymethyl)-5H-pyrrolo[2,3-b]pyrazine-7-carbonyl]-amino}-3-(1-hydroxy-1-methyl-ethyl)-pyrrolidine-1-carboxylic acid tert-butyl ester as a light yellow oil.

Step 4

In a 10 mL round-bottomed flask, 3-{[2-cyclopropyl-5-(2-trimethylsilanyl-ethoxymethyl)-5H-pyrrolo[2,3-b]pyrazine-7-carbonyl]-amino}-3-(1-hydroxy-1-methyl-ethyl)-pyrrolidine-1-carboxylic acid tert-butyl ester (118 mg, 0.21 mmol) was dissolved in CH₂Cl₂ (1 mL). Trifluoroacetic acid (0.8 mL) was added and the light yellow reaction mixture was stirred at room temperature for 2 h then concentrated. The residue was taken up in toluene (3 mL), concentrated and then dried under high vacuum. The residue was dissolved in CH₂Cl₂ (1 mL) and ethylenediamine (1 mL) was added. The reaction mixture was stirred at room temperature for 1 h then H₂O and EtOAc were added. The aqueous layer was extracted with EtOAc. The combined organics were washed with H₂O and brine, dried over Na₂SO₄ and concentrated. The residue was triturated with EtOAc to afford 37 mg (48%) of 2-cyclopropyl-5H-pyrrolo[2,3-b]pyrazine-7-carboxylic acid [3-(1-hydroxy-1-methyl-ethyl)-pyrrolidin-3-yl]-amide as a yellow solid.

Step 5

To a solution of 2-cyclopropyl-5H-pyrrolo[2,3-b]pyrazine-7-carboxylic acid [3-(1-hydroxy-1-methyl-ethyl)-pyrrolidin-3-yl]-amide (37 mg, 0.11 mmol) in MeOH (0.3 mL) at 0° C. was added HCl (1.0 M in MeOH, 0.17 mL, 0.17 mmol). The reaction mixture was stirred at room temperature for 5 min then concentrated. The residue was triturated with Et₂O to afford 34 mg (92%) of 2-cyclopropyl-5H-pyrrolo[2,3-b]pyrazine-7-carboxylic acid [3-(1-hydroxy-1-methyl-ethyl)-

Example 5

2-Cyclopropyl-5H-pyrrolo[2,3-b]pyrazine-7-carboxylic acid [3-(1-hydroxy-1-methyl-ethyl)-tetrahydro-furan-3-yl]-amide

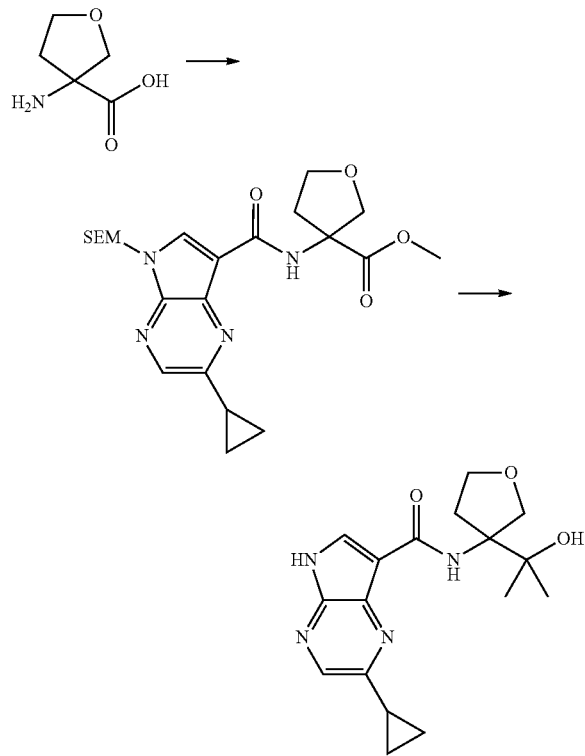

Prepared according to the procedure outlined in Example 4, steps 1-4 substituting 3-aminotetrahydrofuran-3-carboxylic acid for 3-aminopyrrolidine-1,3-dicarboxylic acid 1-tert-butyl ester. MS: (M+H)$^+$=331; mp=213.0-215.0.

Example 6

2-Cyclopropyl-5H-pyrrolo[2,3-b]pyrazine-7-carboxylic acid (1-methanesulfonyl-pyrrolidin-3-yl)-amide

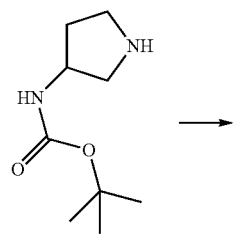

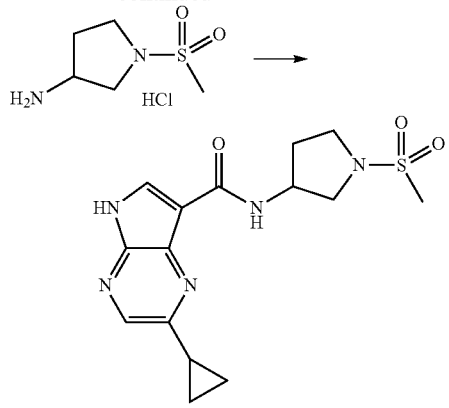

Step 1

In a 15 mL round-bottomed flask, 3-(tert-butoxycarbonylamino)pyrrolidine (0.50 g, 2.68 mmol) was dissolved in CH$_2$Cl$_2$ (5 mL). Triethylamine (0.45 mL, 3.22 mmol) was added and the reaction mixture was cooled to 0° C. Methanesulfonyl chloride (0.25 mL, 3.22 mmol) was added dropwise and the reaction mixture was slowly warmed to room temperature and stirred overnight. The reaction was diluted with CH$_2$Cl$_2$ (20 mL) and quenched with 1.0 M aqueous HCl (5 mL). The aqueous layer was extracted with CH$_2$Cl$_2$ then the combined organics were dried over Na$_2$SO$_4$, filtered and concentrated to afford 0.90 g of (1-methanesulfonyl-pyrrolidin-3-yl)-carbamic acid tert-butyl ester as a light brown solid which was used without further purification.

Step 2

In a 10 mL round-bottomed flask, (1-methanesulfonyl-pyrrolidin-3-yl)-carbamic acid tert-butyl ester (0.18 g, 0.68 mmol) was dissolved in 1.0 M hydrogen chloride solution in MeOH (3.2 mL, 3.2 mmol). The reaction mixture was stirred at 50° C. for 3 h then cooled to room temperature and concentrated to afford 137 mg of 1-methanesulfonyl-pyrrolidin-3-ylamine hydrochloride as a light yellow solid which was used without further purification.

Step 3

In a round-bottomed flask were combined 2-cyclopropyl-5-(2-trimethylsilanyl-ethoxymethyl)-5H-pyrrolo[2,3-b]pyrazine-7-carboxylic acid (130 mg, 0.39 mmol), 1-methanesulfonyl-pyrrolidin-3-ylamine hydrochloride (134 mg, 0.66 mmol), EDC (82 mg, 0.43 mmol), and HOBt (58 mg, 0.43 mmol). Then added DMF (1.7 mL) followed by i-Pr$_2$NEt (0.17 mL, 1.0 mmol). The reaction mixture was stirred at room temperature overnight then quenched with H$_2$O and extracted with Et$_2$O (2×). The combined organics were washed with H$_2$O (2×) and brine then dried over Na$_2$SO$_4$ and concentrated. The residue was purified by chromatography over 12 g of SiO$_2$ using EtOAc/hexanes (gradient: 0-90% EtOAc) to afford 179 mg (96%) of 2-cyclopropyl-5-(2-trimethylsilanyl-ethoxymethyl)-5H-pyrrolo[2,3-b]pyrazine-7-carboxylic acid (1-methanesulfonyl-pyrrolidin-3-yl)-amide as a colorless oil.

Step 4

In a 10 mL round-bottomed flask, 2-cyclopropyl-5-(2-trimethylsilanyl-ethoxymethyl)-5H-pyrrolo[2,3-b]pyrazine-7-carboxylic acid (1-methanesulfonyl-pyrrolidin-3-yl)-amide (177 mg, 0.37 mmol) was dissolved in CH$_2$Cl$_2$ (3 mL). Trifluoroacetic acid (1.1 mL) was added and the light yellow reaction mixture was stirred at room temperature for 2 h then concentrated. The residue was taken up in toluene (5 mL), concentrated and then dried under high vacuum. The residue was dissolved in CH$_2$Cl$_2$ (2.5 mL) and ethylenediamine (1.5 mL) was added. The reaction mixture was stirred at room temperature overnight then diluted with MeOH and the solid precipitate was collected via filtration. The solid residue was rinsed with hot water and EtOAc then dried under high vacuum to afford 56 mg (43%) of 2-cyclopropyl-5H-pyrrolo[2,3-b]pyrazine-7-carboxylic acid (1-methanesulfonyl-pyrrolidin-3-yl)-amide as a white solid. MS: (M+H)$^+$=350; mp>300.

Example 7

2-Cyclopropyl-5H-pyrrolo[2,3-b]pyrazine-7-carboxylic acid (1-acetyl-pyrrolidin-3-yl)-amide

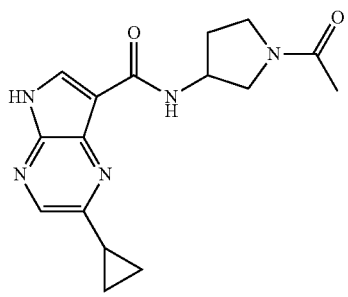

Prepared according to the procedure outlined in Example 6 substituting acetyl chloride for methanesulfonyl chloride in step 1. MS: (M+H)$^+$=314; mp 242.0-245.0.

Example 8

2-Cyclopropyl-5H-pyrrolo[2,3-b]pyrazine-7-carboxylic acid (1-methanesulfonyl-piperidin-4-yl)-amide

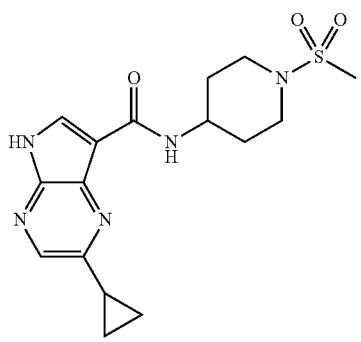

Prepared according to the procedure outlined in Example 6 substituting 4-(tert-butoxycarbonylamino)piperidine for 3-(tert-butoxycarbonylamino)pyrrolidine in step 1. MS: (M+H)$^+$=364; mp 278.0-280.0.

Example 9

2-Cyclopropyl-5H-pyrrolo[2,3-b]pyrazine-7-carboxylic acid (1-acetyl-piperidin-4-yl)-amide

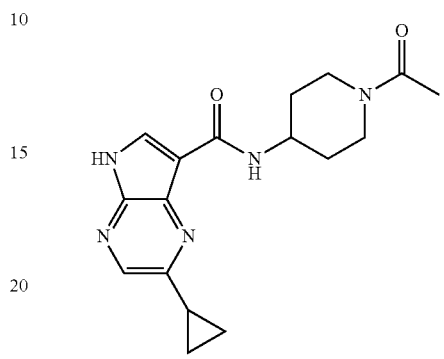

Prepared according to the procedure outlined in Example 6 substituting 4-(tert-butoxycarbonylamino)piperidine for 3-(tert-butoxycarbonylamino)pyrrolidine and acetyl chloride for methanesulfonyl chloride in step 1. MS: (M+H)$^+$=328; mp 273.0-275.0.

Example 10

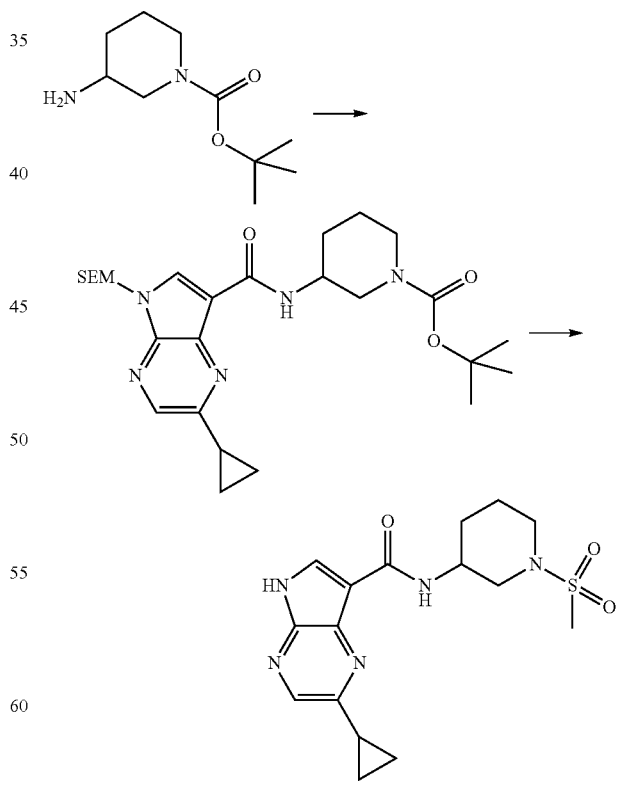

Step 1

A 10 mL round-bottomed flask was charged with 2-cyclopropyl-5-42-(trimethylsilyl)ethoxy)methyl)-5H-pyrrolo[2, 3-b]pyrazine-7-carboxylic acid (300 mg, 0.90 mmol), 1-Boc-3-aminopiperidine (252 mg, 1.25 mmol), HOBT (134 mg, 1.0 mmol) and EDC (190 mg, 1.0 mmol). Then added DMF (4 mL) followed by N,N-diisopropylethylamine (0.24 mL, 1.35 mmol). The yellow reaction mixture was stirred at room temperature for 2 days then quenched with H₂O (5 mL) and extracted with Et₂O (2×50 mL). The combined organic layers were washed twice with H₂O and once with brine then dried over Na₂SO₄, filtered and concentrated. The residue was purified by chromatography over 24 g SiO₂ using EtOAc/Hexanes (gradient: 0-40% EtOAc) to afford 438 mg (94%) of 3-{[2-cyclopropyl-5-(2-trimethylsilanyl-ethoxymethyl)-5H-pyrrolo[2,3-b]pyrazine-7-carbonyl]-amino}-piperidine-1-carboxylic acid tert-butyl ester as an off-white foam.

Step 2

In a 25 mL round-bottomed flask, 3-{[2-cyclopropyl-5-(2-trimethylsilanyl-ethoxymethyl)-5H-pyrrolo[2,3-b]pyrazine-7-carbonyl]-amino}-piperidine-1-carboxylic acid tert-butyl ester (0.435 g, 0.84 mmol) was dissolved in MeOH (7 mL). The solution was cooled to 0° C. and acetyl chloride (1.2 mL, 16.8 mmol) was added dropwise over 10 min. The ice bath was removed and the reaction mixture was stirred at room temperature for 1.5 h. The solvent was evaporated at room temperature and the residue was dried under high vacuum to afford 402 mg of 2-cyclopropyl-5-(2-trimethylsilanyl-ethoxymethyl)-5H-pyrrolo[2,3-b]pyrazine-7-carboxylic acid piperidin-3-ylamide hydrochloride as a light yellow foam which was used without further purification.

Step 3

In a 15 mL round-bottomed flask, 2-cyclopropyl-5-(2-trimethylsilanyl-ethoxymethyl)-5H-pyrrolo[2,3-b]pyrazine-7-carboxylic acid piperidin-3-ylamide hydrochloride (200 mg, 0.44 mmol) was dissolved in CH₂Cl₂ (3 mL) and cooled to 0° C. Added triethylamine (0.12 mL, 0.88 mmol) followed by methanesulfonyl chloride (0.04 mL, 0.48 mmol). The reaction mixture was stirred at room temperature for 6 h then diluted with 30 mL of CH₂Cl₂ and washed with water (5 mL). The aqueous layer was extracted with CH₂Cl₂ (30 mL) and the combined organic layers were dried over Na₂SO₄, filtered and concentrated. The residue was purified by chromatography over 12 g SiO₂ with EtOAc/Hexanes (gradient: 0-100% EtOAc) to provide 174 mg (89%) of 2-cyclopropyl-5-(2-trimethylsilanyl-ethoxymethyl)-5H-pyrrolo[2,3-b]pyrazine-7-carboxylic acid (1-methanesulfonyl-piperidin-3-yl)-amide as a white foam.

Step 4

In a 10 mL round-bottomed flask, 2-cyclopropyl-5-(2-trimethylsilanyl-ethoxymethyl)-5H-pyrrolo[2,3-b]pyrazine-7-carboxylic acid (1-methanesulfonyl-piperidin-3-yl)-amide (173 mg, 0.35 mmol) was dissolved in CH₂Cl₂ (1.4 mL). Trifluoroacetic acid (1.1 mL) was added and the light yellow reaction mixture was stirred at room temperature for 2 h then concentrated. The residue was taken up in toluene (3 mL), concentrated and then dried under high vacuum. The residue was dissolved in CH₂Cl₂ (1.4 mL) and ethylenediamine (1.4 mL) was added. The reaction mixture was stirred at room temperature for 2 h then H₂O and EtOAc were added. The resultant suspension was filtered, rinsing with H₂O and EtOAc and dried under high vacuum to afford 103 mg (81%) of 2-cyclopropyl-5H-pyrrolo[2,3-b]pyrazine-7-carboxylic acid (1-methanesulfonyl-piperidin-3-yl)-amide as an off-white solid. MS: (M+H)⁺=364; mp=284.0-287.0.

Example 11

2-Cyclopropyl-5H-pyrrolo[2, 3-1)]pyrazine-7-carboxylic acid (1-acetyl-piperidin-3-yl)-amide

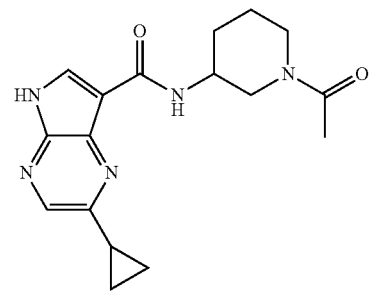

Prepared according to the procedure outlined in Example 10 substituting acetyl chloride for methanesulfonyl chloride in step 3. MS: (M+H)⁺=328; mp 215.0-218.0.

Example 12

2-Cyclopropyl-5H-pyrrolo[2,3-b]pyrazine-7-carboxylic acid (1-ethanesulfonyl-piperidin-3-yl)-amide

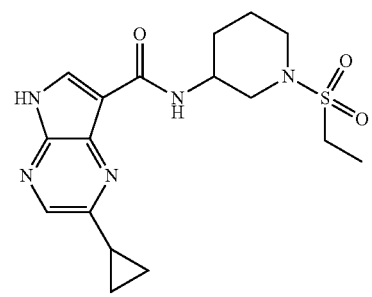

Prepared according to the procedure outlined in Example 10 substituting ethanesulfonyl chloride for methanesulfonyl chloride in step 3. MS: (M+H)⁺=378; mp 266.0-269.0.

Example 13

2-Cyclopropyl-5H-pyrrolo[2,3-b]pyrazine-7-carboxylic acid [1-(propane-1-sulfonyl)-piperidin-3-yl]amide

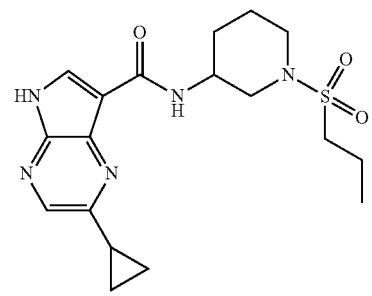

Prepared according to the procedure outlined in Example 10 substituting 1-propanesulfonyl chloride for methanesulfonyl chloride in step 3. MS: (M+H)⁺=392; mp 228.0-230.0.

Example 14

2-Cyclopropyl-5H-pyrrolo[2,3-b]pyrazine-7-carboxylic acid [1-(propane-2-sulfonyl)-piperidin-3-yl]-amide

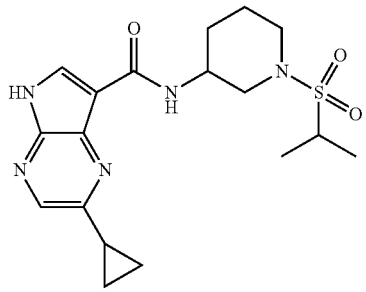

Prepared according to the procedure outlined in Example 10 substituting 2-propanesulfonyl chloride for methanesulfonyl chloride in step 3. MS: (M+H)⁺=392; mp 255.0-258.0.

Example 15

2-Cyclopropyl-5H-pyrrolo[2,3-b]pyrazine-7-carboxylic acid ((R)-1-methane sulfonyl-piperidin-3-yl)-amide

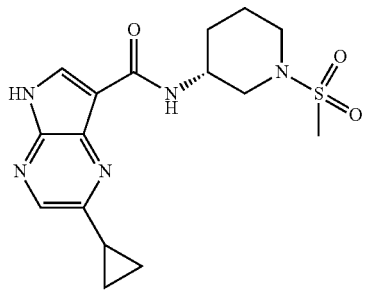

Prepared according to the procedure outlined in Example 10 substituting (R)-1-Boc-3-aminopiperidine for 1-Boc-3-aminopiperidine in step 1. MS: (M+H)⁺=364; mp 277.0-280.0.

Example 16

2-Cyclopropyl-5H-pyrrolo[2,3-b]pyrazine-7-carboxylic acid ((S)-1-methanesulfonyl-piperidin-3-yl)-amide

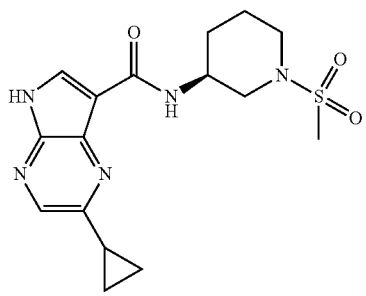

Prepared according to the procedure outlined in Example 10 substituting (S)-1-Boc-3-aminopiperidine for 1-Boc-3-aminopiperidine in step 1. MS: (M+H)⁺=364; mp 278.0-281.0.

Example 17

2-Cyclopropyl-5H-pyrrolo[2,3-b]pyrazine-7-carboxylic acid cyclohexylamide

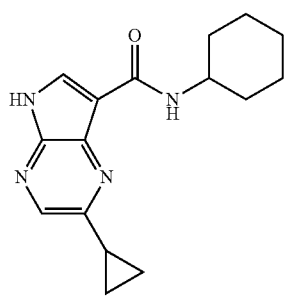

Step 1

To a solution of 2-cyclopropyl-5-(2-(trimethylsilyl)ethoxy)methyl)-5H-pyrrolo[2,3-b]pyrazine-7-carboxylic acid (80 mg, 0.24 mmol) in THF (2.0 mL) was added 1,1'-carbonyldiimidazole (47 mg, 0.29 mmol). The reaction mixture was stirred at 60° C. for 45 min then cooled to room temperature. Cyclohexylamine (0.27 mL, 2.4 mmol) was added and the reaction mixture was stirred at room temperature for 1.5 h. Water and EtOAc were added and the aqueous layer was extracted with EtOAc. The combined organics were washed with water and brine then dried over Na₂SO₄ and concentrated. The residue was purified by chromatography over 8 g SiO₂ with EtOAc/Hexanes (gradient: 0-30% EtOAc) to provide 106 mg of 2-cyclopropyl-5-(2-trimethylsilanyl-ethoxymethyl)-5H-pyrrolo[2,3-b]pyrazine-7-carboxylic acid cyclohexylamide as a white solid.

Step 2

In a 10 mL round-bottomed flask, 2-cyclopropyl-5-(2-trimethylsilanyl-ethoxymethyl)-5H-pyrrolo[2,3-b]pyrazine-7-carboxylic acid cyclohexylamide (94 mg, 0.23 mmol) was dissolved in CH₂Cl₂ (0.9 mL). Trifluoroacetic acid (0.7 mL) was added and the light yellow reaction mixture was stirred at room temperature for 2 h then concentrated. The residue was taken up in toluene (3 mL), concentrated and then dried under high vacuum. The residue was dissolved in CH₂Cl₂ (0.9 mL) and ethylenediamine (0.9 mL) was added. The reaction mixture was stirred at room temperature for 2 h then H₂O and EtOAc were added. The resultant suspension was filtered, rinsing with H₂O and EtOAc and dried under high vacuum to afford 55 mg (85%) of 2-cyclopropyl-5H-pyrrolo[2,3-b]pyrazine-7-carboxylic acid cyclohexylamide as a white solid. MS: (M+H)⁺=285; mp>300.0.

Example 18

2-Cyclopropyl-5H-pyrrolo[2,3-b]pyrazine-7-carboxylic acid cyclopentylamide

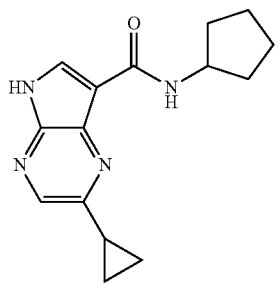

Prepared according to the procedure outlined in Example 17 substituting cyclopentylamine for cyclohexylamine in step 1. MS: (M+H)⁺=271; mp>300.0.

Example 19

2-Cyclopropyl-5H-pyrrolo[2,3-b]pyrazine-7-carboxylic acid ((cis)-2-cyano-cyclopentyl)-amide

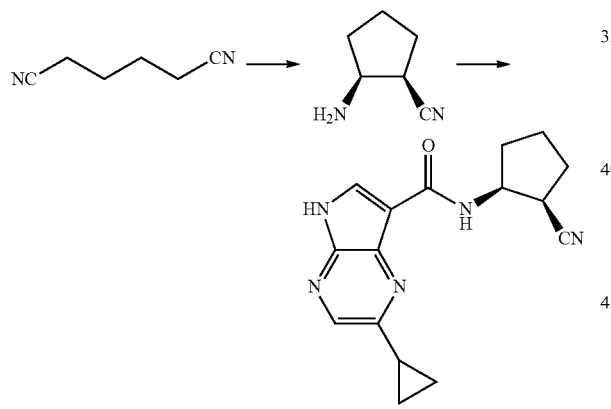

Step 1

To a suspension of sodium hydride (60% in mineral oil, 1.54 g, 38.6 mmol) in THF (70 mL) at room temperature was slowly added adiponitrile (4.0 mL, 35.1 mmol). The reaction mixture was heated at reflux overnight then cooled to room temperature, quenched with water, and extracted with EtOAc (2×). The combined organic layers were dried over MgSO₄ and concentrated. The residue was triturated with hexanes to afford 3.9 g of 2-amino-cyclopent-1-enecarbonitrile as an orange solid.

Step 2

A round-bottomed flask was charged with acetic acid (16 mL) and cooled to 0° C. Sodium borohydride (0.57 g, 15 mmol) was carefully added and the reaction was stirred until gas evolution has ceased. Then added 2-amino-cyclopent-1-enecarbonitrile (0.54 g, 5.0 mmol) and the reaction mixture was stirred at room temperature for 3 h. The solvent was evaporated and the residue was dissolved in CH₂Cl₂ and washed with saturated aqueous Na₂CO₃. The aqueous layer was back-extracted with CH₂Cl₂ and the combined organics were dried over Na₂SO₄ and concentrated to provide 309 mg (56%) of 2-amino-cyclopentanecarbonitrile as a yellow oil. NMR analysis revealed an ~5:1 mixture of cis and trans isomers. The material was used without further purification.

Step 3

2-Cyclopropyl-5H-pyrrolo[2,3-b]pyrazine-7-carboxylic acid ((cis)-2-cyano-cyclopentyl)-amide was prepared according to the procedure outlined in Example 1, steps 4-5 substituting 2-amino-cyclopentanecarbonitrile for 2-(1-amino-cyclopentyl)-propan-2-ol hydrochloride in step 4. MS: (M+H)⁺=296; mp>300.0.

Example 20

2-Cyclopropyl-5H-pyrrolo[2,3-b]pyrazine-7-carboxylic acid (1-cyanomethyl-cyclopentyl)-amide

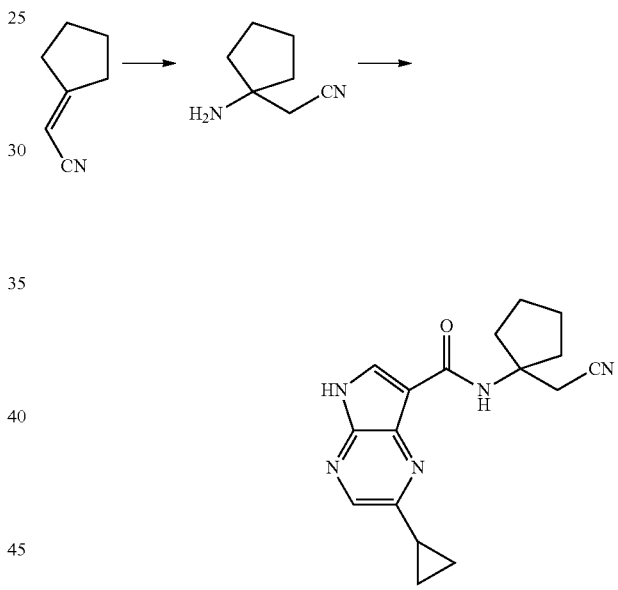

Step 1

Cyclopentylideneacetonitrile was prepared according to the procedure found in *J. Org. Chem.* 1990, 55, 4381.

Step 2

A solution of cyclopentylideneacetonitrile (1.4 g, 13.0 mmol) in 29% aqueous ammonia (15 mL) and MeOH (5 mL) in a sealed pressure tube was heated at 100° C. for 24 h. The reaction mixture was cooled to room temperature and concentrated. The residue was purified by chromatography over 60 g SiO₂ with MeOH/CH₂Cl₂ (gradient: 0-10% MeOH) to afford 0 88 g (54%) of (1-amino-cyclopentyl)-acetonitrile as a yellow oil.

Step 3

2-Cyclopropyl-5H-pyrrolo[2,3-b]pyrazine-7-carboxylic acid (1-cyanomethyl-cyclopentyl)-amide was prepared according to the procedure outlined in Example 1, steps 4-5 substituting (1-amino-cyclopentyl)-acetonitrile for 2-(1-amino-cyclopentyl)-propan-2-ol hydrochloride in step 4. MS: (M+H)$^+$=310; mp=280.0-281.0.

Example 21

2-Cyclopropyl-5H-pyrrolo[2,3-b]pyrazine-7-carboxylic acid (2,2-dimethyl-cyclohexyl)-amide

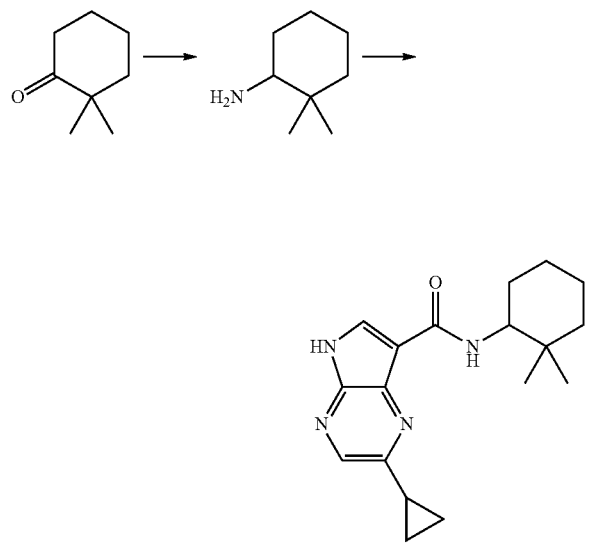

Step 1

In a 50 mL flask 2,2-dimethylcyclohexanone (0.50 g, 4.0 mmol) was dissolved in EtOH (10 mL). Hydroxylamine hydrochloride (1.04 g, 15.0 mmol), H$_2$O (4 mL), and 20% aqueous NaOH (4 mL) were added and the reaction mixture was heated at reflux for 2 d then cooled to room temperature overnight. The solvent was removed under reduced pressure. The residue was taken up in H$_2$O and filtered to collect 203 mg (36%) of (E/Z)-2,2-dimethylcyclohexanone oxime as a white solid. The filtrate was extracted with CH$_2$Cl$_2$ (2×). The combined organics were dried over Na$_2$SO$_4$ and concentrated to afford a further 34 mg (6%) of product as a white solid.

Step 2

In a dry 50 mL 3-neck round-bottomed flask, 2,2-dimethylcyclohexanone oxime (0.235 g, 1.66 mmol) was dissolved in THF (10 mL). Lithium aluminum hydride (1.0 M solution in THF, 4.0 mL, 4.0 mmol) was added dropwise over 15 min at room temperature. The reaction mixture was stirred at 60° C. overnight then cooled to room temperature and carefully quenched with 10 mL of saturated aqueous Rochelle-salt solution. The biphasic mixture was stirred at room temperature overnight then extracted with 2×50 mL of CH$_2$Cl$_2$. The combined organic layers were dried over Na$_2$SO$_4$, filtered, and concentrated to provide 151 mg (71%) of 2,2-dimethyl-cyclohexylamine as a yellow oil which was used without further purification.

Step 3

2-Cyclopropyl-5H-pyrrolo[2,3-b]pyrazine-7-carboxylic acid (2,2-dimethyl-cyclohexyl)-amide was prepared according to the procedure outlined in Example 1, steps 4-5 substituting 2,2-dimethylcyclohexylamine for 2-(1-amino-cyclopentyl)-propan-2-ol hydrochloride in step 4. MS: (M+H)$^+$=313; mp=295.0-297.0.

Example 22

2-Cyclopropyl-5H-pyrrolo[2,3-b]pyrazine-7-carboxylic acid (2,2-dimethyl-cyclopentyl)-amide

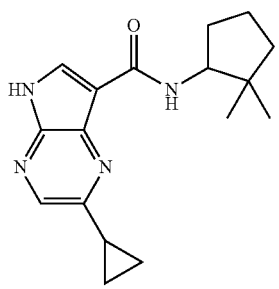

Prepared according to the procedure outlined in Example 21 substituting 2,2-dimethylcyclopentanone for 2,2-dimethylcyclohexanone in step 1. MS: (M+H)$^+$=299; mp>300.0.

Example 23

2-Cyclopropyl-5H-pyrrolo[2, 3-1)]pyrazine-7-carboxylic acid (1-methanesulfonyl-4,4-dimethyl-piperidin-3-yl)-amide Step 1

To a solution of 4,4-dimethylpiperidine-2,6-dione (2.0 g, 14.2 mmol) in acetone (50 mL) was added K$_2$CO$_3$ (3.92 g, 28.3 mmol) followed by (bromomethyl)benzene (1.85 mL, 15.6 mmol). The reaction mixture was heated at 50° C. for 4 h then cooled to room temperature and stirred overnight. The thick white precipitate present was removed via filtration, rinsing with acetone. The filtrate was concentrated and purified by SiO$_2$ chromatography (10% to 50% EtOAc/hexanes) to afford 3.0 g (92%) of 1-benzyl-4,4-dimethylpiperidine-2,6-dione as a white solid.

Step 2

To a solution of 1-benzyl-4,4-dimethylpiperidine-2,6-dione (1.00 g, 4.32 mmol) in THF (20 mL) at −78° C. was slowly added LiHMDS (1.0M in THF, 4.8 mL, 4.8 mmol). The resulting thick white slurry was stirred at −78° C. for 20 min then isopentyl nitrite (0.70 mL, 5.20 mmol) was added dropwise which caused a bright orange color to appear. The reaction mixture was stirred at −78° C. for 30 min then gradually warmed to room temperature over 1 h and quenched with saturated aqueous NH$_4$Cl. The biphasic mixture was stirred vigorously for 5 min then diluted with H$_2$O and extracted with EtOAc (2×). The combined organics were dried over MgSO$_4$ and concentrated. The crude residue was purified by SiO$_2$ chromatography (20% to 50% EtOAc/hexanes) to isolate first 340 mg (30%) of (Z)-1-benzyl-4,4-dimethylpiperidine-2,3,6-trione 3-oxime as a white solid followed by 280 mg (25%) of (E)-1-benzyl-4,4-dimethylpiperidine-2,3,6-trione 3-oxime as a white solid.

Step 3

To a solution of (Z)-1-benzyl-4,4-dimethylpiperidine-2,3,6-trione 3-oxime (490 mg, 1.88 mmol) in THF (5 mL) at 0° C. was slowly added LiAlH$_4$ (1.0M in THF, 9.4 mL, 9.4 mmol). After the addition, the reaction mixture was warmed to room temperature and stirred for 2 h then heated at 60° C. overnight. The reaction mixture was cooled to 0° C. and carefully quenched by portionwise addition of solid Na$_2$SO$_4$.10H$_2$O until gas evolution had ceased. The mixture was diluted with EtOAc and stirred vigorously at room temperature for 1 h then filtered, rinsing with EtOAc and MeOH. The filtrate was concentrated and the residue was purified by SiO$_2$ chromatography (0% to 10% MeOH/CH$_2$Cl$_2$ (0.5% NH$_4$OH)) to afford 210 mg (51%) of 1-benzyl-4,4-dimethylpiperidin-3-amine as a red oil.

Step 4

In a 25 mL flask were combined 2-cyclopropyl-5-((2-(trimethylsilyl)ethoxy)methyl)-5H-pyrrolo[2,3-b]pyrazine-7-carboxylic acid (150 mg, 0.45 mmol), 1-benzyl-4,4-dimethylpiperidin-3-amine (147 mg, 0.68 mmol), and HATU (188 mg, 0.50 mmol). Then added DMF (3 mL) followed by N,N-diisopropylethylamine (0.24 mL 1.35 mmol). The yellow reaction mixture was stirred at room temperature for 3 h then quenched with H$_2$O and extracted with EtOAc (3×). The combined organics were washed with H$_2$O (3×), dried over MgSO$_4$ and concentrated. The crude residue was purified by SiO$_2$ chromatography (30% to 80% EtOAc/hexanes) to afford 197 mg (82%) of N-(1-benzyl-4,4-dimethylpiperidin-3-yl)-2-cyclopropyl-5-(2-(trimethylsilyl)ethoxy)methyl)-5H-pyrrolo[2,3-b]pyrazine-7-carboxamide as a white foam.

Step 5

To a solution of N-(1-benzyl-4,4-dimethylpiperidin-3-yl)-2-cyclopropyl-542-(trimethylsilyl)ethoxy)methyl)-5H-pyrrolo[2,3-b]pyrazine-7-carboxamide (197 mg, 0.37 mmol) in MeOH (10 mL) was added 20% Pd(OH)$_2$ on carbon (40 mg, 0.06 mmol). The reaction mixture was stirred under an atmosphere of H$_2$ (1 atm) for 5 h then filtered over Celite, rinsing with EtOAc. The filtrate was concentrated to afford an off-white foam which was dissolved in CH$_2$Cl$_2$ (6 mL) and cooled to 0° C. then added triethylamine (77 μL, 0.55 mmol) followed by methanesulfonyl chloride (32 μL, 0.41 mmol,). The reaction mixture was stirred at 0° C. for 2.5 h then quenched with H$_2$O and extracted with CH$_2$Cl$_2$. The combined organics were dried over MgSO$_4$ and concentrated. The crude residue was purified by chromatography (50% to 90% EtOAc/hexanes) to isolate 193 mg (74%) of 2-cyclopropyl-N-(4,4-dimethyl-1-(methylsulfonyl)piperidin-3-yl)-5-((2-(trimethylsilyl)ethoxy)methyl)-5H-pyrrolo[2,3-b]pyrazine-7-carboxamide as a white foam.

Step 6

To a solution of 2-cyclopropyl-N-(4,4-dimethyl-1-(methylsulfonyl)piperidin-3-yl)-5-((2-(trimethylsilyl)ethoxy)methyl)-5H-pyrrolo[2,3-b]pyrazine-7-carboxamide (143 mg, 0.27 mmol) in CH$_2$Cl$_2$ (5 mL) was added TFA (2.0 mL, 26.0 mmol). The yellow reaction mixture was stirred for 3 h then concentrated The residue was redissolved in CH$_2$Cl$_2$ (5 mL) and ethylenediamine (0.5 mL, 7.4 mmol) was added. The reaction mixture was stirred at for 1 h then concentrated. The residue was purified by SiO$_2$ chromatography (50% to 100% EtOAc/hexanes to 5% MeOH/EtOAc) to isolate 66 mg (62%) of 2-cyclopropyl-5H-pyrrolo[2,3-b]pyrazine-7-carboxylic acid (1-methanesulfonyl-4,4-dimethyl-piperidin-3-yl)-amide as a white solid. MS: (M+H)$^+$=392.

Example 24

2-Cyclopropyl-5H-pyrrolo[2,3-b]pyrazine-7-carboxylic acid (4,4-dimethyl-tetrahydro-furan-3-yl)-amide

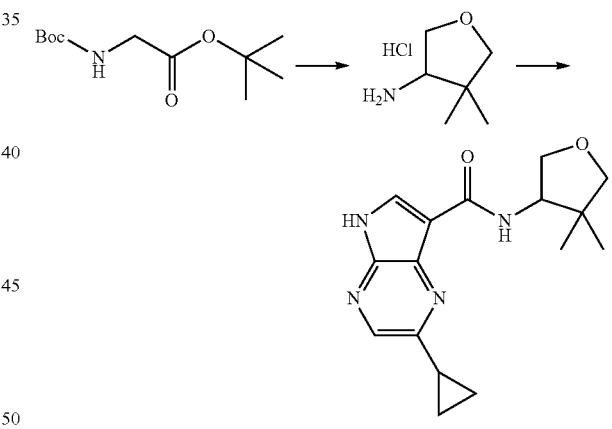

Step 1 tert-Butoxycarbonylamino-acetic acid tert-butyl ester (1.93 g, 8.35 mmol) was dissolved in 70 mL of carbon tetrachloride. N-bromosuccinimide (1.6 g, 9.19 mmol) was added and the reaction was brought to reflux. After 2 h the flask was cooled to 0° C., filtered and evaporated to approximately 2.7 g of crude bromo-tert-butoxycarbonylamino-acetic acid tert-butyl ester which was used directly in the next step.

Step 2

Bromo-tert-butoxycarbonylamino-acetic acid tert-butyl ester (1.5 g, 4.8 mmol) was dissolved in 40 mL of dichloromethane and then cooled in a dry ice/acetone bath. A solution of methyl trimethylsilyl dimethylketene acetal (1.9 mL, 9.6 mmol) in dichloromethane (5 mL) was added, followed by slow addition of a solution of titanium (IV) chloride (0.57 mL, 5.28 mmol) in dichloromethane (5 mL), and then a solution of triethylamine (0.73 mL, 5.28 mmol) in dichloromethane (10 mL). The reaction mixture was warmed to room temperature with stirring over 16 h. An aqueous solution of citric acid (~11 g/100 mL) was added and the reaction mixture briefly stirred. The layers were separated and the aqueous layer was extracted once more with dichloromethane. The combined dichloromethane layers were washed with sodium bicarbonate solution and dried over sodium sulfate. After evaporation, the residue was purified by silica gel chromatography (ethyl acetate/hexanes) to give 206 mg (13%) of 3-tert-butoxycarbonylamino-2,2-dimethyl-succinic acid 4-tert-butyl ester 1-methyl ester.

Step 3

A mixture of 3-tert-butoxycarbonylamino-2,2-dimethyl-succinic acid 4-tert-butyl ester 1-methyl ester and 3-tert-butoxycarbonylamino-2,2-dimethyl-succinic acid dimethyl ester (0.47 g, 1.53 mmol) was dissolved in dichloromethane (3 mL) and cooled to −78° C. Diisobutylaluminum hydride (3.4 mL of a 1M dichloromethane solution, 3.4 mmol) was slowly added. The reaction mixture was warmed to room temperature with stirring over 16 h. Additional diisobutylaluminum hydride (a total of 6.8 mL of a 1M solution, 6.8 mmol) was added portionwise over the next 24 h until thin layer chromatography indicated the starting material was consumed. Aqueous ammonium chloride solution and ethyl acetate were added to the reaction, the layers were separated and the aqueous layer was extracted once more with ethyl acetate. The combined organic layers were washed with sodium chloride solution and dried over sodium sulfate. After evaporation, the residue was purified by silica gel chromatography (ethyl acetate/hexanes) to give 104 mg (29%) of (3-hydroxy-1-hydroxymethyl-2,2-dimethyl-propyl)-carbamic acid tert-butyl ester.

Step 4

(3-Hydroxy-1-hydroxymethyl-2,2-dimethyl-propyl)-carbamic acid tert-butyl ester (104 mg, 0.44 mmol) was dissolved in dichloromethane (2.2 mL). Triphenylphosphine (0.115 g, 0.44 mmol) was added followed by azodiethylcarboxylate (0.16 mL, 0.88 mmol). After 30 min additional triphenylphosphine (0.115 g, 0.44 mmol) and azodiethylcarboxylate (0.16 mL, 0.88 mmol) were added and the reaction mixture was stirred for 72 h. The solvent was evaporated and the residue purified by silica gel chromatography (ethyl acetate/hexanes) to give 70 mg (74%) of (4,4-dimethyl-tetrahydro-furan-3-yl)-carbamic acid tert-butyl ester.

Step 5

(4,4-Dimethyl-tetrahydro-furan-3-yl)-carbamic acid tert-butyl ester (70 mg, 0.32 mmol) was dissolved in 3 mL of cold 4M HCl/dioxane and gradually warmed to room temperature with stirring. After the starting material was judged to be consumed by thin layer chromatography, the reaction mixture was concentrated to afford 4,4-dimethyl-tetrahydro-furan-3-ylamine hydrochloride which was used with further purification.

Step 6

2-Cyclopropyl-5H-pyrrolo[2,3-b]pyrazine-7-carboxylic acid (4,4-dimethyl-tetrahydro-furan-3-yl)-amide was prepared according to the procedure outlined in Example 1, steps 4-5 substituting 4,4-dimethyl-tetrahydro-furan-3-ylamine hydrochloride for 2-(1-amino-cyclopentyl)-propan-2-ol hydrochloride in step 4. MS: (M+H)⁺=301; mp>300; Elem. Anal: calculated C, 63.98; H, 6.71; N, 18.65, found C, 63.68; H, 6.57; N, 18.30.

Example 25

2-Cyclopropyl-5H-pyrrolo[2,3-b]pyrazine-7-carboxylic acid ((trans)-2-hydroxy-2-methyl-cyclopentyl)-amide

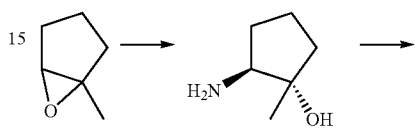

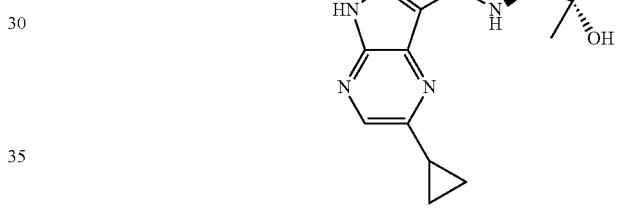

Step 1

In a microwave vial were placed methyl-1,2-cyclopentene oxide (0.50 g, 5.1 mmol), 4-methoxybenzylamine (1.5 mL, 11.5 mmol) and water (1.5 mL). The vial was sealed and the biphasic mixture was heated in a microwave reactor at 130° C. for 1 h. The reaction was diluted with water and extracted with CH₂Cl₂. the organic layer was dried over MgSO₄ and concentrated. The residue was purified by SiO₂ chromatography (0% to 8% MeOH/CH₂Cl₂ (0.5% NH₄OH)) to afford 0.69 g (57%) of trans-2-(4-methoxybenzylamino)-1-methyl-cyclopentanol as a white solid.

Step 2

To a solution of trans-2-(4-methoxybenzylamino)-1-methyl-cyclopentanol (0.32 g, 1.36 mmol) in MeOH (10 mL) was added 20% Pd(OH)₂ on carbon (40 mg). The reaction mixtures was stirred under an atmosphere of H₂ (balloon) for 16 h then filtered over Celite, rinsing with EtOAc. The filtrate was concentrated to afford trans-2-amino-1-methyl-cyclopentanol as an off-white solid which was used without further purification.

Step 3

2-Cyclopropyl-5H-pyrrolo[2,3-b]pyrazine-7-carboxylic acid ((trans)-2-hydroxy-2-methyl-cyclopentyl)-amide was prepared according to the procedure outlined in Example 1, steps 4-5 substituting trans-2-amino-1-methyl-cyclopentanol

Example 26

2-Cyclopropyl-5H-pyrrolo[2,3-b]pyrazine-7-carboxylic acid (tetrahydro-pyran-3-yl)-amide

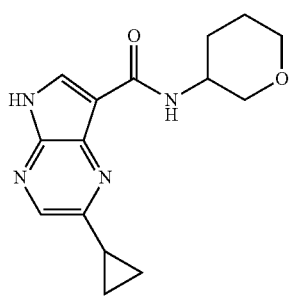

Prepared according to the procedure outlined in Example 1, steps 4-5 substituting tetrahydro-pyran-3-ylamine for 2-(1-amino-cyclopentyl)-propan-2-ol hydrochloride in step 4. MS: (M+H)⁺=287; mp>300.0.

Example 27

2-Cyclopropyl-5H-pyrrolo[2,3-b]pyrazine-7-carboxylic acid (3-cyano-phenyl)-amide

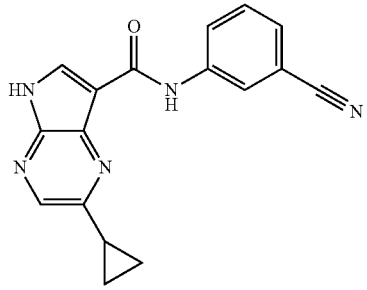

Step 1

2-Cyclopropyl-5-((2-(trimethylsilyl)ethoxy)methyl)-5H-pyrrolo[2,3-b]pyrazine-7-carboxylic (100 mg, 0.30 mmol) was dissolved in acetonitrile (2 mL). N,N-diisopropylethylamine (0.15 mL, 0.9 mmol), O-benzotriazol-1-yl-N,N,N',N'-tetramethyluronium tetrafluoroborate (106 mg, 0.33 mmol) and 3-aminobenzonitrile (35 mg, 0.30 mmol) were added and the reaction mixture was stirred overnight. Water and ethyl acetate were added and the layers were separated. The aqueous layer was extracted once more with ethyl acetate and the combined organic layers were washed with sodium chloride solution, dried over sodium sulfate and concentrated. The residue was purified by silica gel chromatography (EtOAc/hexanes) to give 113 mg (85%) of 2-cyclopropyl-5-(2-trimethylsilanyl-ethoxymethyl)-5H-pyrrolo[2,3-b]pyrazine-7-carboxylic acid (3-cyano-phenyl)-amide.

Step 2

To a solution of 2-cyclopropyl-5-(2-trimethylsilanyl-ethoxymethyl)-5H-pyrrolo[2,3-b]pyrazine-7-carboxylic acid (3-cyano-phenyl)-amide (113 mg, 0.26 mmol) in CH₂Cl₂ (2.6 mL) was added trifluoroacetic acid (1 mL). Stirred at room temperature for 2 h then neutralized with aqueous NaHCO₃ and extracted with EtOAc. The organic layer was washed with brine, dried over Na₂SO₄ and concentrated. The residue was dissolved in EtOH and NaOAc (0.7 g) was added. The reaction mixture was stirred at 60° C. overnight then cooled to room temperature and water and EtOAc were added. The aqueous layer was extracted with EtOAc and the combined organics were washed with brine, dried over Na₂SO₄ and concentrated. The residue was purified by silica gel chromatography (MeOH/CH₂Cl₂) to give 22 mg (28%) of 2-cyclopropyl-5H-pyrrolo[2,3-b]pyrazine-7-carboxylic acid (3-cyano-phenyl)-amide. MS: (M+H)⁺=304; mp=272.0-274.0.

Example 28

2-Cyclopropyl-5H-pyrrolo[2,3-b]pyrazine-7-carboxylic acid (3-trifluoromethyl-phenyl)-amide

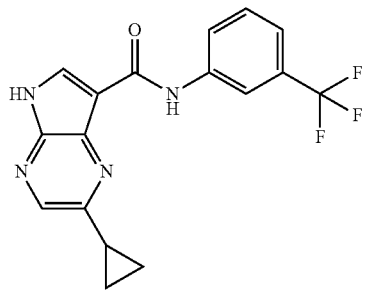

Prepared according to the procedure outlined in Example 27 substituting 3-aminobenzotrifluoride for 3-aminobenzonitrile in step 1. MS: (M+H)⁺=347; mp=271.1-272.9.

Example 29

2-Cyclopropyl-5H-pyrrolo[2,3-b]pyrazine-7-carboxylic acid (5-cyano-2-methyl-phenyl)-amide

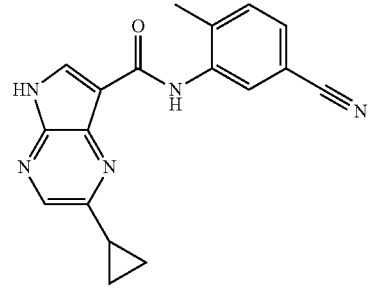

Prepared according to the procedure outlined in Example 27 substituting 3-amino-4-methyl-benzonitrile for 3-aminobenzonitrile in step 1. MS: (M+H)⁺=318; mp=280.0-284.0.

Example 30

2-Cyclopropyl-5H-pyrrolo[2,3-b]pyrazine-7-carboxylic acid (4-hydroxymethyl-tetrahydro-pyran-4-yl)-amide

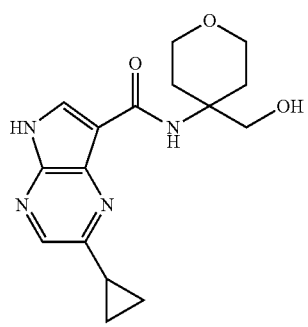

Step 1

To a solution of 2-cyclopropyl-5-(2-trimethylsilanyl-ethoxymethyl)-5H-pyrrolo[2,3-b]pyrazine-7-carboxylic acid (0.20 g, 0.59 mmol) in CH$_2$Cl$_2$ (5 mL) was added EDC (0.14 g, 0.72 mmol), 4-(dimethylamino)pyridine (0.088 g, 0.72 mmol), and (4-aminotetrahydropyran-4-yl)-methanol (0.094 g, 0.72 mmol). The reaction mixture was stirred at room temperature overnight then diluted with H$_2$O and extracted with CH$_2$Cl$_2$. The combined organics were washed with brine, dried over Na$_2$SO$_4$ and concentrated. The residue was purified by SiO$_2$ chromatography (60% EtOAc/hexanes) to obtain 0.15 g (57%) of 2-cyclopropyl-5-(2-trimethylsilanyl-ethoxymethyl)-5H-pyrrolo[2,3-b]pyrazine-7-carboxylic acid (4-hydroxymethyl-tetrahydro-pyran-4-yl)-amide as an oil.

Step 2

To a solution of 2-cyclopropyl-5-(2-trimethylsilanyl-ethoxymethyl)-5H-pyrrolo[2,3-b]pyrazine-7-carboxylic acid (4-hydroxymethyl-tetrahydro-pyran-4-yl)-amide (0.15 g, 0.33 mmol) in CH$_2$Cl$_2$ (7.5 mL) was added trifluoroacetic acid (1.5 mL). The reaction mixture was stirred at room temperature overnight then concentrated. The residue was dissolved in MeOH (10 mL) and H$_2$O (1 mL) and Et$_3$N (2 mL) were added. The reaction mixture was stirred at room temperature overnight then concentrated. The residue was triturated with Et$_2$O to afford 96 mg (92%) of 2-cyclopropyl-5H-pyrrolo[2,3-b]pyrazine-7-carboxylic acid (4-hydroxymethyl-tetrahydro-pyran-4-yl)-amide as an off-white solid. MS: (M+H)$^+$=317; mp=294.0-296.0.

Example 31

2-Cyclopropyl-5H-pyrrolo[2,3-b]pyrazine-7-carboxylic acid (tetrahydro-pyran-4-yl)-amide

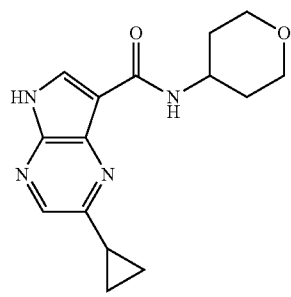

Prepared according to the procedure outlined in Example 30 substituting 4-aminotetrahydropyran for (4-aminotetrahydropyran-4-yl)-methanol in step 1. MS: (M+H)$^+$=287; mp>300.0.

Example 32

2-Cyclopropyl-5H-pyrrolo[2,3-b]pyrazine-7-carboxylic acid (1-hydroxymethyl-cyclopentyl)-amide

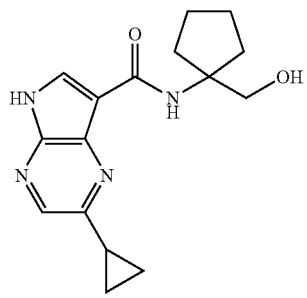

Prepared according to the procedure outlined in Example 30 substituting 1-amino-1-cyclopentane-methanol for (4-aminotetrahydropyran-4-yl)-methanol in step 1. MS: (M+H)$^+$=317; mp=272.0-274.0.

Example 33

2-Cyclopropyl-5H-pyrrolo[2,3-b]pyrazine-7-carboxylic acid (1-cyano-cyclopropyl)-amide

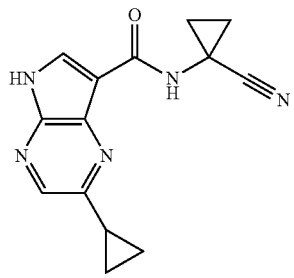

Prepared according to the procedure outlined in Example 30 substituting 1-amino-cyclopropanecarbonitrile for (4-aminotetrahydropyran-4-yl)-methanol in step 1. MS: (M+H)$^+$=268; mp>300.0.

Example 34

2-Cyclopropyl-5H-pyrrolo[2,3-b]pyrazine-7-carboxylic acid (2,2-dimethyl-tetrahydrofuran-3-yl)-amide

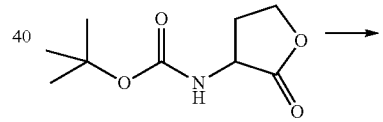

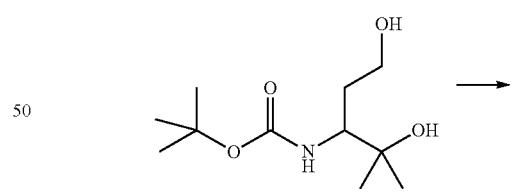

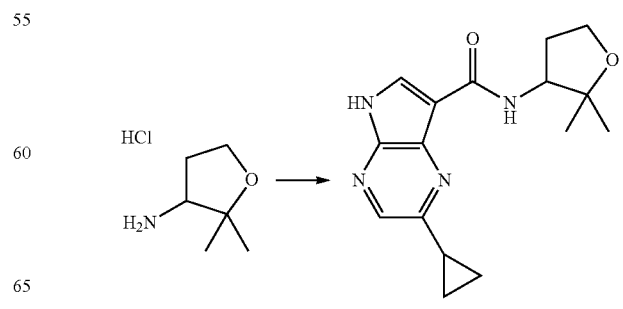

Step 1

To a solution of tert-butyl-(tetrahydro-2-oxo-3-furanyl)-carbamate (2.1 g, 10.4 mmol) in THF (12 mL) at 0° C. was slowly added methylmagnesium bromide (3.0 M in Et₂O, 14.5 mL, 43.5 mmol). The reaction mixture was stirred at room temperature overnight then carefully quenched with water. The mixture was filtered through Celite, rinsing with CH₂Cl₂. The filtrate was washed with brine, dried over sodium sulfate and concentrated to afford 1.65 g (68%) of 2-hydroxy-1-(2-hydroxy-ethyl)-2-methyl-propyl]-carbamic acid tert-butyl ester as a white solid which was used without further purification.

Step 2

To a solution of 2-hydroxy-1-(2-hydroxy-ethyl)-2-methyl-propyl]-carbamic acid tert-butyl ester (498 mg, 2.13 mmol) and triethylamine (0.45 mL, 3.23 mmol) in CH₂Cl₂ (21 mL) at 0° C. was added methanesulfonyl chloride (0.20 mL, 2.58 mmol). The reaction mixture was allowed to warm to room temperature and stirred for 2 h. The reaction was washed with 3 M aqueous NaOH, water, and brine then dried over Na₂SO₄ and concentrated to afford 627 mg of methanesulfonic acid 3-tert-butoxycarbonylamino-4-hydroxy-4-methyl-pentyl ester as a pale yellow oil which was used without further purification.

Step 3

To a solution of methanesulfonic acid 3-tert-butoxycarbonylamino-4-hydroxy-4-methyl-pentyl ester (627 mg, 2.0 mmol, crude from step 2) in NMP (5 mL) was added sodium cyanide (0.98 g, 20 mmol). The reaction mixture was heated at 85° C. overnight then cooled to room temperature and partitioned between water and diethyl ether. The organic layer was washed with brine, dried over Na₂SO₄ and concentrated. The residue was purified by SiO₂ chromatography (20% to 50% EtOAc/hexanes) to afford 268 mg (62%) of (2,2-dimethyl-tetrahydro-furan-3-yl)-carbamic acid tert-butyl ester as a white solid.

Step 4

(2,2-Dimethyl-tetrahydro-furan-3-yl)-carbamic acid tert-butyl ester (266 mg, 1.10 mmol) was dissolved in a solution of HCl in MeOH (pre-generated from MeOH (8 mL) and acetyl chloride (2 mL)) and stirred at room temperature overnight. The reaction mixture was concentrated to afford 193 mg of 2,2-dimethyl-tetrahydrofuran-3-ylamine hydrochloride as a hydroscopic white solid which was used without further purification.

Step 5

2-Cyclopropyl-5H-pyrrolo[2,3-b]pyrazine-7-carboxylic acid (2,2-dimethyl-tetrahydrofuran-3-yl)-amide was prepared according to the procedure outlined in Example 30 substituting 2,2-dimethyl-tetrahydrofuran-3-ylamine hydrochloride for (4-aminotetrahydropyran-4-yl)-methanol in step 1. MS: (M+H)⁺=301; mp>300.0.

Example 35

2-Cyclopropyl-5H-pyrrolo[2,3-b]pyrazine-7-carboxylic acid ((3R,4S)-3-hydroxy-tetrahydro-pyran-4-yl)-amide

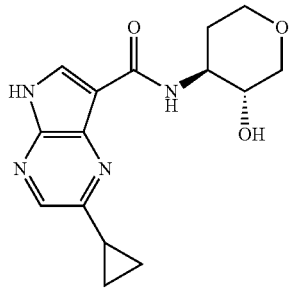

Prepared according to the procedure outlined in Example 1, steps 4-5 substituting (3R,4S)-4-amino-tetrahydro-pyran-3-ol for 2-(1-amino-cyclopentyl)-propan-2-ol hydrochloride in step 4. MS: (M+H)⁺=303.

Example 36

2-Cyclopropyl-5H-pyrrolo[2,3-b]pyrazine-7-carboxylic acid (1-cyclopropane carbonyl-cyclopentyl)-amide

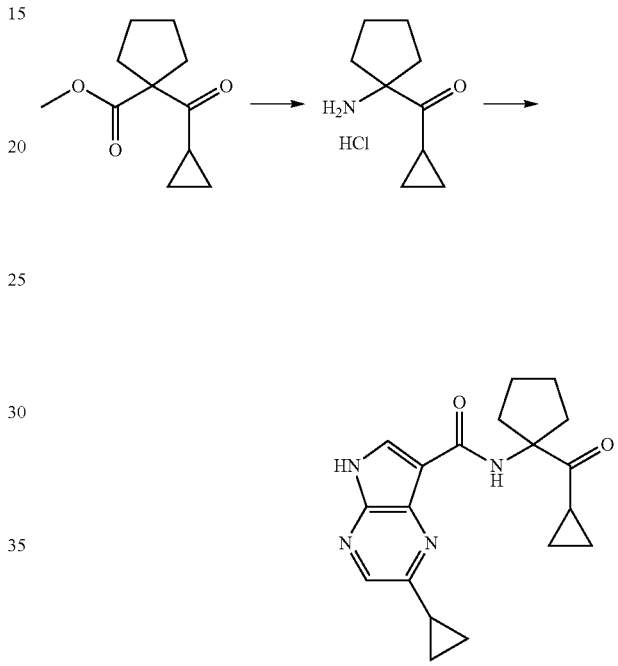

Step 1

To a solution of methyl 3-cyclopropyl-3-oxopropanoate (2.0 g, 14 mmol) in DMF (70 mL) was added sodium hydride (60% in mineral oil, 1.41 g, 35 mmol). The reaction mixture was stirred for 10 min then 1,4-dibromobutane (1.85 mL, 15 mmol) was slowly added. The reaction mixture was stirred for 2.5 h then carefully quenched with water and extracted with diethyl ether (2×). The combined organics were washed with water (2×) and brine then dried over Na₂SO₄ and concentrated. The residue was purified by chromatography over 60 g SiO₂ (0% to 10% EtOAc/hexanes) to afford 0.63 g (23%) of 1-cyclopropanecarbonyl-cyclopentane carboxylic acid methyl ester as a colorless oil.

Step 2

To a solution of 1-cyclopropanecarbonyl-cyclopentane carboxylic acid methyl ester (0.62 g, 3.1 mmol) in EtOH (10 mL) were added LiOH.H₂O (0.53 g, 12.6 mmol) and water (3 mL). The reaction mixture was stirred at room temperature overnight then diluted with water and washed with Et₂O. The aqueous layer was acidified with conc. HCl to pH=2 then extracted with Et₂O (2×). The combined second organic extracts were dried over Na₂SO₄ and concentrated to afford 0.36 g (64%) of 1-cyclopropanecarbonyl-cyclopentane carboxylic acid as a pale yellow oil.

Step 3

To a solution of 1-cyclopropanecarbonyl-cyclopentane carboxylic acid (0.36 g, 2.0 mmol) in t-BuOH (10 mL) was added triethylamine (0.33 mL, 2.4 mmol) followed by diphenylphosphoryl azide (0.47 mL, 2.2 mmol). The reaction mixture was stirred at reflux for 6 h then cooled to room temperature and poured into saturated aqueous $NaHCO_3$. The aqueous layer was extracted with EtOAc (3×). The combined organics were dried over $Na_2SO_4$ and concentrated. The residue was purified by chromatography on 24 g $SiO_2$ (0% to 30% EtOAc/hexanes) to afford 63 mg (13%) of (1-cyclopropanecarbonyl-cyclopentyl)-carbamic acid tert-butyl ester as a white solid.

Step 4

In a 10 mL round-bottomed flask (1-cyclopropanecarbonyl-cyclopentyl)-carbamic acid tert-butyl ester (61 mg, 0.24 mmol) was dissolved in 1.0 M HCl solution in MeOH (1.5 mL, 1.5 mmol). The reaction mixture was stirred at room temperature overnight then concentrated under reduced pressure to afford 45 mg (98%) of (1-amino-cyclopentyl)-cyclopropyl-methanone hydrochloride as a white solid.

Step 5

2-Cyclopropyl-5 H-pyrrolo [2,3-b]pyrazine-7-carboxylic acid (1-cyclopropanecarbonyl-cyclopentyl)-amide was prepared according to the procedure outlined in Example 1, steps 4-5 substituting (1-amino-cyclopentyl)-cyclopropyl-methanone hydrochloride for 2-(1-amino-cyclopentyl)-propan-2-ol hydrochloride in step 4. MS: $(M+H)^+=339$; mp=296.0-299.0.

Example 37

2-Phenoxy-5H-pyrrolo[2,3-b]pyrazine-7-carboxylic acid cyclohexylamide

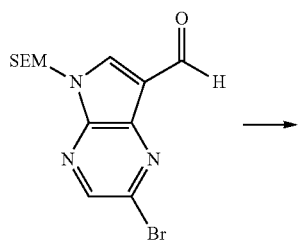

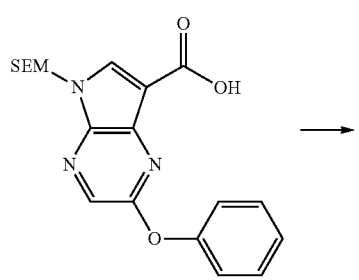

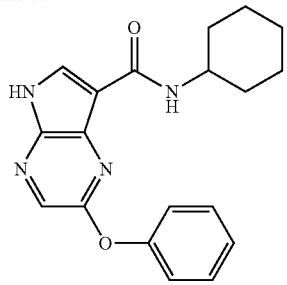

Step 1

A mixture of 2-bromo-5-(2-trimethylsilanyl-ethoxymethyl)-5H-pyrrolo[2,3-b]pyrazine-7-carbaldehyde (3.29 g, 9.23 mmol), phenol (1.04 g, 11.08 mmol), $K_3PO_4$ (3.92 g, 18.46 mmol), [2'-(di-tert-butyl-phosphanyl)-biphenyl-2-yl]-dimethyl-amine (0.157 g, 0.46 mmol), $Pd(OAc)_2$ (0.103 g, 0.46 mmol) and degassed toluene (50 mL) was stirred under nitrogen in a sealed tube at 150° C. overnight. The reaction mixture was cooled to room temperature and partitioned between ethyl acetate and water. The aqueous layer was extracted with ethyl acetate, and the combined organic layers were dried over $MgSO_4$, filtered and concentrated. The residue was purified by $SiO_2$ column chromatography (0-30% EtOAc/hexanes) to afford 2.09 g (61%) of 2-phenoxy-5-(2-trimethylsilanyl-ethoxymethyl)-5H-pyrrolo[2,3-b]pyrazine-7-carbaldehyde as a beige solid.

Step 2

A stock solution of Jones reagent (2.67 M) was prepared by carefully adding concentrated $H_2SO_4$ (2.3 mL) to $CrO_3$ (2.67 g) then diluting to 10 mL with $H_2O$. To a solution of 2-phenoxy-5-(2-trimethylsilanyl-ethoxymethyl)-5H-pyrrolo[2,3-b]pyrazine-7-carbaldehyde (2.35 g, 6.37 mmol) in acetone (75 mL) at 0° C. was added Jones reagent (5 mL, 13.4 mmol) dropwise. The reaction mixture was stirred at room temperature for 2 h then quenched with i-PrOH (2 mL), diluted with EtOAc, and filtered over Celite, rinsing with EtOAc. The filtrate was washed with cold water (3×) and brine then dried over $MgSO_4$ and concentrated. The residue was purified by $SiO_2$ column chromatography (30-70% EtOAc/hexanes) to provide 1.59 g (65%) of 2-phenoxy-5-(2-trimethylsilanyl-ethoxymethyl)-5H-pyrrolo[2,3-b]pyrazine-7-carboxylic acid as a light yellow solid.

Step 3

To a solution of 2-phenoxy-5-(2-trimethylsilanyl-ethoxymethyl)-5H-pyrrolo[2,3-b]pyrazine-7-carboxylic acid (0.115 g, 0.30 mmol), 4-dimethylaminopyridine (0.048 g, 0.39 mmol) and (3-dimethylamino-propyl)-ethyl-carbodiimide (0.075 g, 0.39 mmol) in $CH_2Cl_2$ (2 mL) was added a solution of cyclohexylamine (0.039 g, 0.39 mmol) in $CH_2Cl_2$ (0.5 mL). The reaction mixture was stirred at room temperature overnight, then quenched with water and extracted with ethyl acetate (3×). The organic layer was washed with water and saturated aqueous NaCl solution and dried over $MgSO_4$, filtered and concentrated to afford 2-phenoxy-5-(2-trimethylsilanyl-ethoxymethyl)-5H-pyrrolo[2,3-b]pyrazine-7-carboxylic acid cyclohexylamide which was used without further purification.

Step 4

To a solution of 2-phenoxy-5-(2-trimethylsilanyl-ethoxymethyl)-5H-pyrrolo[2,3-b]pyrazine-7-carboxylic acid cyclohexylamide from Step 3 in dichloromethane (0.7 mL) was added trifluoroacetic acid (0.7 mL). The reaction mixture was stirred at room temperature overnight then concentrated. The residue was stirred with THF (1 mL), water (0.5 mL), and Et₃N (0.5 mL) for 2 h then concentrated. The residue was partitioned between ethyl acetate and water and the aqueous layer was extracted with ethyl acetate. The combined organic layers were dried over MgSO₄ and concentrated. The residue was purified by SiO₂ column chromatography (0% to 80% EtOAc/hexanes) then triturated with Et₂O to provide 0.022 g (22%, 2 steps) of 2-phenoxy-5H-pyrrolo[2,3-b]pyrazine-7-carboxylic acid cyclohexylamide as a white solid. MS: (M+H)⁺=337; mp=255.0-257.0.

Example 38

2-(2,4-Difluoro-phenoxy)-5H-pyrrolo[2,3-b]pyrazine-7-carboxylic acid cyclohexylamide

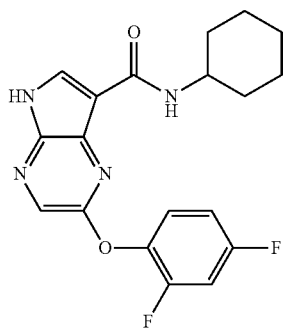

Prepared according to the procedure outlined in Example 37 substituting 2,4-difluorophenol for phenol in step 1. MS: (M+H)⁺=373; mp=245.0-247.0.

Example 39

2-(1-Ethyl-1H-pyrazol-4-yl)-5H-pyrrolo[2,3-b]pyrazine-7-carboxylic acid (2,2-dimethyl-cyclohexyl)-amide

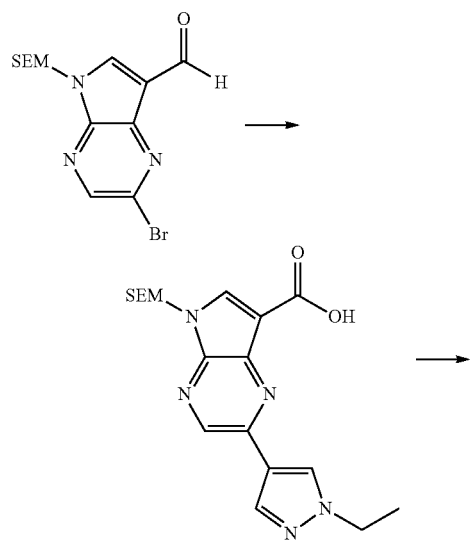

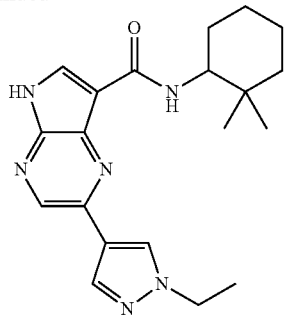

Step 1

To a solution of 2-bromo-5-((2-(trimethylsilyl)ethoxy)methyl)-5H-pyrrolo[2,3-b]pyrazine-7-carbaldehyde (1.33 g, 3.73 mmol) and 1-ethyl-4-(4,4,5,5-tetramethyl-1,3,2-dioxaborolan-2-yl)-1H-pyrazole (995 mg, 4.48 mmol) in 1,2-DME (20 mL) were added Pd(Ph₃P)₄ (0.22 g, 0.19 mmol) and 2.0 M aqueous K₂CO₃ (5.6 ml, 11.2 mmol). The reaction mixture was degassed by bubbling N₂ for 15 min then heated at 100° C. overnight. The resultant maroon reaction mixture was cooled and diluted with H₂O then extracted with EtOAc (2×). The combined organics were dried over MgSO₄ and concentrated. The crude residue was purified by SiO₂ chromatography (30% to 80% EtOAc/hexanes) to afford 1.12 g (81%) of 2-(1-ethyl-1H-pyrazol-4-yl)-5-(2-(trimethylsilyl)ethoxy)methyl)-5H-pyrrolo[2,3-b]pyrazine-7-carbaldehyde as a light orange-brown solid.

Step 2

To a solution of 2-(1-ethyl-1H-pyrazol-4-yl)-5-((2-(trimethylsilyl)ethoxy)methyl)-5H-pyrrolo[2,3-b]pyrazine-7-carbaldehyde (1.12 g, 3.01 mmol) in 1,4-dioxane (50 mL) and H₂O (10 mL) at 0° C. was added sulfamic acid (1.76 g, 18.1 mmol). Then added a solution of NaClO₂ (0.44 g, 3.92 mmol) and KH₂PO₄ (4.92 g, 36.2 mmol) in H₂O (30 mL) via dropping funnel over 15 min. The ice bath was removed and the yellow cloudy reaction mixture was stirred at room temperature for 2.5 h. The reaction mixture was diluted with H₂O and extracted with EtOAc (2×). The combined organic layers were dried over MgSO₄ and concentrated to an oily yellow solid which was triturated with 5% EtOAc/hexanes to afford 1.05 g (90%) of 2-(1-ethyl-1H-pyrazol-4-yl)-5-(2-(trimethylsilyl)ethoxy)methyl)-5H-pyrrolo[3,2-b]pyrazine-7-carboxylic acid as a light yellow solid.

Step 3

2-(1-Ethyl-1H-pyrazol-4-yl)-5H-pyrrolo[2,3-b]pyrazine-7-carboxylic acid (2,2-dimethyl-cyclohexyl)-amide was prepared according to the procedure outlined in Example 1, steps 4-5 substituting 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid and 2,2-dimethylcyclohexylamine [Example 21, steps 1-2] for 2-(1-amino-cyclopentyl)-propan-2-ol hydrochloride in step 4. MS: (M+H)⁺=367.

JAK Assay Information

Determination of IC₅₀ of Janus Kinase (JAK) Inhibition:
Enzymes and peptide substrate used are described below:
JAK1: Recombinant human kinase domain from Invitrogen (Cat # PV4774)
JAK3: Recombinant human kinase domain from Millipore (Cat # 14-629) or prepared.
JAK2: Recombinant human kinase domain from Millipore (Cat # 14-640)

Substrate: N-terminally biotinylated 14-mer peptide derived from activation loop of JAK1 with sequence of the peptide substrate: Biotin-KAIETDKEYYTVKD Assay conditions used are described below:

Assay Buffer: JAK Kinase Buffer: 50 mM Hepes [pH 7.2], 10 mM $MgCl_2$, 1 mM DTT, 1 mg/mL BSA. The assay is carried out in this buffer.

Assay Format The kinase activity of all three JAK kinases is measured using a radioactive, end-point assay and with trace amounts of $^{33}$P-ATP. The assays are carried out in 96-well polypropylene plates.

Experimental Method:

All concentrations are final in the reaction mixture and all incubations are carried at room temperature. Assay steps are described below:

1) Compounds are serially diluted in 100% DMSO typically at a 10× starting concentration of 1 mM. Final concentration of DMSO in the reaction is 10%.
2) Compounds are preincubated with enzyme (0.5 nM JAK3 (commercially available), 0.2 nM JAK3 (prepared), 1 nM JAK2, 5 nM JAK1) for 10 minutes.
3) Reactions are initiated by the addition of a cocktail of the two substrates (ATP and peptide premixed in the JAK Kinase Buffer). In the JAK2/JAK3 assays, ATP and the peptide are used at concentrations of 1.5 uM and 50 uM, respectively. JAK1 assay is carried out at an ATP concentration of 10 uM and a peptide concentration of 50 uM.
4) The duration of the assay for JAK2 and JAK3 is 20 minutes. JAK1 assay is carried out for 40 minutes. With all three enzymes, reactions are terminated by the addition of 0.5M EDTA to a final concentration of 100 mM.
5) 25 ul of terminated reactions are transferred to 150 ul of a 7.5% (v/v) slurry of streptavidin-coated sepharose beads in $MgCl_2$- and $CaCl_2$-free 1× Phosphate Buffered Saline containing 50 mM of EDTA in 96-well, 1.2 um MultiScreen-BV filter plates.
6) After a 30-minute incubation, the beads are washed under vacuum with the following buffers:
   a. 3 to 4 washes with 200 ul of 2M NaCl.
   b. 3 to 4 washes with 200 ul of 2M NaCl plus 1% (v/v) phosphoric acid.
   c. 1 wash with water.
7) Washed plates are dried in a 60° C. oven for between 1 to 2 hours.
8) 70 ul of Microscint 20 scintillation fluid is added to each well of filter plates and after at least 30 minutes of incubation, radioactive counts are measured in a Perkinelmer microplate scintillation counter.

Representative $IC_{50}$ results are in Table II below:

TABLE II

| Compound | $IC_{50}$ h-jak3-sf21-c |
|---|---|
| I-1 | 0.0420 |
| I-2 | 0.6738 |
| I-3 | 0.0442 |
| I-4 | 0.0053 |
| I-5 | 0.7347 |
| I-6 | 0.0156 |
| I-7 | 0.0011 |
| I-8 | 0.9631 |
| I-9 | 0.1567 |
| I-10 | 0.5238 |
| I-11 | 0.0129 |
| I-12 | 0.0497 |
| I-13 | 0.0427 |
| I-14 | 0.0389 |
| I-15 | 0.4233 |
| I-16 | 0.0098 |
| I-17 | 10.0000 |
| I-18 | 0.3418 |
| I-19 | 1.0443 |
| I-20 | 0.0354 |
| I-21 | 0.0962 |
| I-22 | 0.0052 |
| I-23 | 0.0133 |
| I-24 | 0.0080 |
| I-25 | 0.0100 |
| I-26 | 0.0263 |
| I-27 | 0.0173 |
| I-28 | 0.0220 |
| I-29 | 0.0732 |
| I-30 | 0.0555 |
| I-31 | 0.0037 |
| I-32 | 0.0011 |
| I-33 | 0.1529 |
| I-34 | 0.4242 |
| I-35 | 0.0021 |
| I-36 | 0.1674 |
| I-37 | 0.1196 |
| I-38 | 0.0742 |
| I-39 | 0.0003 |
| I-40 | 0.0502 |
| I-41 | 2.1575 |

SYK Assay Information

Determination of $IC_{50}$ of Spleen Tyrosine Kinase (Syk) Inhibition:

SYK kinase assay is a standard kinase assay adapted to a 96 well plate format. This assay is performed in 96-well format for $IC_{50}$ determination with 8 samples which represented 10 half log dilutions and a 40 μL reaction volume. The assay measures the incorporation of radio labeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)

Streptavidin coated beads: Streptavidin Sepharose TM, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.: 0.0005 μM.

Peptide 1: biotinylated peptide is derived from a naturally occurring phosphor-acceptor consensus sequence (Biotin-EPEGDYEEVLE), special order from QCB, stock solution 20 mM, final conc.: 5.0 μM.

ATP: Adenosine-5'-triphosphate 20 mM, (ROCHE Cat. No.: 93202720), final concentration: 20 μM Buffer: HEPES: 2-Hydroxyethyl piperazine-2-ethanesulfonic acid (Sigma™, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM MgCl$_2$×6H$_2$O: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM MgCl$_2$, 1 mM DTT, 0,1% BSA, pH 7.5

Bead wash buffer: 10 g/L PBS (Phosphate buffered saline) with 2M NaCl+ 1% phosphoric acid.

Experimental Method:

In 40 μL volume, 26 μL, of ADB diluted, purified recombinant human SYK360-635 [0.5 nM] was mixed with 4 μL of 10× concentrations of the test compounds, [usually 100 μM-0.003 μM] in [10%] DMSO and the mixture was incubated for 10 min at RT.

The kinase reaction was initiated by the addition of 10 μL 4× substrate cocktail containing the DYE peptide substrate [0 or 5 μM], ATP [20 μM] and $^{33}$PγATP [2 μCi/rxn]. After incubation at 30° C. for 15 min, the reaction was terminated by the transfer of 254, of the reaction sample to a 96 well 0.65 μm Millipore MADVNOB membrane/plate containing 200 μL 5 mM EDTA and 20% Streptavidine coated beads in PBS.

The unbound radionucleotides were washed under vacuum with 3×250 μL 2M NaCl; 2×250 μL 2M NaCl+1% phosphoric acid; 1×250 μL H$_2$O. After the last wash membrane/plates were transferred to an adaptor plate, heat dried for 15 min at 60° C., and 50 μL scintillation cocktail was added to each well and 4 h later the amount of radioactivity was counted in a top counter.

The percent inhibition was calculated based on the uninhibited enzyme rate:

(1) % Inhibition=100/(1+(IC$_{50}$/Inhibitor conc)$^n$)

(2) The IC$_{50}$ was calculated using a non-linear curve fit with XLfit software (ID Business Solution Ltd., Guilford, Surrey, UK).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I

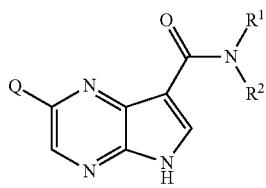

wherein:

$R^1$ is H or OH;

$R^2$ is phenyl, heterocycloalkyl, heteroaryl or cycloalkyl, each optionally substituted with one or more $R^{2'}$;

each $R^{2'}$ is independently hydroxy, halo, lower alkyl, lower alkenyl, lower alkynyl, lower haloalkyl, lower alkoxy, lower haloalkoxy, lower hydroxyalkyl, amino, lower alkylamino, lower dialkylamino, cyano, lower cyanoalkyl, cycloalkyl, heterocycloalkyl, C(=O)R$^3$, or S(=O)$_2$R$^3$;

each $R^3$ is independently OH, cycloalkyl or lower alkyl;

Q is $Q^2$, $Q^3$, or $Q^4$;

$Q^2$ is heterocycloalkyl, cycloalkyl, cycloalkenyl, heterocycloalkyl phenyl, heteroaryl, biaryl, or heterobiaryl, optionally substituted with one or more $Q^{2a}$;

$Q^{2a}$ is $Q^{2b}$ or $Q^{2c}$;

$Q^{2b}$ is halogen, oxo, hydroxy, —CN, —SCH$_3$, —S(O)$_2$CH$_3$, or —S(=O)CH$_3$;

$Q^{2c}$ is $Q^{2d}$ or $Q^{2e}$;

or two $Q^{2a}$ come together to form a bicyclic ring system, optionally substituted with one or more $Q^{2b}$ or $Q^{2c}$;

$Q^{2d}$ is —O(Q$^{2e}$), —S(=O)$_2$(Q$^{2e}$), —C(=O)N(Q$^{2e}$)$_2$, —S(O)$_2$(Q$^{2e}$), —C(=O)(Q$^{2e}$), —C(=O)O(Q$^{2e}$), —N(Q$^{2e}$)C(=O)(Q$^{2e}$), —N(Q$^{2e}$)C(=O)O(Q$^{2e}$), or —N(Q$^{2e}$)C(=O)N(Q$^{2e}$)$_2$;

each $Q^{2e}$ is independently H or $Q^{2e'}$;

each $Q^{2e'}$ is independently lower alkyl, phenyl, benzyl, lower haloalkyl, cycloalkyl, cycloalkenyl, heterocycloalkyl, or heteroaryl, optionally substituted with one or more $Q^{2f}$;

$Q^{2f}$ is $Q^{2g}$ or $Q^{2h}$;

$Q^{2g}$ is halogen, hydroxy, cyano, oxo, or —C(=O)(Q$^{2h}$);

$Q^{2h}$ is lower alkyl, lower haloalkyl, lower alkoxy, amino, phenyl, benzyl, cycloalkyl, heterocycloalkyl, or heteroaryl, optionally substituted with one or more $Q^{2i}$;

$Q^{2i}$ is halogen, hydroxy, cyano, lower alkyl, lower haloalkyl, or lower alkoxy;

$Q^3$ is —O-Q$^{3a}$, —S-Q$^{3a}$, —C(=O)(Q$^{3a}$), —O(CH$_2$)$_m$C(=O)(Q$^{3a}$), —S(=O)(Q$^{3a}$), —S(=O)$_2$(Q$^{3a}$), —N(Q$^{3a}$)$_2$, —N(Q$^{3a}$)S(=O)$_2$(Q$^{3a}$), —N(Q$^{3a}$)C(=O)(Q$^{3a}$), —C(=O)N(Q$^{3a}$)$_2$, N(Q$^{3a}$)C(=O)N(Q$^{3a}$)$_2$ or —N(Q$^{3a}$)(CH$_2$)$_m$C(=O)N(Q$^{3a}$)$_2$;

each $Q^{3a}$ is independently $Q^{3b}$ or $Q^{3c}$;

m is 0, 1, or 2;

$Q^{3b}$ is H;

$Q^{3c}$ is lower alkyl, lower haloalkyl, phenyl, cycloalkyl, heterocycloalkyl, or heteroaryl, optionally substituted with one or more $Q^{3d}$;

each $Q^{3d}$ is independently $Q^{3e}$ or $Q^{3f}$;

$Q^{3e}$ is halogen or hydroxy;

$Q^{3f}$ is lower alkyl, lower alkoxy, lower haloalkyl, phenyl, cycloalkyl, heterocycloalkyl, or heteroaryl, optionally substituted with one or more $Q^{3g}$;

or two $Q^{3f}$ together form a cycloalkyl, heterocycloalkyl, or heteroaryl, optionally substituted with one or more $Q^{3g}$;

each $Q^{3g}$ is independently halogen, hydroxy, lower alkyl, lower hydroxyalkyl, lower haloalkyl, amido, or lower alkoxy;

Q⁴ is Q⁴ᵃ or Q⁴ᵇ;
  Q⁴ᵃ is hydroxy, halogen, or cyano;
  Q⁴ᵇ is lower alkyl, lower alkoxy, lower alkynyl, lower alkenyl, lower hydroxyalkyl, amino, or lower haloalkyl, optionally substituted with one or more Q⁴ᶜ;
  Q⁴ᶜ is Q⁴ᵈ or Q⁴ᵉ;
    each Q⁴ᵈ is independently halogen, hydroxy, or cyano;
    each Q⁴ᵉ is independently lower alkyl, lower haloalkyl, lower alkoxy, amino, cycloalkyl, phenyl, heterocycloalkyl, or heteroaryl, optionally substituted with one or more Q⁴ᶠ; and
    each Q⁴ᶠ is independently hydroxy, halogen, lower alkyl, lower alkenyl, oxo, lower haloalkyl, lower alkoxy, lower hydroxyalkyl or amino;
or a pharmaceutically acceptable salt thereof.

2. The compound of claim 1, wherein R¹ is H.

3. The compound of claim 2, wherein Q is cycloalkyl or heteroaryl, each optionally substituted with one or more Q²ᵃ.

4. The compound of claim 3, wherein Q is cycloalkyl optionally substituted with one or more Q²ᵃ.

5. The compound of claim 3, wherein Q is heteroaryl optionally substituted with one or more Q²ᵃ.

6. The compound of claim 3, wherein R² is heteroaryl or cycloalkyl, each optionally substituted with one or more R²'.

7. The compound of claim 6, wherein R² is heteroaryl optionally substituted with one or more R²'.

8. The compound of claim 6, wherein R² is cycloalkyl optionally substituted with one or more R²'.

9. The compound of claim 3, wherein R² is phenyl or heterocycloalkyl, each optionally substituted with one or more R²'.

10. The compound of claim 9, wherein R² is phenyl optionally substituted with one or more R²'.

11. The compound of claim 6, wherein R² is heterocycloalkyl optionally substituted with one or more R²'.

12. The compound of claim 11, wherein R²' is C(=O)R³ or S(=O)₂R³, and R³ is lower alkyl.

13. The compound of claim 12, wherein R²' is C(=O)R³ and R³ is lower alkyl.

14. The compound of claim 12, wherein R²' is S(=O)₂R³ and R³ is lower alkyl.

15. A pharmaceutical composition comprising the compound of claim 1, admixed with at least one pharmaceutically acceptable carrier, excipient or diluent.

16. A compound selected from the group consisting of:

2-Cyclopropyl-5H-pyrrolo[2,3-b]pyrazine-7-carboxylic acid (tetrahydro-pyran-4-yl)-amide;
2-Cyclopropyl-5H-pyrrolo[2,3-b]pyrazine-7-carboxylic acid (4-hydroxymethyl-tetrahydro-pyran-4-yl)-amide;
2-Cyclopropyl-5H-pyrrolo[2,3-b]pyrazine-7-carboxylic acid (1-hydroxymethyl-cyclopentyl)-amide;
2-Cyclopropyl-5H-pyrrolo[2,3-b]pyrazine-7-carboxylic acid (2,2-dimethyl-tetrahydro-furan-3-yl)-amide;
2-Cyclopropyl-5H-pyrrolo[2,3-b]pyrazine-7-carboxylic acid (3-cyano-phenyl)-amide;
2-Cyclopropyl-5H-pyrrolo[2,3-b]pyrazine-7-carboxylic acid (tetrahydro-pyran-3-yl)-amide;
2-Cyclopropyl-5H-pyrrolo[2,3-b]pyrazine-7-carboxylic acid (2,2-dimethyl-cyclopentyl)-amide;
2-Cyclopropyl-5H-pyrrolo[2,3-b]pyrazine-7-carboxylic acid (3-trifluoromethyl-phenyl)-amide;
2-Cyclopropyl-5H-pyrrolo[2,3-b]pyrazine-7-carboxylic acid (5-cyano-2-methyl-phenyl)-amide;
2-Cyclopropyl-5H-pyrrolo[2,3-b]pyrazine-7-carboxylic acid (1-cyano-cyclopropyl)-amide;
2-Cyclopropyl-5H-pyrrolo[2,3-b]pyrazine-7-carboxylic acid ((trans)-2-hydroxy-2-methyl-cyclopentyl)-amide;
2-Cyclopropyl-5H-pyrrolo[2,3-b]pyrazine-7-carboxylic acid [1-(1-hydroxy-1-methyl-ethyl)-cyclopentyl]-amide;
2-Cyclopropyl-5H-pyrrolo[2,3-b]pyrazine-7-carboxylic acid [1-(1-hydroxy-1-methyl-ethyl)-cyclobutyl]-amide;
2-Cyclopropyl-5H-pyrrolo[2,3-b]pyrazine-7-carboxylic acid [1-(1-hydroxy-1-methyl-ethyl)-cyclohexyl]-amide;
2-Cyclopropyl-5H-pyrrolo[2,3-b]pyrazine-7-carboxylic acid ((3R,4S)-3-hydroxy-tetrahydro-pyran-4-yl)-amide;
2-Cyclopropyl-5H-pyrrolo[2,3-b]pyrazine-7-carboxylic acid (4,4-dimethyl-tetrahydro-furan-3-yl)-amide;
2-Cyclopropyl-5H-pyrrolo[2,3-b]pyrazine-7-carboxylic acid [3-(1-hydroxy-1-methyl-ethyl)-pyrrolidin-3-yl]-amide;
2-Cyclopropyl-5H-pyrrolo[2,3-b]pyrazine-7-carboxylic acid [3-(1-hydroxy-1-methyl-ethyl)-tetrahydro-furan-3-yl]-amide;
2-Cyclopropyl-5H-pyrrolo[2,3-b]pyrazine-7-carboxylic acid (1-cyclopropanecarbonyl-cyclopentyl)-amide;
2-Cyclopropyl-5H-pyrrolo[2,3-b]pyrazine-7-carboxylic acid (1-methanesulfonyl-pyrrolidin-3-yl)-amide;
2-Cyclopropyl-5H-pyrrolo[2,3-b]pyrazine-7-carboxylic acid (1-methanesulfonyl-piperidin-4-yl)-amide;
2-Cyclopropyl-5H-pyrrolo[2,3-b]pyrazine-7-carboxylic acid cyclohexylamide;
2-Cyclopropyl-5H-pyrrolo[2,3-b]pyrazine-7-carboxylic acid cyclopentylamide;
2-Cyclopropyl-5H-pyrrolo[2,3-b]pyrazine-7-carboxylic acid (1-methanesulfonyl-piperidin-3-yl)-amide;
2-Cyclopropyl-5H-pyrrolo[2,3-b]pyrazine-7-carboxylic acid ((cis)-2-cyano-cyclopentyl)-amide;
2-Cyclopropyl-5H-pyrrolo[2,3-b]pyrazine-7-carboxylic acid (1-cyanomethyl-cyclopentyl)-amide;

-continued

2-Cyclopropyl-5H-pyrrolo[2,3-b]pyrazine-7-carboxylic acid (1-ethanesulfonyl-piperidin-3-yl)-amide;
2-Cyclopropyl-5H-pyrrolo[2,3-b]pyrazine-7-carboxylic acid [1-(propane-1-sulfonyl)-piperidin-3-yl]-amide;
2-Cyclopropyl-5H-pyrrolo[2,3-b]pyrazine-7-carboxylic acid [1-(propane-2-sulfonyl)-piperidin-3-yl]-amide;
2-Cyclopropyl-5H-pyrrolo[2,3-b]pyrazine-7-carboxylic acid ((S)-1-methanesulfonyl-piperidin-3-yl)-amide;
2-Cyclopropyl-5H-pyrrolo[2,3-b]pyrazine-7-carboxylic acid ((R)-1-methanesulfonyl-piperidin-3-yl)-amide;
2-Cyclopropyl-5H-pyrrolo[2,3-b]pyrazine-7-carboxylic acid (2,2-dimethyl-cyclohexyl)-amide;
2-Phenoxy-5H-pyrrolo[2,3-b]pyrazine-7-carboxylic acid cyclohexylamide;
2-(2,4-Difluoro-phenoxy)-5H-pyrrolo[2,3-b]pyrazine-7-carboxylic acid cyclohexylamide;
2-Cyclopropyl-5H-pyrrolo[2,3-b]pyrazine-7-carboxylic acid (1-methanesulfonyl-4,4-dimethyl-piperidin-3-yl)-amide;
2-Cyclopropyl-5H-pyrrolo[2,3-b]pyrazine-7-carboxylic acid (1-acetyl-piperidin-4-yl)-amide;
2-Cyclopropyl-5H-pyrrolo[2,3-b]pyrazine-7-carboxylic acid (1-acetyl-pyrrolidin-3-yl)-amide;
2-Cyclopropyl-5H-pyrrolo[2,3-b]pyrazine-7-carboxylic acid (1-acetyl-piperidin-3-yl)-amide;
2-(1-Ethyl-1H-pyrazol-4-yl)-5H-pyrrolo[2,3-b]pyrazine-7-carboxylic acid (2,2-dimethyl-cyclohexyl)-amide;
2-((R)-3-Acetylamino-indan-5-yloxy)-5H-pyrrolo[2,3-b]pyrazine-7-carboxylic acid cyclohexylamide; and
2-((R)-3-Acetylamino-indan-5-yloxy)-5H-pyrrolo[2,3-b]pyrazine-7-carboxylic acid (1,1-dioxo-hexahydro-1λ6-thiopyran-4-yl)-amide.

* * * * *